US007402583B2

(12) United States Patent
Boyle et al.

(10) Patent No.: US 7,402,583 B2
(45) **Date of Patent: *Jul. 22, 2008**

(54) SUBSTITUTED QUINOLINES AS ANTITUMOR AGENTS

(75) Inventors: Francis Thomas Boyle, Cheshire (GB); Keith Hopkinson Gibson, Cheshire (GB); Kevin Michael Foote, Cheshire (GB)

(73) Assignee: AstrZenca AB, Sodertaljie (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/374,423

(22) Filed: Mar. 14, 2006

(65) Prior Publication Data

US 2007/0021407 A1 Jan. 25, 2007

(51) Int. Cl.
*A61K 31/4965* (2006.01)
*A61K 31/47* (2006.01)
*C07D 401/00* (2006.01)

(52) U.S. Cl. .................. 514/253.07; 514/312; 544/363; 546/153

(58) Field of Classification Search ................. 544/363; 514/253.07, 312; 546/153
See application file for complete search history.

(56) References Cited

U.S. PATENT DOCUMENTS

| | | | | |
|---|---|---|---|---|
| 3,936,461 | A | 2/1976 | Schwender et al. | 546/90 |
| 4,421,920 | A | 12/1983 | Baudouin et al. | 546/163 |
| 5,215,999 | A | 6/1993 | Uchida et al. | 514/313 |
| 5,409,930 | A | 4/1995 | Spada et al. | 514/248 |
| 5,650,415 | A | 7/1997 | Tang et al. | 514/312 |
| 5,656,643 | A | 8/1997 | Spada et al. | 514/312 |
| RE36,256 | E | 7/1999 | Spada et al. | 514/249 |
| 6,002,008 | A | 12/1999 | Wissner et al. | 546/160 |
| 6,521,618 | B2 * | 2/2003 | Boschelli et al. | 514/231.5 |
| 6,630,489 | B1 | 10/2003 | Crawley | 514/311 |
| 6,638,945 | B1 | 10/2003 | Gibson | 514/311 |

FOREIGN PATENT DOCUMENTS

| | | | |
|---|---|---|---|
| EP | 0 326 330 | | 8/1989 |
| FR | 2 077 455 | | 10/1971 |
| WO | 93/03030 | | 2/1993 |
| WO | WO 96/09294 | | 3/1996 |
| WO | WO 97/03069 | | 1/1997 |
| WO | WO 97/17329 | | 5/1997 |
| WO | WO 98/02434 | | 1/1998 |
| WO | WO 98/13350 | | 4/1998 |
| WO | WO 98/43960 | | 10/1998 |
| WO | WO9843960 | * | 10/1998 |
| WO | WO 99/01421 | | 1/1999 |
| WO | WO 99/01426 | | 1/1999 |
| WO | WO 99/35146 | | 7/1999 |
| WO | WO 00/18740 | | 4/2000 |
| WO | WO 00/18761 | | 4/2000 |
| WO | WO 00/68199 | | 11/2000 |
| WO | WO 00/68200 | | 11/2000 |
| WO | WO 00/68201 | | 11/2000 |
| WO | WO 02/36570 | | 5/2002 |
| WO | WO 03/008409 | | 1/2003 |
| WO | WO 2004/005284 | | 1/2004 |

OTHER PUBLICATIONS

Ca 137:190369, "Hair dyes containing cationic quinolinium direct dyes", Wella A.G., DE 20204129, Aug. 29, 2002.
Ca 89:117684, "Hydroxyethylnicotinamide vector for therapeutically active acids", Cousse et. al., Travaux de la Societe de Pharmacie de Montpellier, 1978, 38 (1), 71-6.

* cited by examiner

*Primary Examiner*—Janet L. Andres
*Assistant Examiner*—Binta Robinson
(74) *Attorney, Agent, or Firm*—Morgan, Lewis & Bockius LLP

(57) ABSTRACT

The invention provides a compound of Formula (Ia), (Ia)

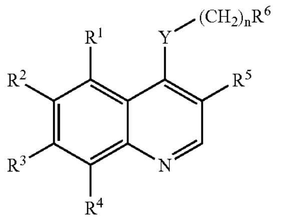

or a pharmaceutically acceptable salt thereof, a process for t he preparation of a compound of Formula (1*a*) and pharmaceutical compositions of a compound of Formula (1*a*).

7 Claims, No Drawings

SUBSTITUTED QUINOLINES AS ANTITUMOR AGENTS

The present invention relates to certain novel quinoline derivatives as well as to their use as pharmaceuticals, in particular as inhibitors of specific kinase enzymes, such as MEK enzymes. Further aspects of the invention include pharmaceutical compositions and methods of treatment of proliferative disease such as cancer using said compounds.

Cancer is a disease in which cells grow and divide in an uncontrolled fashion. This uncontrolled growth arises from abnormalities in signal transduction pathways that are used by normal cells to regulate cell growth and division in response to various signalling molecules. Normal cells do not proliferate unless stimulated to do so by specific signal molecules located outside the cell derived from nearby cells or tissues. Growth factors bind to the cell membrane via specific receptors which have intrinsic enzyme activity. These receptors relay the growth signal to the cell nucleus via a series of signalling proteins. In cancer, a number of defects in signal pathways are apparent. For example, cancer cells may produce their own growth factors which bind to their cognate receptors, resulting in an autocrine loop, or receptors may be mutated or overexpressed leading to an increased, continuous signal to proliferate. In addition, negative regulators of cell growth may be lost.

Oncogenes are cancer related genes which often encode abnormal versions of signal pathway components, such as receptor tyrosine kinases, serine-threonine kinases, or downstream signaling molecules such as the ras genes, which code for closely related small guanine nucleotide binding proteins which hydrolyse bound guanosine triphosphate (GTP) to guanosine diphosphate (GDP). Ras proteins are active in promoting cell growth and transformation when they are bound to GTP and inactive when they are bound to GDP.

Transforming mutants of p21ras are defective in their GTPase activity and hence remain in the active GTP bound state. The ras oncogene is known to play an integral role in certain cancers, and has been found to contribute to the formation of over 20% of all cases of human cancer.

When activated by ligand, cell surface receptors which are coupled to the mitogenic response, such as growth factor receptors, initiate a chain of reactions which leads to the activation of guanine nucleotide exchange activity on ras. When in its active GTP-bound state, a number of proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

The ras-dependent raf-MEK-MAPK cascade is one of the key signalling pathways responsible for transmitting and amplifying mitogenic signals from cell surface to the nucleus resulting in changes in gene expression and cell fate. This ubiquitous pathway appears essential for normal cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf, a dominant negative MEK mutant or the selective inhibitor PD098059 have been shown to block the growth and morphological transformation of ras-transformed fibroblasts.

The mechanism of activation of raf, MEK and MAPK is through phosphorylation on specific serine, threonine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on T183 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK in proliferative signalling suggest that it may be possible to discover and employ selective MEK inhibitors as therapeutic agents for use in proliferative disease.

WO 98/43960 discloses a range of 3-cyano quinoline compounds and their use in the treatment of cancer. Certain of the compounds are demonstrated as being inhibitors of Epidermal Growth Factor Receptor Kinase, and to inhibit cancer cell growth. Other quinoline derivatives which inhibit the effect of growth factors such as VEGF are described in WO98/13350.

Copending International patent application nos PCT/GB00/01697, PCT/GB00/01707 and PCT/GB00/01698 describe certain quinoline derivatives which are inhibitors of the kinase activity of MEK and as a result, can produce therapeutically useful effects in the treatment of proliferative disease and in particular cancer. The applicants have found that certain particular compounds of this type, where the substituent at the 7-position on the quinoline ring has certain characteristics, produce particularly good results.

According to the first feature of the present invention there is provided a compound of Formula (I)

(I)

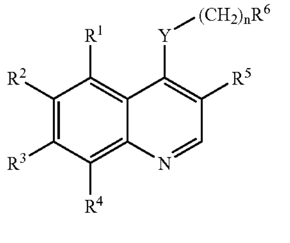

or a pharmaceutically acceptable salt, pro-drug or solvate thereof;

wherein:

n is 0 or 1;

Y is selected from —NH—, —O—, —S—, or —$NR^7$— where $R^7$ is alkyl of 1-6 carbon atoms;

$R^5$ is cyano, fluoro, chloro or bromo;

$R^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

or $R^6$ is a group —$R^8$—X—$R^9$ where $R^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

where X is selected from —NH—, —O—, —S—, $CH_2$ or —$NR^{7'}$— where $R^{7'}$ is alkyl of 1-6 carbon atoms, and $R^9$ is a group $(CH_2)_mR^{10}$ where m is 0, or an integer of from 1-3 and $R^{10}$ is an optionally substituted aryl or optionally substituted cycloalkyl ring of up to 10 carbon atoms, or $R^{10}$ is a optionally substituted heterocyclic ring or an N-oxide of any nitrogen containing ring;

$R^1$, $R^2$, $R^4$ are independently selected from hydrogen, hydroxy, halogeno, cyano, nitro, trifluoromethyl, $C_{1-3}$alkyl, —$NR^{11}R^{12}$— (wherein $R^{11}$ and $R^{12}$, which may be the same or different each represents hydrogen, or $C_{1-3}$alkyl), or a group $R^{13}$—$X^1$—$(CH_2)_x$ wherein x is 0 or an integer of from 1 to 3, $X^1$ represents a direct bond, —O—, —$CH_2$—, —OC(O)—, —C(O)—, —S—, —SO—, —$SO_2$—, —$NR^{14}$C(O)—, —$NR^{14}$C(O)O—, —C(O)$NR^{15}$—, —C(O)O$NR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl)), and $R^{13}$ is hydrogen, optionally substituted hydrocarbyl, or optionally substituted heterocyclyl;

and $R^3$ is selected from (i) a group of formula —$X^1$—$R^x$—$(OH)_p$ where $X^1$ is as defined above, $R^x$ is an alkylene, alkenylene or alkynylene chain, optionally interposed with a heteroatom or a heteocyclic ring and p is 1 or 2;

provided that when $R^x$ is alkylene $R^x$ must be interposed with a heteroatom or a heterocyclic ring and at least one $(OH)_p$ is situated on the alkylene chain between $X^1$ and the interposed heteroatom or heterocyclic ring;

(ii) a group of formula $R^{13a}$—$X^{20}$—$(CH_2)_x$ where $R^{13a}$ is as defined for $R^{13}$ above and x is as defined above and $X^{20}$ is a group —$NR^{14}$C(O)—, —C(O)$NR^{15}$— or —$NR^{18}$— where $R^{14}$, $R^{15}$ and $R^{18}$ are as defined above;

provided $R^{13a}$ is selected from phenyl or optionally substituted heterocyclyl and the optional substituents for phenyl and aromatic heterocyclyl rings are selected from: $C_{2-5}$alkenyl, hydroxy$C_{2-5}$alkenyl, $C_{2-5}$alkynyl, $C_{1-5}$alkanoyl, $C_{1-5}$alkoxycarbonyl, $C_{1-3}$alkanoyl$C_{1-3}$alkyl, $C_{1-3}$alkoxy$C_{1-3}$alkyl, $C_{1-5}$alkylthio, $C_{1-5}$alkylsulphanyl, $C_{1-5}$alkylsulphonyl, N—×$C_{1-5}$alkylamino, N,N-di-$C_{1-5}$alkylamino, guanidino, nitro, cyano$C_{1-5}$alkyl and aryl and the optional substituents for non-aromatic heterocyclyl rings further include hydroxy$C_{1-5}$alkoxy, amino, amino$C_{1-5}$alkyl, N—$C_{1-5}$alkylamino, carboxy, cyano, —$CONR^{zz}R^{zz'}$ and —$NR^{zz''}COR^{zz'''}$ (wherein $R^{zz}$, $R^{zz'}$, $R^{zz''}$ and $R^{zz'''}$ each independently represent hydrogen, $C_{1-5}$alkyl or $C_{1-3}$alkoxy$C_{1-3}$alkyl);

(iii) a group of formula —$X^1$—$R^y$—$NR^z$—$R^{y'}$—S—$R^{y''}$ where $X^1$ is as defined above, $R^y$, $R^{y'}$ and $R^{y''}$ are independently selected from alkyl, alkenyl or alkynyl chains, and $R^z$ is hydrogen or alkyl, or $R^z$ and $R^{y''}$ are joined together to form an optionally substituted nitrogen and sulphur containing ring;

provided that when $R^z$ and $R^{y''}$ are joined $R^y$ is an alkenyl or alkynyl chain and when $R^z$ and $R^{y''}$ are not joined at least one of Ry, $R^{y'}$ and $R^{y''}$ is an alkenyl or alkynyl chain; or (iv) a group of formula —$X^1$—$R^{x'}$—($C_{4-6}$cycloalkyl) where $X^1$ is as defined above and $R^x$ is an alkylene, alkenylene or alkynylene chain, optionally interposed with a heteroatom provided that when $R^x$ is alkylene and a heteroatom is interposed adjacent to $C_{4-6}$cycloalkyl, $C_{4-6}$cycloalkyl does not include cyclopentyl or cyclohexyl.

According to a further aspect of the first feature of the present invention there is provided a compound of Formula (I), or a pharmaceutically acceptable salt, pro-drug or solvate thereof, wherein $R^3$ is selected from group (i), (ii) or (iv).

According to a second feature of the present invention there is provided a compound of Formula (Ia), (Ia)

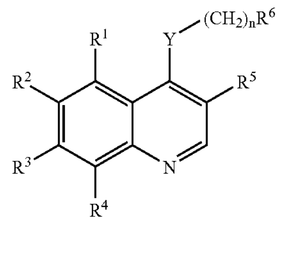

or a pharmaceutically acceptable salt, pro-drug or solvate thereof;

wherein:

n is 0 or 1;

Y is selected from —NH—, —O—, —S—, or —$NR^7$— where $R^7$ is alkyl of 1-6 carbon atoms;

$R^5$ is cyano, fluoro, chloro or bromo;

$R^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

or $R^6$ is a group —$R^8$—X—$R^9$ where $R^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, car boxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

where X is selected from —NH—, —O—, —S—, $CH_2$ or —$NR^{7'}$— where $R^{7'}$ is alkyl of 1-6 carbon atoms, and $R^9$ is a group $(CH_2)_mR^{10}$ where m is 0, or an integer of from 1-3 and $R^{10}$ is an optionally substituted aryl or optionally substituted cycloalkyl ring of up to 10 carbon atoms, or $R^{10}$ is a optionally substituted heterocyclic ring or an N-oxide of any nitrogen containing ring;

$R^1$, $R^2$, $R^4$ are independently selected from hydrogen, hydroxy, halogeno, cyano, nitro, trifluoromethyl, $C_{1-3}$alkyl, —$NR^{11}R^{12}$— (wherein $R^{11}$ and $R^{12}$, which may be the same or different each represents hydrogen, or $C_{1-3}$alkyl), or a group $R^{13}$—$X^1$—$(CH_2)_x$ wherein x is 0 or an integer of from 1 to 3, $X^1$ represents a direct bond, —O—, —$CH_2$—, —OC(O)—, —C(O)—, —S—, —SO—, —$SO_2$—, —$NR^{14}$C(O)—, —$NR^{14}$C(O)O—, —C(O)$NR^{15}$—, —C(O)O$NR^{15}$—, —$SO_2NR^{16}$—, —$NR^{17}SO_2$— —$NR^{18}$— or —$NR^{18}NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl)), and $R^{13}$ is hydrogen, optionally substituted hydrocarbyl, or optionally substituted heterocyclyl;

and $R^3$ is selected from (i) a group of formula —$X^1$—$R^x$—$(OH)_p$ where $X^1$ is as defined above, $R^x$ is an alkylene, alkenylene or alkynylene chain, optionally interposed with a heteroatom or a heteocyclic ring and p is 1 or 2;

provided that when $R^x$ is alkylene $R^x$ must be interposed with a heteroatom or a heterocyclic ring and at least one $(OH)_p$ is situated on the alkylene chain between $X^1$ and the interposed heteroatom or heterocyclic ring;

(ii) a group of formula $R^{13a}$—$(CH_2)_y$—$X^1$—$(CH_2)_x$ where $R^{13\ a}$ is as defined for $R^{13}$ above, and $X^1$ and x are as defined above, y is 0 or an integer between 1 and 5, wherein $(CH_2)_y$ is optionally interposed by an $X^1$ group;

provided that $R^{13a}$ is selected from phenyl or optionally substituted heterocyclyl and the optional substituents for phenyl and aromatic heterocyclyl rings are selected from: $C_{2-5}$alkenyl, $C_{2-5}$alkynyl, $C_{1-5}$alkanoyl, $C_{1-5}$alkoxycarbonyl, $C_{1-3}$alkanoyl$C_{1-3}$alkyl, $C_{1-3}$alkoxy$C_{1-3}$alkyl, $C_{1-5}$alkylthio, $C_{1-5}$alkylsulphanyl, $C_{1-5}$alkylsulphonyl, N,N-di-$C_{1-5}$alkylamino, cyano$C_{1-5}$alkyl and the optional substituents for non-aromatic rings further include hydroxy$C_{1-5}$alkoxy, amino, amino$C_{1-5}$alkyl, N—$C_{1-5}$alkylamino, carboxy, cyano, —$CONR^{zz}R^{zz'}$ and —$NR^{zz''}COR^{zz'''}$ (wherein $R^{zz}$, $R^{zz'}$, $R^{zz''}$ and $R^{zz'''}$ each independently represent hydrogen, $C_{1-5}$alkyl or $C_{1-3}$alkoxy$C_{1-3}$ alkyl);

(iii) a group of formula —$X^1$—$R^y$—$NR^z$—$R^{y'}$—S—$R^{y''}$ where $X^1$ is as defined above, $R^y$, $R^{y'}$ and $R^{y''}$ are independently selected from alkyl, alkenyl or alkynyl chains, and $R^z$ is hydrogen or alkyl, or $R^z$ and $R^{y''}$ are joined together to form an optionally substituted nitrogen and sulphur containing ring;

provided that at least one of $R^y$, $R^{y'}$ and $R^{y''}$ is an alkenyl or alkynyl chain;

(iv) a group of formula —$X^1$—$R^{x'}$—($C_{3-6}$cycloalkyl) where $X^1$ is as defined above and $R^{x'}$ is an alkylene, alkenylene or alkynylene chain, optionally interposed with a heteroatom provided that when $R^{x'}$ is alkylene and a heteroatom is interposed adjacent to $C_{3-6}$cycloalkyl, $C_{3-6}$cycloalkyl does not include cyclopentyl or cyclohexyl;

(v) a group of the formula —$X^1$—$C_{1-5}$alkyl where $X^1$ is as defined above and $C_{1-5}$alkyl is substituted by one more substituents independently selected from chloro and cyano;

(vi) a group of the formula —$X^1$—$C_{1-3}$alkyl-CO—$NR^{18}NR^{18}$—$R^{20}$ where $R^{18}$ is as defined above and $R^{20}$ is selected from hydrogen or $C_{1-5}$alkoxycarbonyl; or (vii) a heterocyclic ring.

According to a further aspect of the second feature of the present invention there is provided a compound of Formula (Ia), or a pharmaceutically acceptable salt, pro-drug or solvate thereof, wherein $R^3$ is selected from group (i), (ii) or (iv).

According to a further aspect of the second feature of the present invention there is provided a compound of Formula (Ia), or a pharmaceutically acceptable salt, pro-drug or solvate thereof, wherein $R^3$ is selected from group (ii) and $R^{13a}$ is optionally substituted heterocyclyl.

According to a further aspect of the second feature of the present invention there is provided a compound of Formula (Ia), or a pharmaceutically acceptable salt, pro-drug or solvate thereof, wherein $R^3$ is selected from group (ii), x is 0 and $R^{13a}$ is optionally substituted heterocyclyl.

According to a further aspect of the second feature of the present invention there is provided a compound of Formula (Ia), or a pharmaceutically acceptable salt, pro-drug or solvate thereof, wherein $R^3$ is selected from group (ii), x is 0 and $R^{13a}$ is optionally substituted heterocyclyl attached to —$(CH_2)_y$— via a ring heteroatom and the optional substituents on heterocyclyl further include $C_{1-4}$alkyl or di-$C_{1-4}$alkyl attached to the ring carbon atoms adjacent to the heteroatom linked to —$(CH_2)_y$—. Preferably $R^{13a}$ is 24-di-$C_{1-4}$alkylazetin-1-yl, 2,5-di-$C_{1-4}$alkylpyrrolin-1-yl or 2,6-di-$C_{1-4}$alkylpiperidin-1-yl. More preferably $R^{13}$ is 2,5-dimethylpyrrolin-1-yl or 2,6-dimethylpiperidin-1-yl.

In this specification the term 'alkyl' when used either alone or as a suffix includes straight chained, branched structures.

Unless otherwise stated, these groups may contain up to 10, preferably up to 6 and more preferably up to 4 carbon atoms. Similarly the terms “alkenyl” and “alkynyl” refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as “alkoxy” comprise alkyl groups as is understood in the art.

The term “halo” or “halogeno” includes fluoro, chloro, bromo and iodo. References to aryl groups include aromatic carbocylic groups such as phenyl and naphthyl. The term “heterocyclyl” or “heterocyclic” includes aromatic or non-aromatic rings, for example containing from 4 to 20, suitably from 5 to 8 ring atoms, at least one of which, and preferably from 1-4 of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

“Heteroaryl” refers to those groups described above which have an aromatic character. The term “aralkyl” refers to aryl substituted alkyl groups such as benzyl.

Other expressions used in the specification include “hydrocarbyl” which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynyl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term “interposed” used in relation to heteroatoms in hydrocarbyl chains means that the chains include a heteroatom such as sulphur, oxygen or nitrogen either at an intermediate position along their length or at an end of the chain.

The term “interposed” used in relation to heterocyclic rings in hydrocarbyl chains means that the chains include a heterocyclic ring either at an intermediate position along their length or at an end of the chain.

Suitable pharmaceutically acceptable salts of compounds of Formula (I) include acid addition salts such as methanesulfonate, fumarate, hydrochloride, hydrobromide, citrate, maleate and salts formed with phosphoric and sulphuric acid. A preferred pharmaceutically acceptable salt is a hydrochloride salt.

Thus, the alkyl portion of the alkyl, alkoxy, alkanoyloxy, alkoxymethyl, alkanoyloxymethyl, alkylsuphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cycloalkyl-N-alkylaminoalkyl and N,N-dicycloalkylaminoalkyl substituents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2$H radical. Carboalkoxy of 2-7 carbon atoms is defined as a —$CO_2$R" radical, where R" is an alkyl radical of 1-6 carbon atoms. Carboalkyl is defined as a —COR" radical, where R" is an alkyl radical of 1-6 carbon atoms. Alkanoyloxy is defined as a —OCOR" radical, where R" is an alkyl radical of 1-6 carbon atoms. Alkanoyloxymethyl is defined as R"$CO_2CH_2$— radical, where R" is an alkyl radical of 1-6 carbon atoms. Alkoxymethyl is defined at R"$OCH_2$— radical, where R" is an alkyl radical of 1-6 carbon atoms. Alkylsulphinyl is defined as R"SO— radical, where R" is an alkyl radical of 1-6 carbon atoms. Alkylsulphonyl is defined as R"$SO_{2-}$ radical, where R" is alkyl radical of 1-6 carbon atoms. Alkylsulfonamido, alkenylsulfonamido, alkynylsulfonamido are defined as R"$SO_2$NH— radical, where R" is an alkyl radical of 1-6 carbon atoms, an alkenyl radical of 2-6 carbon atoms, or an alkynyl radical of 2-6 carbon atoms, respectively. N-alkylcarbamoyl is defined as R"NHCO— radical, where R" is an alkyl radical of 1-6 carbon atoms. N,N-dialkylcarbamoyl is defined as R"R'NCO— radical, where R" is an alkyl radical of 1-6 carbon atoms, R' is an alkyl radical of 1-6 carbon atoms and R', and R" may be the same or different. When X is substituted, it is preferred that it is mono-, di-, or tri-substituted, with monosubstituted being most preferred. It is preferred that of the substituents, $R_1$, $R_2$ and $R_4$ at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A pipeazino-N-alkyl substituent is a piperazine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

When any group contains an alkyl portion, the alkyl portion contains preferably 1-6 carbon atoms, more preferably 1-4 carbon atoms, particularly methyl, ethyl, n-propyl, iso-propyl, n-butyl, iso-butyl, sec-butyl or tert-butyl. When any group contains an alkenyl or alkynyl portion, the alkenyl or alkynyl portion contains preferably 2-6 carbon atoms, more preferably 2-4 carbon atoms.

The compounds of this invention may contain an asymmetric carbon; in such cases, the compounds of this invention cover the racemate and the individual R and S entantiomers, and in the case were more than one asymmetric carbon exists, the individual diasteromers, their racemates and individual entantiomers.

When $R^3$ is a group of formula —$X^1$—$R^x$—$(OH)_p$, suitable examples of $X^1$ are —O—, —$NR^{14}$C(O)—, —C(O)$NR^{15}$— or —$NR^{18}$— where $R^{14}$, $R^{15}$ and $R^{18}$ are as defined above. Preferably $X^1$ is selected from —O—, —$NR^{14}$C(O)—, or —$NR^{18}$—. In particular $X^1$ is —O—. Particular examples of $R^x$ are $C_{2-6}$alkylene chains which is interposed by at least one heteroatom such as nitrogen, or a heterocyclic ring, in particular, a saturated 5-6 membered heterocyclic ring. The ring suitably contains at least from one to three and preferably one heteroatom which is suitably nitrogen. In particular, the heterocyclic ring is a saturated heterocyclic ring.

The hydroxy groups may be attached to the alkylene portion of the group $R^x$ or where present, the heterocyclic ring. In particular, these groups are groups of sub-formula (i)

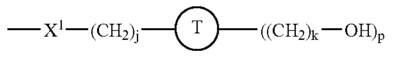

(i)

where $X^1$ and p is as defined above, T is a 5 or 6 membered nitrogen containing ring, j is 2, 3, 4, or 5, and k is 0, 1, 2 or 3. Preferably $R^x$ is interposed by a nitrogen atom or is not interposed by a heteroatom or a heterocyclic ring.

Where the alkylene chain $R^x$ is interposed with a nitrogen atom, it is suitably in the form or a group —$NR^{75}$— where $R^{75}$ is hydrogen or $C_{1-4}$alkyl (optionally substituted by hydroxy), in particular $C_{1-3}$alkyl or hydroxy$C_{1-3}$alkyl.

Where $R^3$ is a group of formula $R^{13a}$—$X^{20}$—$(CH_2)_x$, x is suitably 0. Preferred groups for $R^{13a}$ are heterocyclic rings, preferably saturated heterocyclic rings.

Where $R^3$ is a group of formula $R^{13a}$—$(CH_2)_y$—$X^1$—$(CH_2)_x$, x is suitably 0 and y is an integer between 1 and 4.

Preferred groups for $R^{13a}$ are heterocyclic rings, preferably saturated heterocyclic rings. Preferred saturated heterocyclic rings are selected from azetidinyl, pyrrolidinyl, tetrahydrofuranyl, 1,3-dioxolanyl, 1,3-oxazolidineyl 1,2,4-oxadiazolidinyl, tetrahydrothiophenyl, 1-oxo-tetrahydrothiophenyl, 1,1-dioxo-tetrahydrothiophenyl, morpholinyl, piperidinyl, piperazinyl, 1,3-dioxanyl, tetrahydropyranyl, tetrahydrothiopyranyl, 1-oxo-tetrahydrothiopyranyl, 1,1-dioxo-tetrahydrothiopyranyl, thiomorpholinyl, 1-oxothiomorpholinyl and 1,1-dioxo-thiomorpholinyl. More preferred saturated heterocyclic rings are selected from azetidinyl, pyrrolidinyl, tetrahydrofuranyl, 1,3-dioxolanyl, 1,3-oxazolidinyl, 1,2,4-oxadiazolidinyl, 1,1-dioxoctetrahydrothiophenyl, morpholinyl, piperidinyl, piperazinyl, 1,3-dioxanyl, tetrahydropyranyl, 1,1-dioxotetrahydrothiopyranyl, thiomorpholinyl, 1-oxo-thiomorpholinyl and 1,1-dioxo thiomorpholinyl. Preferred aromatic heterocyclyl rings are selected from: furanyl, thiophenyl, pyrrolyl, pyrrolinyl, imidazolyl, imidazolinyl, pyrazolyl, pyrazolinyl, triazolyl, thiazolyl, isothiazolyl, oxadiazolyl, oxazolyl, isoxazolyl, thiadiazolyl, 2,5-dihydro-1,2,4-oxadiazolyl, pyrazinyl, pyridazinyl, pyrimidinyl and triazinyl. More preferred aromatic heterocyclyl rings are selected from: 2,3-dihydropyrrolyl, imidazolyl, pyrazolyl, 1,3-thiazolyl, 1,3,4-oxadiazolyl, isoxazolyl, 1,2,4-thiadiazolyl, furanyl, 2,5-dihydro-1,2,4-oxadiazolyl and pyrimidinyl. Suitably $R^{14}$, $R^{15}$ and $R^{18}$ are hydrogen or $C_{1-3}$ alkyl and preferably hydrogen.

Preferred substituents on $R^{13a}$ are selected from nitro, $C_{2-5}$alkenyl, $C_{1-3}$alkoxy$C_{1-3}$alkyl, $C_{1-5}$alkanoyl and $C_{1-5}$alkylsulphonyl. More preferred substituents on $R^{13a}$ are selected from $C_{1-3}$alkoxy$C_{1-3}$alkyl, $C_{1-5}$alkanoyl and $C_{1-5}$alkylsulphonyl. Most preferred substituents on $R^{13a}$ are selected from acetyl, methoxyethyl, methylsulphonyl and ethylsulphonyl. Preferred substituted heterocyclic rings at $R^{13a}$ are selected from: 2,6-dimethylmorpholino, 4-methoxyethylpiperazin-1-yl, 4-acetylpiperazin-1-yl, 3-methylsulphonylpyrrolidin-1-yl and 4-ethylsulphonylpiperazin-1-yl.

Particular examples of groups of formula —$X^1$—$R^y$—$NR^z$—$R^{y'}$—S—$R^{y''}$ for $R^3$ are groups where $X^1$ is —O—, —$NR^{14}C(O)$—, —$C(O)NR^{15}$— or —$NR^{18}$— where $R^{14}$, $R^{15}$ and $R^{18}$ are as defined above. Preferably $X^1$ is selected from —O—, —$NR^{14}C(O)$—, or —$NR^{18}$—. In particular $X^1$ is —O—. Suitably $R^y$ is a $C_{2-6}$alkenylene group. Suitably $R^{y''}$ is a $C_{2-3}$alkylene group. Suitably $R^z$ is hydrogen or $C_{1-3}$alkyl and in particular is hydrogen.

In one embodiment however, the group —$NR^z$—$R^{y'}$—S—$R^{y''}$ is a thiomorpholine ring.

Where $R^3$ is a group of formula —$X^1$—$R^{x'}$—($C_{4-6}$cycloalkyl) or a group of the formula —$X^1$—$R^{x'}$—($C_{3-6}$cycloalkyl), $X^1$ is suitably —O—, —$NR^{14}C(O)$—, —$C(O)NR^{15}$— or —$NR^{18}$— where $R^{14}$, $R^{15}$ and $R^{18}$ are as defined above. Preferably $X^1$ is selected from —O—, —$NR^{14}C(O)$—, or —$NR^{18}$—. In particular $X^1$ is —O—. Particular examples of $R^{x'}$ are $C_{2-5}$alkylene groups which suitably include at least one heteroatom in particular a group —$NR^{75}$— where $R^{75}$ is as defined above. Suitably the $C_{4-6}$cycloalkyl group is cyclopropyl.

In particular $R^1$, $R^2$ and $R^4$ are selected from hydrogen, hydroxy, halogeno, cyano, nitro, trifluoromethyl, $C_{1-3}$alkyl, —$NR^{11}R^{12}$— (wherein $R^{11}$ and $R^{12}$ are as defined above), or $R^{13}X^1$—$(CH_2)_x$— (wherein x is 0 or an integer of from 1-3, $X^1$ represents a direct bond, —O—, —$CH_2$—, —OC(O)—, —C(O)—, —S—, —SO—, —$SO_2$—, —$NR^{14}C(O)$—, —$NR^{14}C(O)O$—, —$C(O)NR^{15}$—, —$C(O)ONR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl)), and $R^{13}$ is any one of the following twenty-two groups 1') $C_{1-5}$alkyl which may be unsubstituted or which may be substituted with one or more groups selected from hydroxy, oxiranyl, fluoro, chloro, bromo and amino (including $C_{1-3}$alkyl and trifluoromethyl);

2') —$R^aX^2C(O)R^{19}$ (wherein $X^2$ represents —O— or —$NR^{20}$— (in which $R^{20}$ represents hydrogen, $C_{1-3}$alkyl or $C_{1-3}$alkoxy$C_{2-3}$alkyl) and $R^{19}$ represents $C_{1-3}$alkyl, —$NR^{21}R^{22}$ or —$OR^{23}$ (wherein $R^{21}$, $R^{22}$ and $R^{23}$ which may be the same or different each represents hydrogen, $C_{1-5}$alkyl. hydroxy$C_{1-5}$alkyl or $C_{1-3}$alkoxy$C_{2-3}$alkyl));

3') —$R^bX^3R^{24}$ (wherein $X^3$ represents —O—, C(O)—S—, —SO—, —$SO_2$—, —OC(O)—, —$NR^{25}C(O)$—, —$NR^{25}C(O)O$—, —$C(O)NR^{26}$—, —$C(O)ONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl, hydroxy $C_{1-4}$alkyl or $C_{1-3}$alkoxy$C_{2-3}$alkyl and $R^{24}$ represents hydrogen, $C_{1-6}$alkyl, $C_{2-6}$alkenyl, cyclopropyl, cyclobutyl, cyclopentyl, cyclohexyl, phenyl or a 5-6-membered saturated heterocyclic group with 1-2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, $C_{1-4}$alkanoyldi-$C_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$ alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—$)_f$($R^{b'}$$)_g$D (wherein f is 0 or 1, g is 0 or 1 and D is a $C_{3-6}$cycloalkyl group or a 5-6-membered saturated heterocyclic group with 1-2 heteroatoms, selected independently from O, S and N, which cyclic group may bear one or more substituents selected from $C_{1-4}$alkyl));

4') —$R^cX^4R^{c'}X^5R^{30}$ (wherein $X^4$ and $X^5$ which may be the same or different are each —O—, C(O), —S—, —SO—, —$SO_2$—, —$NR^{31}C(O)$—, —$NR^{31}C(O)O$—, —$C(O)NR^{32}$—, —$C(O)ONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl and $R^{30}$ represents hydrogen, $C_{1-3}$alkyl, hydroxy$C_{1-3}$alkyl or $C_{1-3}$alkoxy$C_{2-3}$alkyl);

5') $R^{d}R^{36}$ (wherein $R^{36}$ is a 4-6-membered cycloalkyl or saturated heterocyclic ring (linked via carbon or nitrogen) with 1-2 heteroatoms, selected independently from O, S and N, which cycloalkyl or heterocyclic group may bear 1 or 2 substituents selected from oxo, hydroxy, halogeno, cyano, $C_{1-4}$alkyl hydroxy$C_{1-4}$alkyl, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy nitro, amino, $C_{1-4}$alkoxy, $C_{1-4}$hydroxyalkoxy, carboxy, trifluoromethyl, —C(O)$NR^{65}R^{66}$, —$NR^{67}$C(O)$R^{68}$ (wherein $R^{65}$, $R^{66}$, $R^{67}$ and $R^{68}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($R^{b}$)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

6') $R^{e}X^{6}R^{37}$ (wherein $X^{6}$ represents a direct bond, —O—, —C(O)—, —S—, —SO—, —$SO_2$—, —$NR^{38}$CO—, —$NR^{38}$C(O)O—, —CON$R^{39}$—, —C(O)ON$R^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxy, carboxamido, trifluoromethyl, cyano, —C(O)$NR^{43}R^{44}$, —$NR^{45}$C(O)$R^{46}$ (wherein $R^{43}$, $R^{44}$, $R^{45}$ and $R^{46}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($R^{b'}$)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

7') —$R^{f}R^{36}$ (wherein $R^{36}$ is as defined in (5') hereinbefore);

8') —$R^{g}R^{36}$ (wherein $R^{36}$ is as defined in (5') hereinbefore);

9') $X^{7}R^{47}$ (wherein $X^{7}$ is —$SO_2$—, —O— or —CON$R^{48}R^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^{7}$ is —$SO_2$—, $X^{1}$ is —O—, when $X^{7}$ is —O—, $X^{1}$ is carbonyl, when $X^{7}$ is —CON$R^{48}R^{49}$—, $X^{1}$ is —O— or $NR^{18}$ (wherein $R^{48}$, $R^{49}$ and $R^{18}$ are as defined in (6') hereinbefore);

10') —$R^{h}R^{37}$ (wherein $R^{37}$ is as defined in (6') hereinbefore);

11')—$R^{i}R^{37}$ (wherein $R^{37}$ is as defined in (6') hereinbefore);

12') —$R^{j}X^{8}R^{37}$ (wherein $X^{8}$ represents —O—, —C(O)—, —S—, —SO—, —$SO_2$—, —OC(O)—, —$NR^{50}$C(O)—, —$NR^{50}$C(O)O—, —C(O)$NR^{51}$—, —C(O)O$NR^{51}$—, —$SO_2NR^{52}$—, —$NR^{53}SO_2$— or —$NR^{54}$— (wherein $R^{50}$, $R^{51}$, $R^{52}$, $R^{53}$ and $R^{54}$ each independently represents hydrogen, $C_{1-3}$alkyl, hydroxy$C_{1-3}$alkyl or $C_{1-3}$alkoxy$C_{2-3}$alkyl) and $R^{37}$ is as defined in (6') hereinbefore);

13') —$R^{k}X^{9}R^{37}$ (wherein $X^{9}$ represents —O—, C(O), —S—, —SO—, —$SO_2$—, —$NR^{55}$C(O)—, —$NR^{55}$C(O)O—, —C(O)$NR^{56}$—, —C(O)O$NR^{56}$—, —$SO_2NR^{57}$—, —$NR^{58}SO_2$— or —$NR^{59}$— (wherein $R^{55}$, $R^{56}$, $R^{57}$, $R^{58}$ and $R^{49}$ each independently represents hydrogen, $C_{1-3}$alkyl, hydroxy$C_{1-3}$alkyl or $C_{1-3}$alkoxy$C_{2-3}$alkyl) and $R^{37}$ is as defined in (6') hereinbefore);

14') —$R^{m}X^{10}R^{m'}R^{37}$ (wherein $X^{10}$ represents —O—, —C(O)—, —S—, —SO—, —$SO_2$—, —$NR^{60}$C(O)—, —$NR^{60}$C(O)O—, —C(O)$NR^{61}$—, —C(O)O$NR^{61}$—, —$SO_2NR^{62}$—, —$NR^{63}SO_2$— or —$NR^{64}$— (wherein $R^{60}$, $R^{61}$, $R^{62}$, $R^{63}$ and $R^{64}$ each independently represents hydrogen, $C_{1-3}$alkyl, hydroxy$C_{1-3}$alkyl or $C_{1-3}$alkoxy$C_{2-3}$alkyl) and $R^{37}$ is as defined in (6') hereinbefore);

15') $R^{36}$ (where $R^{36}$ is as defined in (5') hereinbefore);

16') —$R^{n}X^{10}R^{n'}R^{36}$ (wherein $X^{10}$ is as defined in (14') above and $R^{36}$ is as defined in (5') hereinbefore);

17') —$R^{p}X^{10}$—$R^{p'}R^{37}$ (wherein $X^{10}$ is as defined in (14') above and $R^{37}$ are as defined in (6') hereinbefore);

18') $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19') $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20')—$R^{t}X^{10}R^{t'}R^{36}$ (wherein $X^{10}$ is as defined in (14') above and $R^{36}$ is as defined in (5') hereinbefore);

21') —$R^{u}X^{10}R^{u'}R^{36}$ (wherein $X^{10}$ is as defined in (14') above and $R^{36}$ is as defined in (5') hereinbefore); and 22') —$R^{v}R^{69}(R^{v'})_q(X^{10})_rR^{70}$ (wherein $X^{10}$ is as defined in (14') above, q is 0 or 1, r is 0 or 1, and $R^{69}$ is a $C_{1-3}$alkylene group or a cyclic group selected from cyclopropyl, cyclobutyl, cyclopentylene, cyclohexylene or a 5-6-membered saturated heterocyclic group with 1-2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, i($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($R^{b'}$)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl); and $R^{70}$ is hydrogen, $C_{1-3}$alkyl, or a cyclic group selected from cyclopropyl, cyclobutyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($R^{b'}$)$_g$ringD (wherein f is 0 or 1, g is 0 or 1 and D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

and wherein $R^a$, $R^b$, $R^{b'}$, $R^c$, $R^{c'}$, $R^d$, $R^e$, $R^i$, $R^m$, $R^{m'}$ $R^n$, $R^{n'}$, $R^{p'}$, $R^{t'}$, $R^{u'}$, $R^v$ and $R^{v'}$ are independently selected from $C_{1-8}$alkylene groups optionally substituted by one or more substituents selected from hydroxy, halogeno, amino; and $R^e$ may additionally be a bond; and $R^f$, $R^h$, $R^j$, $R^p$ and $R^t$ are independently selected from $C_{2-8}$alkenylene groups optionally substituted by one or more substituents selected from hydroxy, halogeno, amino, and $R^t$ may additionally be a bond; and $R^g$, $R^k$ and $R^u$ are independently selected from by $C_{2-8}$alkynylene groups optionally susbstituted by one or more substituents selected from hydroxy, halogeno, amino, subject to the proviso set out above.

In one embodiment, at least one group $R^1$, $R^2$ or $R^4$ is a group $R^{13}$—$X^1$—$(CH_2)_x$— (wherein x is 0 or an integer of from 1-3, $X^1$ represents —$NR^{14}C(O)O$—, or $C(O)ONR^{15}$—, (wherein $R^{13}R^{14}$ and $R^{15}$ are as defined above). A particular example of such a group for $R^1$, $R^2$, $R^3$ or $R^4$ is a group —$NHC(O)OR^{13}$ where $R^{13}$ is as defined above, and in particular is a group of formula (6') such as benzyl.

In particular, at least one group $R^1$, $R^2$ or $R^4$ is selected from $R^{13}X^1$—$(CH_2)_x$— (wherein x is 0 or an integer of from 1-3, $X^1$ represents a direct bond, —O—, —$CH_2$—, —OC(O)—, —C(O)—, —S—, —SO—, —$SO_2$—, —$NR^{14}C(O)$—, —$NR^{14}C(O)O$—, —$C(O)NR^{15}$—, —$C(O)ONR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl)), and $R^{13}$ is any one of the following twenty-two groups;

1") $C_{1-5}$alkyl substituted with one or more groups selected from oxiranyl, chloro or bromo;

2") —$R^aX^2C(O)R^{19}$ (wherein $X^2$ and $R^{19}$ are as defined in (2') above, and $R^a$ is a $C_{1-8}$alkylene groups substituted by one or more substituents selected from hydroxy, halogeno, amino, 3") —$R^bX^3R^{24}$ (wherein either $R^{24}$ is any of the groups defined in (3') above and $X^3$ is —C(O), —$NR^{25}C(O)O$—, —$C(O)ONR^{26}$— (wherein $R^{25}$ and $R^{26}$ are as defined in (3') above), or $X^3$ is any other groups defined in (3') above and $R^{24}$ represents $C_{1-3}$alkyl, $C_{3-6}$alkyl, $C_{2-6}$alkenyl, cyclopropyl, cyclobutyl, cyclopentyl, cyclohexyl or phenyl, wherein (a) the $C_{3-6}$alkyl group may, bear 1, 2 or 3 substituents selected from oxo, hydroxy, halogeno, cyclopropyl, amino, $C_{1-4}$alkylamino, $C_{1-4}$alkanoyldi-$C_{1-4}$alkylamino, $C_{1-4}$alkylthio, $C_{1-4}$alkoxy; (b) the $C_{1-3}$ alkyl group may be similarly substituted to the $C_{3-6}$alkyl provided it includes at least one substitutent selected from cyclopropyl, amino, $C_{1-4}$alkylamino, $C_{1-4}$alkanoyldi-$C_{1-4}$alkylamino, $C_{1-4}$alkylthio, $C_{1-4}$alkoxy; (c) the cyclopropyl or cyclobutyl may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($R^{b'}$)$_g$D (wherein f, g $R^b$ and D are as defined above); (d) the cyclopentyl or cyclohexyl may be similarly substituted provided it includes at least one substituent selected from cyano, $C_{1-4}$cyanoalkyl, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$ alkyl)amino$C_{1-4}$alkyl, $C_{1-4}$alkylamino$C_{1-4}$alkoxy, di($C_{1-4}$ alkyl)amino$C_{1-4}$alkoxy and a group —(—O—)$_f$($R^{b'}$)$_g$D (wherein f, g $R^{b'}$ and D are as defined above), or $X^3$ and $R^{24}$ are any of the groups defined in 3' above and $R^b$ is other than $C_{1-5}$alkylene;

4") —$R^cX^4R^{c'}X^5R^{30}$ (wherein $R^c$, $R^{c'}$ and $R^{30}$ are as defined in (4') above and $X^4$ and $X^5$ are as defined above provided at least one of these is selected from C(O), —$NR^{31}C(O)O$—, or —$C(O)ONR^{32}$— (wherein $R^{31}$ and $R^{32}$ are as defined in (4') above), or $X^4$ and $X^5$ are any of the groups defined in (4') above, and either $R^{30}$ is hydroxy$C_{1-3}$alkyl or $C_{1-3}$alkoxy$C_{2-3}$alkyl), or at least one of $R^c$ or $R^c$ is other than an unsubstituted $C_{1-5}$alkylene group;

5") $R^dR^{36}$ (wherein $R^d$ is as defined above, and $R^{36}$ is a 4-6-membered cycloalkyl or a saturated heterocyclic ring (linked via carbon or nitrogen including for example from 4 to 7 atoms) with 1-2 heteroatoms, selected independently from O, S and N, which cycloalkyl or heterocyclic group may bear 1 or 2 substituents listed in (5') above, provided that where $R^{36}$ is a 5 or 6 membered heterocyclic ring, either it carries at least one substitutent selected from cyano, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$ alkyl, $C_{1-4}$alkylamino$C_{1-4}$alkoxy, di($C_{1-4}$alkyl)amino$C_{1-4}$ alkoxy nitro, amino, $C_{1-4}$hydroxyalkoxy, carboxy, trifluoromethyl, —$C(O)NR^{65}R^{66}$, —$NR^{67}C(O)R^{68}$ (wherein $R^{65}$, $R^{66}$, $R^{67}$ and $R^{68}$, are as defined in (5') above and a group —(—O—)$_f$($R^{b'}$)$_g$ringD (wherein f, g, $R^{b'}$ and D are as defined above); $R^{36}$ is any of the groups defined in 5' above and $R^d$ is other than $C_{1-5}$alkyl;

6") $R^eX^6R^{37}$ (wherein $R^e$ and $R^{37}$ are any of the groups defined above, provided that $X^6$ represents —C(O)—, —$NR^{38}C(O)O$—, or —$C(O)ONR^{39}$—, (wherein $R^{38}$ and $R^{39}$ are as defined above) or, $X^6$ is any other group listed in (6') above, provided that either $R^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, $C_{1-4}$hydroxyalkoxy, oxo, cyano$C_{1-4}$alkyl, cyclopropyl, $C_{1-4}$alkylsulphonyl$C_{1-4}$ alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$ alkyl, $C_{1-4}$alkylamino$C_{1-4}$alkoxy, di($C_{1-4}$alkyl)amino$C_{1-4}$ alkoxy, carboxamido, trifluoromethyl, or a group —(—O—)$_f$($R^{b'}$)$_g$ringD (wherein f, g, $R^{b'}$ and D are as defined above) or $R^e$ is other than a direct bond or a $C_{1-5}$alkylene group;

7") —$R^fR^{36}$ (wherein $R^f$ and $R^{36}$ are as defined in (7') above provided that where $R^f$ is unsubstituted $C_{2-6}$ alkenylene, $R^{36}$ is as defined in (5") hereinbefore);

8") —$R^gR^{36}$ (wherein $R^g$ and $R^{36}$ are as defined in (8') above provided that where $R^g$ is unsubstituted $C_{2-6}$ alkynylene, $R^{36}$ is as defined in (5") hereinbefore);

10") —$R^hR^{37}$ (wherein $R^h$ and $R^{37}$ are as defined in (10') above provided that where $R^h$ is unsubstituted $C_{2-6}$ alkenylene, $R^{37}$ is $R^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxamido, trifluoromethyl, or a group —(—O—)$_f$($R^{b'}$)$_g$ringD (wherein f, g, $R^{b'}$ and D are as defined above));

11")—$R^iR^{37}$ (wherein $R^i$ and $R^{37}$ are as defined in (11') above provided that where $R^i$ is unsubstituted $C_{2-6}$ alkynylene, $R^{37}R^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxamido, trifluoromethyl, or a group —(—O—)$_f$$R^{b'}$)$_g$ringD (wherein f, g, $R^b$ and D are as defined above);

12")—$R^jX^8R^{37}$ (wherein $R^j$ and $R^{37}$ are as defined in (12') above, and $X^8$ is —C(O)—, —$NR^{50}$C(O)O— or —C(O)$ONR^{51}$— (wherein $R^{50}$ and $R^{51}$ are as defined in (12') above, or $X^8$ is any other group listed in (12' above) and either $R^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxamido, trifluoromethyl, or a group —(—O—)$_f$($R^b$)$_g$ringD (wherein f, g, $R^{b'}$ and D are as defined above); or $R^j$ is other than unsubstituted $C_{2-6}$alkenylene;

13") —$R^kX^9R^{37}$ (wherein $R^k$ and $R^{37}$ are as defined in (13') above, and $X^9$ is —C(O)—, —$NR^{55}$C(O)O— or —C(O)$ONR^{56}$— (wherein $R^{55}$ and $R^{56}$ are as defined in (13') above, or $X^9$ is any other group listed in (13' above) and either $R^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxamido, trifluoromethyl, or a group —(—O—)$_f$($R^{b'}$)$_g$ringD (wherein f, g, $R^{b'}$ and D are as defined above); or $R^k$ is other than unsubstituted $C_{2-6}$alkynylene 14") —$R^mX^{10}R^{m'}R^{37}$ (wherein $R^m$, $R^{m'}$ and $R^{37}$ are as defined in (14') above, and $X^{10}$ represents —C(O)—, —$NR^{60}$C(O)O— or —C(O)$ONR^{61}$—, (wherein $R^{60}$ and $R^{61}$ are as defined in (14') above, or where $X^{10}$ is any other group listed in (14') above, and either $R^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxamido, trifluoromethyl, or a group —(—O—)$_f$($R^{b'}$)$_g$ringD (wherein f, g, $R^{b'}$ and D are as defined above), or at least one of $R^m$ or $R^{m'}$ is other than unsubstituted $C_{1-3}$alkylene);

15") $R^{36}$ (where $R^{36}$ is as defined in (5") hereinbefore);

16") —$R^nX^{10}R^{n'}R^{36}$ (wherein $R^n$, $R^{n'}$ and $R^{36}$ are as defined in (16') above and $X^{10}$ represents —C(O)—, —$NR^{60}$C(O)O— or —C(O)$ONR^{61}$—, (wherein $R^{60}$ and $R^{61}$ are as defined in (14') above or $X^{10}$ is any of the other groups set out in (14') above and either $R^{36}$ is as defined in (5") hereinbefore) or at least one of $R^n$ or $R^{n'}$ is other than unsubstituted $C_{1-3}$alkyl;

17") —$R^pX^{10}$—$R^{p'}R^{37}$ (wherein X is as defined in (14') above and $R^p$, $R^{p'}$ and $R^{37}$ are as defined in (6') hereinbefore);

18") $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19") $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20") —$R^tX^{10}R^{t'}R^{36}$ (wherein $X^{10}$ is as defined in (14') above and $R^{36}$ is as defined in (5') hereinbefore);

21") —$R^uX^{10}R^{u'}R^{36}$ (wherein $X^{100}$ is as defined in (14') above and $R^{36}$ is as defined in (5') hereinbefore); and 22") —$R^vR^{69}(R^{v'})_q(X^{10})_rR^{70}$ (wherein $X^{10}$ is as defined in (14') above, q is 0 or 1, r is 0 or 1, and $R^{69}$ is a $C_{1-3}$alkylene group or a cyclic group selected from cyclopropyl, cyclobutyl, cyclopentylene, cyclohexylene or a 5-6-membered saturated heterocyclic group with 1-2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, i($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($R^{b'}$)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl); and $R^{70}$ is hydrogen, $C_{1-3}$alkyl, or a cyclic group selected from cyclopropyl, cyclobutyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$oxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

and wherein $R^a$, $R^b$, $R^{b'}$, $R^c$, $R^{c'}$, $R^d$, $R^e$, $R^i$, $R^m$, $R^{m'}R^n$, $R^{n'}$, $R^{p'}$, $R^{t'}$, $R^{u'}$, $R^v$ and $R^{v'}$ are independently selected from $C_{1-8}$alkylene groups optionally substituted by one or more substituents selected from hydroxy, halogeno, amino, $R^f$, $R^h$, $R^j$, $R^p$ and $R^t$ are independently selected from $C_{2-8}$alkenylene groups optionally substituted by one or more substituents selected from hydroxy, halogeno, amino, and $R^t$ may additionally be a bond; and $R^g$, $R^k$, and $R^u$ are independently selected from by $C_{2-8}$alkynylene groups optionally susbstituted by one or more substituents selected from hydroxy, halogeno or amino.

In many cases, it is preferred that where such groups include a bridging group $R^a$, $R^b$, $R^{b'}$, $R^c$, $R^{c'}$, $R^d$, $R^e$, $R^i$, $R^m$, $R^{m'}R^n$, $R^{n'}$, $R^{p'}$, $R^{t'}$, $R^{u'}$, $R^v$, $R^{v'}R^f$, $R^h$, $R^j$, $R^p$, $R^tR^g$, $R^k$, $R^m$ or $R^u$, said bridging group carries a substituent as defined above, and in particular a hydroxy substituent, in order to block metabolism.

In particular, at least one of $R^1$, $R^2$, $R^3$ or $R^4$ is a group of formula $X^1$—$R^{13}$ where $R^{13}$ is a group as defined in (3"), (5"), (19") or (22"). When said group is a group of formula 3", particularly suitable groups $R^{24}$ are cyclopropyl or any $C_{1-6}$ alkyl group substituted by cyclopropyl. Suitably in said groups, $X^3$ is a group $NR^{29}$ where $R^{29}$ is as defined in 3' above and in particular is hydrogen.

When said group is a group of formula 5", particularly suitable examples are compounds where $R^{36}$ is a saturated 7-membered heterocyclic ring or $R^{36}$ is a 5 or 6 membered heterocyclic ring such a a morpholine, piperidine or tetrahydropyridyl ring, which carries at least one substituent selected from $C_{1-4}$alkanoyl such as acetyl, or —C(O)$NR^{65}R^{66}$,—wherein $R^{65}$ and $R^{66}$ are as defined in (5') above and in particular are hydrogen.

When said group is a group of formula 19", it is preferably an unsubstituted alkynyl group such as prop-2-ynyl.

When said group is a group of formula 22" above, it is suitably a group in which $R^{69}$ is a 5-6-membered saturated heterocyclic group with 1-2 heteroatoms, such as piperidinyl. Suitably $R^{70}$ is hydrogen or $C_{1-3}$alkyl such as methyl. Suitably also, $X^{10}$ is oxygen. $R^v$ and $R^{v'}$ are suitably the same or different and are $C_{1-5}$ alkylene groups in particular $C_{2-3}$alkylene groups.

In one embodiment, at least one of $R^1$, $R^2$, or $R^4$ is a member selected from the group consisting of hydrogen, hydroxy, halogeno, cyano, nitro, trifluoromethyl, $C_{1-3}$alkyl, —$NR^{11}R^{12}$ (wherein $R^{11}$ and $R^{12}$, which may be the same or different, each represents hydrogen or $C_{1-3}$alkyl), or a group $R^{13}$—$X^1$-($CH_2$), wherein x is 0 to 3, $X^1$ represents —O—, —$CH_2$—, —OCO—, carbonyl, —S—, —SO—, —$SO_2$—, —$NR^{14}CO$—, —$CONR^{15}$—, —$SO_2NR^{16}$—, —$NR^{17}SO_2$— or —$NR^{18}$—

(wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups:

1) $C_{1-5}$alkyl which may be unsubstituted or which may be substituted with one or more groups selected from hydroxy, fluoro and amino;
2) $C_{1-5}$alkyl$X^2COR^{19}$ (wherein $X^2$ represents —O— or —$NR^{20}$— (wherein $R^{20}$ represents hydrogen, $C_{1-3}$alkyl or $C_{1-3}$alkoxy$C_{2-3}$alkyl) and $R^{19}$ represents —$NR^{21}R^{22}$— or —$OR^{23}$— (wherein $R^{21}$, $R^{22}$ and $R^{23}$ which may be the same or different each represents hydrogen, $C_{1-3}$alkyl or $C_{1-3}$alkoxy$C_{2-3}$alkyl));
3) $C_{1-5}$alkyl$X^3R^{24}$ (wherein $X^3$ represents —O—, —S—, —SO—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);
5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) $(CH_2)_qX^6R^{37}$ (wherein q is an integer from 0 to 5, $X^6$ represents a direct bond, —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —$CONR^{43}R^e$ and —$NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));
7) $C_{2-6}$alkenyl$R^{36}$ (wherein $R^{36}$ is as defined hereinbefore);
8) $C_{2-6}$alkynyl$R^{36}$ (wherein $R^{36}$ is as defined hereinbefore);
9) $X^7R^{47}$ (wherein $X^7$ is —$SO_2$—, —O— or —$CONR^{48}R^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is —$SO_2$—, $X^1$ is —O—, when $X^7$ is —O—, $X^1$ is carbonyl, when $X^7$ is —$CONR^{48}R^{49}$—, $X^1$ is —O— or $NR^{18}$ (wherein $R^{48}$, $R^{49}$ and $R^{18}$ are as defined hereinbefore);

10) $C_{2-6}$alkenyl$R^{37}$ (wherein $R^{37}$ is as defined hereinbefore);

11) $C_{2-6}$alkynyl$R^{37}$ (wherein $R^{37}$ is as defined hereinbefore);

12) $C_{2-6}$alkenyl$X^8R^{37}$ (wherein $X^8$ represents —O—, —S—, —SO—, —$SO_2$—, —$NR^{50}CO$—, —$CONR^{51}$—, —$SO_2NR^{52}$—, —$NR^{53}SO_2$— or —$NR^{54}$— (wherein $R^{50}$, $R^{51}$, $R^{52}$, $R^{53}$ and $R^{54}$ each independently represents hydrogen, $C_{1-3}$alkyl or $C_{1-3}$alkoxy$C_{2-3}$alkyl) and $R^{37}$ is as defined hereinbefore);

13) $C_{2-6}$alkynyl$X^9R^{37}$ (wherein $X^9$ represents —O—, —S—, —SO—, —$SO_2$—, —$NR^{55}CO$—, —$CONR^{56}$—, —$SO_2NR^{57}$—, —$NR^{58}SO_2$— or —$NR^{59}$— (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R^{37}$ is as defined hereinbefore);

14) $C_{1-3}$alkyl$X^{10}C_{1-3}$alkyl$R^{37}$ (wherein $X^{10}$ represents —O—, —S—, —SO—, —$SO_2$—, —$NR^{60}CO$—, —$CONR^{61}$—, —$SO_2NR^{62}$—, —$NR^{63}SO_2$— or —$NR^{64}$— (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);

15) $R^{36}$ (wherein $R^{36}$ is as defined hereinbefore); and

16) $C_{1-3}$alkyl$X^{10}C_{1-3}$alkyl$R^{36}$ (wherein $X^{10}$ and $R^{36}$ are as defined hereinbefore).

Suitably, $R^1$ and $R^4$ are hydrogen.

Suitably $R^2$ is other than hydrogen and in particular are a group of formula —$X^1$—$R^{13}$ as defined above.

The group $R^2$ may be any of the groups defined above for $R^1$, $R^2$ or $R^4$. Preferably however said other group is a small group such as hydrogen or $C_{1-6}$alkoxy such as methoxy.

A further feature of the invention provides compounds of Formula (I) or compounds of Formula (II) wherein $R^1$, $R^2$ and $R^4$ are selected from hydrogen or groups within the definition of $R^3$ and $R^3$ is selected from a group within the definition of $R^1$, $R^2$ and $R^4$, provided that at least one of $R^1$, $R^2$ and $R^4$ is not hydrogen.

Preferably, $R^5$ is cyano.

Suitable groups Y include oxygen or —NH— and most preferably are —NH—.

In particular, in the compound of Formula (I), n is 0.

Preferably $R^6$ is a group —$R^8$—X—$R^9$—.

Suitably $R^8$ is phenyl.

Suitably X is oxygen or —NH— and most preferably oxygen.

Suitably $R^9$ is a group $R^{10}$ as defined above (where m is 0).

Examples of optional substituents for aryl, carbocyclic or heterocyclic groups $R^{10}$ include one or more groups selected from hydroxy; halo; nitro; cyano; carboxy; $C_{1-6}$alkoxy; $C_{1-6}$alkyl; $C_{2-6}$alkenyl; $C_{2-6}$alkynyl; $C_{2-6}$alkenyloxy; $C_{2-6}$alkynyloxy; $C_{3-6}$cycloalkyl; amino; mono- or di-$C_{1-6}$ alkyl amino; heterocyclyl optionally substituted with $C_{1-6}$alkyl, oxo or $C_{1-6}$alkylthio$C_{1-6}$alkyl; $C(O)R^a$; $C(O)OR^a$; $S(O)_dR^a$; $NR^aC(O)R^b$; $C(O)NR^aS(O)_dR^b$; $C(O)NR^aR^b$; $NR^aC(O)NR^bR^c$; $NR^aS(O)_dR^b$ or $N(S(O)_dR^b)S(O)_dR^c$ where d is 0, 1 or 2 and $R^a$, $R^b$ and $R^c$ are independently selected from hydrogen, $C_{1-6}$alkyl, aryl, $C_{3-6}$cycloalkyl or heterocyclyl, and wherein any alkyl, alkenyl or alkynyl group or moiety contained within the substituent on $R^{10}$ may themselves be optionally substituted with one or more groups selected from hydroxy; cyano; nitro; halo; carboxy; carboalkoxy of 2-7 carbon atoms, $C_{3-6}$cycloalkyl, heterocyclyl optionally substituted with $C_{1-6}$alkyl or oxo; $C(O)R^d$; $C(O)OR^dNR^dR^e$; $S(O)_eR^d$; $NR^dC(O)R^e$; $C(O)NR^dR^e$; $NR^dC(O)NR^eR^f$ or $NR^dS(O)_eR^e$ where e is 0, 1 or 2 and $R^d$, $R^e$ and $R^f$ are independently selected from hydrogen or $C_{1-6}$alkyl optionally substituted with one or more groups selected from hydroxy; cyano; nitro; halo; carboxy; carboalkoxy of 2-7 carbon atoms; $C_{3-6}$cycloalkyl; heterocyclyl optionally substituted with $C_{1-6}$alkyl or oxo; $C(O)R^g$; $C(O)OR^gNR^gR^h$; $S(O)_eR^g$; $NR^hC(O)R^g$; $C(O)NR^gR^h$; $NR^gC(O)NR^hR^i$ or $NR^gS(O)_eR^h$ where e is as defined above and $R^g$, $R^h$ and $R^i$ are independently selected from hydrogen, $C_{1-6}$alkyl or heterocyclyl optionally substituted with $C_{1-6}$alkyl. Alternatively, two substituents on adjacent atoms may be joined to form the second ring of a bicyclic ring system wherein the said second ring is optionally substituted with one or more of the groups listed above for $R^{10}$ and optionally contains one or more heteroatoms.

In some embodiments, the substituent on the group $R^{10}$ is a complex chain. Thus, for example, a substituent may comprise a substituted alkyl chain which is optionally interposed with heteroatoms such as groups of sub-formula (i)

$$—X^a—R^{70}—(X^b—R^{71})_q—(X^c)_s—R^{72} \quad (i)$$

wherein $X^a$, $X^b$ and $X^c$ are independently selected from any of the groups listed above for $X^1$, $R^{70}$ and $R^{71}$ are independently selected from $C_{1-6}$alkylene, $C_{2-6}$alkenylene or $C_{2-6}$alkynylene groups any of which may be optionally substituted with hydroxy; cyano; nitro; halo; carboxy, carboalkoxy of 2-7 carbon atoms or $C_{3-6}$cycloalkyl;

$R^{72}$ is hydrogen or an $C_{1-6}$alkyl, $C_{2-6}$ alkenyl or $C_{2-6}$alkynyl group any of which may be optionally substituted with hydroxy; cyano; nitro; halo; carboxy; $C_{3-6}$cycloalkyl and in particular cyclopropyl; or an optionally substituted heterocyclic group, in particular a group as defined above for $R^{36}$, and q and s are independently 0 or 1.

A further example of a substituent on $R^{10}$ is a group of the sub-formula (ii)

$$—Z—(CH_2)_pR^{100}—R^{101} \quad (ii)$$

wherein

—Z— is a direct bond or a group of sub-formula (iii)

$$—X^{121}—R^{751}—X^{131}—(R^{761}—X^{141})_s—(R^{771}—X^{151})_{s'}— \quad (iii)$$

wherein $X^{121}$, $X^{131}$ each $X^{141}$ and each $X^{151}$ are independently selected from —O—, —C(O)—, —C(O)O—, —S—, —SO—, —$SO_2$—, —$NR^{780}C(O)$—, —$NR^{781}C(O)O$—, —$CONR^{791}$—, —C(O)$ONR^{791}$—, —$SO_2NR^{801}$—, —$NR^{811}SO_2$— or —$NR^{821}$— (wherein $R^{781}$, $R^{791}$, $R^{801}$, $R^{811}$ and $R^{821}$ each independently represents hydrogen, $C_{1-3}$alkyl optionally substituted by hydroxy, or $C_{1-3}$alkoxy$C_{2-3}$ alkyl) and each $X^{131}$, $X^{141}$ and $X^{151}$ may additionally be a direct bond;

s and s' is 0, 1, 2 or, 3;

$R^{711}R^{761}$ and $R^{771}$ are independently selected from $C_{1-6}$alkylene, $C_{2-6}$alkenylene or $C_{2-6}$alkynylene optionally substituted by halo and hydroxy or $R^{751}$, $R^{761}$ and $R^{771}$ can each independently be direct bonds;

$R^{100}$ is an optionally substituted divalent heterocyclic group, $C_{1-5}$alkylene, or divalent $C_{3-7}$cycloalkyl, $R^{101}$ is hydrogen, amino or a group of sub-formula (iv)

$$—X^{161}R^{8131}—(X^{171}R^{841})_t—X^{181}R^{851} \quad (iv)$$

wherein $X^{161}$, $X^{181}$ and each $X^{171}$ are each independently selected from a direct bond, —O—, —C(O)—, —S—, —SO—, —$SO_2$—, —$NR^{861}C(O)$—, —$NR^{861}C(O)O$—, —$CONR^{871}$—, —$C(O)ONR^{871}$—, —$SO_2NR^{881}$—, —$NR^{891}SO_2$— or —$NR^{901}$— (wherein $R^{861}$, $R^{871}$, $R^{881}$, $R^{891}$ and $R^{901}$ each independently represents hydrogen, $C_{1-3}$alkyl or $C_{1-3}$alkoxy$C_{2-3}$alkyl), $R^{831}$ and each $R^{841}$ are independently selected from $C_{1-6}$alkylene, $C_{2-6}$alkenylene or $C_{2-6}$alkynylene, $R^{851}$ is selected from hydrogen, $C_{1-6}$alkyl, $C_{2-6}$alkenyl or $C_{2-6}$alkynyl, and t is 0, 1, 2 or 3.

p is 0, 1, 2 or 3

In some embodiments, $R^{10}$ is a heterocyclic ring containing one or 2 oxygen atoms. Particular examples of groups $R^{10}$ include phenyl or cycloalkyl of from 3-8 and preferably of 6 carbon atoms which are substituted at the alpha position. Preferably however, $R^{10}$ is substituted phenyl.

Preferably $R^{10}$ is a substituted with an optionally substituted alkoxy group wherein substituents are as described above. For example $R^{10}$ is phenyl substituted at the alpha (ortho position) by methoxy, —$OCH_2(C(O)NHCH_2)_fC(O)NH(R^{73})$, where f is 0 or 1, and $R^{73}$ is $C_{1-4}$ alkyl such as methyl or $C_{3-6}$cycloalkyl such as cyclopropyl.

Examples of heterocyclic rings $R^{10}$ include 3-7 membered rings, up to two of which may be oxygen atoms. Such groups include:

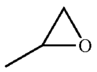
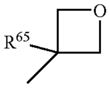
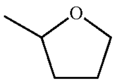
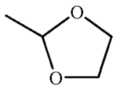
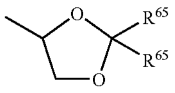
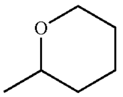
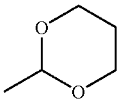
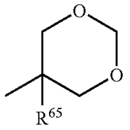

where each $R^{65}$ is independently selected from hydrogen or $C_{1-6}$alkyl and especially methyl. In such compounds, m in $R^9$ is suitably 1, 2 or 3.

Other examples of heterocyclic groups $R^{10}$ include pyridyl, thiazolyl, pyrazinyl, pyrimidinyl, oxadiazole.

Particular examples of groups $R^{10}$ include divalent phenyl, pyridyl or $C_{3-8}$cycloalkyl. Most preferably however, $R^{65}$ is optionally substituted phenylene. $R^{100}$ is preferably a group selected from a divalent $C_{1-2}$ alkylene, or divalent $C_{3-4}$ cycloalkyl, pyridyl, or pyrrolidinyl or phenylene.

In a preferred embodiment $R^8$ and $R^{10}$ are both phenylene; Y is —NH and X is oxygen; and n, m and p are all 0.

Preferably $R^{101}$ is hydrogen, Suitable further substituents for $R^{100}$ and $R^{10}$ include those listed above for pyridyl, pyrimidinyl and phenyl groups $R^8$. A particularly preferred substituent for $R^{10}$ is fluoro.

Suitable examples of variables within sub-formula (i) defined above are as follows:

$X^{12}$ is suitably —O—;

$R^{75}$ is suitably $C_{1-6}$alkylene and preferably the group —$C(R^AR^B)$ where $R^A$ and $R^B$ are each independently selected from $C_{1-3}$ alkyl, $C_{2-3}$ alkenyl, $C_{2-3}$ alkynyl and halo, most preferably both either $C_1$ alkyl or fluoro.

$R^{76}$ and $R^{77}$ are suitably the same or different and are preferably independently selected from $C_{1-6}$alkylene and in particular methylene groups and a direct bond. Most preferably $R^{77}$ is a direct bond.

$X^{13}$ is preferably the group —$CONR^{79}$— or —$NR^{78}C(O)$—, most preferably the group —$CONR^{79}$—, where $R^{78}$ and $R^{79}$ are selected from hydrogen or $C_{2-3}$ alkyl and are more preferably hydrogen;

$X^{14}$ is suitably —C(O)—, —$CONR^{79}$—, where $R^{78}$ and $R^{79}$ are selected from hydrogen or $C_{1-3}$ alkyl and are preferably hydrogen, or a direct bond;

s, q and p are all preferably 0.

Where Z is a group of sub-formula (i), a particularly preferred group is selected from

—O—$C(CH_3)_2$—$CONR^{791}$—

—O—$C(F)_2$—

—O—$C(CH_3)_2$—$CONR^{791}$—$CH_2$—$CONR^{791}$—

—O—$C(CH_3)_2$—$CONR^{791}$—$CH_2$—$CONR^{791}$—$(CH_2)_2$—$NR^{821}$—

—O—$C(F)_2$—$CONR^{791}$—

—O—$C(F)_2$—$CONR^{791}$—$CH_2$—$CONR^{791}$

—O—$C(CH_3)_2$—$CONR^{791}$—$CH_2$—$NR^{821}$—

—O—$C(CH_3)_2$—$CONR^{791}$—$(CH_2)_2$—$SO_2$—

—O—$C(CH_3)_2$—$CONR^{791}$—$(CH_2)_2$—S—

—O—$C(CH_3)_2$—$CONR^{791}$—$(CH_2)_2$—O— where $R^{791}$, $R^{821}$ are preferably as hereinbefore defined and preferably are methyl or hydrogen, most preferably hydrogen.

Alternatively Z is preferably a direct bond.

Examples of suitable heterocyclic groups $R^{100}$ are 5- or 6-membered aromatic or non-aromatic rings which contain up to 4 and preferably up to 3 heteroatoms. A particular example of a non-aromatic group $R^{100}$ is piperazine or morpholine or piperidine linked via carbon or nitrogen but preferably by nitrogen atoms whilst an example of an aromatic group is oxadiazole.

Where Z is a group of sub-formula (iii), $R^{100}$ may be substituted by a simple $C_{1-6}$alkyl group such as methyl. However, where Z is a direct bond, more complex substituents are required to be present on the ring $R^{100}$. In such instances, at least one group $X^{161}$, $X^{171}$ or $X^{181}$, and preferably at least $X^{181}$, in the group of sub-formula (Iv) is other than a direct bond. Preferably, at least one such group, and most preferably $X^{181}$ is —S—, —S(O)— or —$S(O)_2$—.

Suitable further substituents for $R^{10}$ include those listed above for pyridyl, pyrimidinyl and phenyl groups $R^6$.

A preferred sub-group of compounds of the invention comprise composed of Formula (1) or Formula (Ia) wherein:

$R^1$ and $R^4$ are each hydrogen;

$R^2$ is $C_{1-5}$alkoxy;

$R^3$ is selected from group (i) or group (ii);

$R^5$ is cyano;

Y is —NH—;

n is 0;

$R^6$ is a group of the formula —$R^8$—X—$R^9$;

$R^8$ is a divalent phenyl ring, optionally substituted by halogeno, preferably fluoro;

X is —O—;

$R^9$ is a group $(CH_2)_mR^{10}$;

m is 0; and $R^{10}$ is optionally substituted phenyl;

or pharmaceutical-acceptable salts, pro-drugs or solvate thereof.

A further preferred sub-group of compounds of Formula (I) are compounds of Formula (II)

(II)

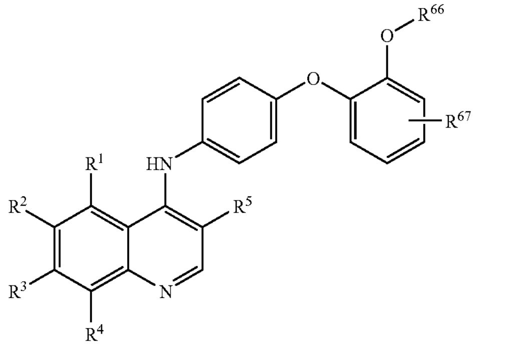

where $R^1$, $R^2$, $R^3$, $R^4$ and $R^5$ are as defined above and $R^{66}$ is optionally substituted $C_{1-6}$alkyl in particular methyl and $R^{67}$ is selected from hydrogen, halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkyl amino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino.

Suitably $R^{66}$ is $C_{1-6}$ alkyl such as methyl. Preferably however it is a substituted $C_{1-4}$ alkyl group, wherein the substitutents are selected from hydroxy, $NR^dR^c$, $S(O)_eR^d$, $NR^dC(O)R^e$; $C(O)NR^dR^e$; $NR^dC(O)NR^eR^f$; $NR^dS(O)_eR^e$ where e, $R^d$, $R^e$ and $R^f$ are as defined above.

In particular, $R^{66}$ is a group $—CH_2(C(O)NHCH_2)_pC(O)NH(R^{73})$, where p and $R^{73}$ are as defined above.

Preferably $R^{67}$ is hydrogen.

A further group of compounds according to the invention are compounds of Formula (III)

(III)

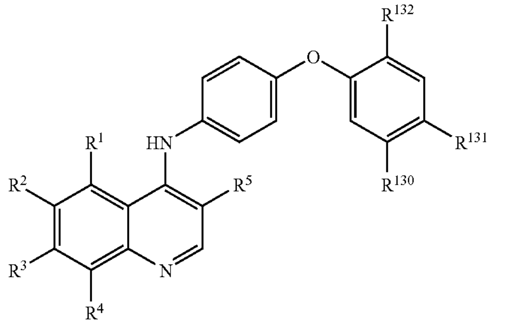

wherein $R^{130}$ is a group of formula (i) as hereinbefore defined and preferably is selected from: $—NR^{78}C(O)—R^9—R^6$, $—NR^{82}—R^{100}—R^{101}$; and $C_{1-4}$ alkoxyl; hydrogen or halo, particularly fluoro, where $R^{78}$, $R^{82}$, $R^{100}$ and $R^{101}$ are as hereinbefore defined;

$R^{131}$ is a hydrogen or halo, particularly fluoro; and $R^{132}$ is a $C_{1-4}$ alkoxy and pharmaceutical-acceptable salts, pro-drugs or solvate thereof.

A preferred group of compounds of the invention comprises

7-[3-(4,4-difluoropiperidin-1-yl)propoxy]-6-methoxy-4-{[3-(2-methoxyphenoxy)phenyl]amino}quinoline-3-carbonitrile;

7-[3-(4-isopropylpiperazin-1-yl)propoxy]-6-methoxy-4-{[3-(2-methoxyphenoxy)phenyl]amino}quinoline-3-carbonitrile;

7-[3-(3,3-difluoropyrrolidin-1-yl)propoxy]-6-methoxy-4-{[3-(2-methoxyphenoxy)phenyl]amino}quinoline-3-carbonitrile;

7-[3-(1,1-dioxidothiomorpholin-4-yl)propoxy]-6-methoxy-4-{[4-(2-methoxyphenoxy)phenyl]amino}quinoline-3-carbonitrile;

6-methoxy-4-{[4-(2-methoxyphenoxy)phenyl]amino}-7-(3-morpholin-4-yl-2-oxopropoxy)quinoline-3-carbonitrile;

6-methoxy-4-{[4-(2-methoxyphenoxy)phenyl]amino}-7-(2-oxo-3-pyrrolidin-1-ylpropoxy)quinoline-3-carbonitrile;

7-[3-(2,6-dimethylpiperidin-1-yl)-2-oxopropoxy]-6-methoxy-4-{[4-(2-methoxyphenoxy)phenyl]amino}quinoline-3-carbonitrile; and 7-{3-[(1,1-dioxidotetrahydrothien-3-yl)(methyl)amino]propoxy}-6-methoxy-4-{[4-(2-methoxyphenoxy)phenyl]amino}quinoline-3-carbonitrile and pharmaceutical-acceptable salts, pro-drugs or solvate thereof.

A further preferred group of compounds of the invention comprises 7-(3-azetidin-1-yl-2-oxopropoxy)-6-methoxy-4-{[4-(2-methoxyphenoxy)phenyl]amino}quinoline-3-carbonitrile;

7-{3-[4-(ethylsulfonyl)piperazin-1-yl]propoxy}-6-methoxy-4-{[4-(2-methoxyphenoxy)phenyl]amino}quinoline-3-carbonitrile;

6-methoxy-7-{3-[4-(2-methoxyethyl)piperazin-1-yl]propoxy}-4-{[4-(2-methoxyphenoxy)phenyl]amino}quinoline-3-carbonitrile;

6-methoxy-4-{[4-(2-methoxyphenoxy)phenyl]amino}-7-{3-[3-(methylsulfonyl)pyrrolidin-1-yl]propoxy}quinoline-3-carbonitrile; and 7-[3-(4-acetylpiperazin-1-yl)propoxy]-6-methoxy-4-{[4-(2-methoxyphenoxy)phenyl]amino}quinoline-3-carbonitrile;

7-{3-[bis(2-hydroxyethyl)amino]propoxy}-6-methoxy-4-{[4-(2-methoxyphenoxy)phenyl]amino}quinoline-3-carbonitrile;

7-[3-(cyclopropylamino)propoxy]-4-{[2-fluoro-4-(1,3-thiazol-2-yloxy)phenyl]amino}-6-methoxyquinoline-3-carbonitrile;

7-[3-(cyclopropylamino)propoxy]-4-{[2-fluoro-4-(isothiazol-3-yloxy)phenyl]amino}-6-methoxyquinoline-3-carbonitrile;

2-{2-[4-({3-cyano-7-[3-(cyclopropylamino)propoxy]-6-methoxyquinolin-4-yl}amino)phenoxy]phenoxy}-N-methylacetamide; and 7-[3-(cyclopropylamino)propoxy]-6-methoxy-4-{[4-(2-methoxyphenoxy)phenyl]amino}quinoline-3-carbonitrile;

and pharmaceutical-acceptable salts, pro-drugs or solvate thereof.

Particular examples of compounds of Formula (I) or Formula (Ia) are listed in Tables 1, 2, 3 and 4.

TABLE 1

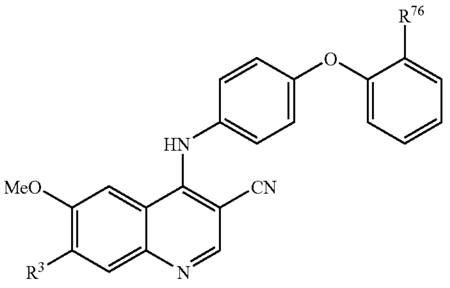

| Compd. No. | $R^3$ | $R^{76}$ |
|---|---|---|
| 1 | 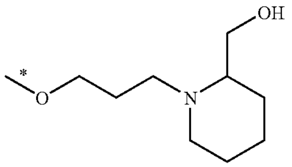 | $OCH_3$ |
| 2 | 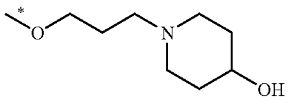 | $OCH_3$ |
| 3 | $O(CH_2)_3NH(CH_2)_2OH$ | $OCH_3$ |
| 4 | 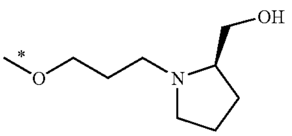 | $OCH_3$ |
| 5 | 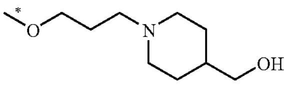 | $OCH_3$ |
| 6 | $O(CH_2)_3N(CH_3)(CH_2)_2OH$ | $OCH_3$ |
| 7 | 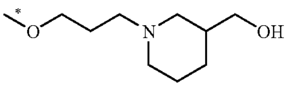 | $OCH_3$ |

TABLE 1-continued

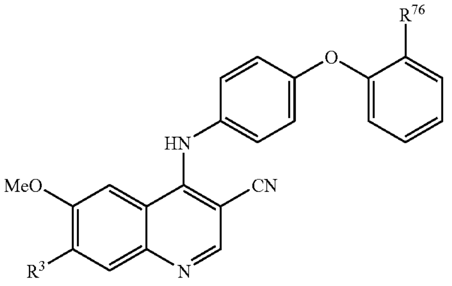

| Compd. No. | $R^3$ | $R^{76}$ |
|---|---|---|
| 8 | 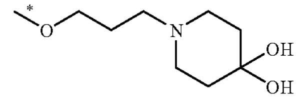 | $OCH_3$ |
| 9 | 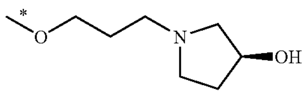 | $OCH_3$ |
| 10 | 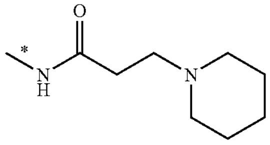 | 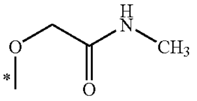 |
| 11 | 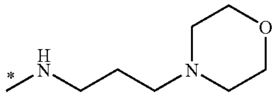 | 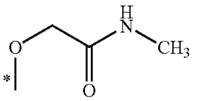 |
| 12 | 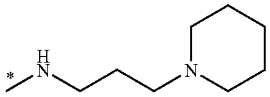 | 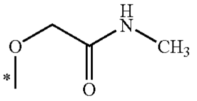 |
| 13 | 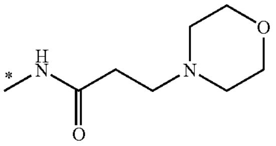 | 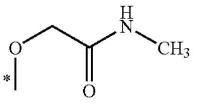 |
| 14 | 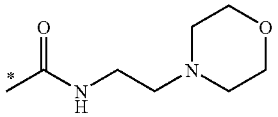 | $OCH_3$ |
| 15 | $O(CH_2)_3NH(CH_2)_2SCH_3$ | $OCH_3$ |
| 16 | 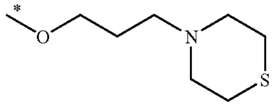 | $OCH_3$ |
| 17 | 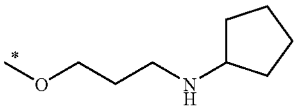 | 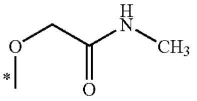 |

TABLE 2
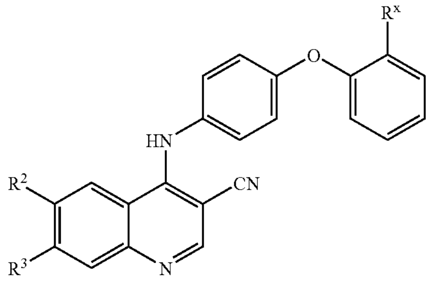
| Compd. No. | $R^2$ | $R^3$ | $R^x$ |
|---|---|---|---|
| 18 | $OCH_3$ | 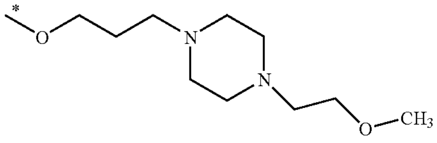 | $OCH_3$ |
| 19 | $OCH_3$ | 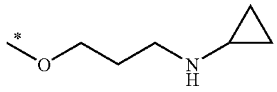 | $OCH_2C(O)NHCH_3$ |
| 20 | $OCH_2C{\equiv}CH$ | $OCH_3$ | 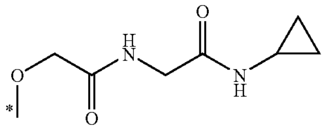 |
| 21 | $OCH_3$ | 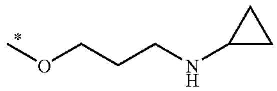 | $OCH_3$ |
| 22 | $OCH_3$ | 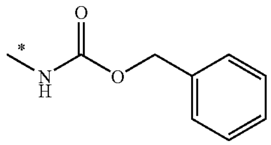 | $OCH_2C(O)NHCH_3$ |
| 23 | $OCH_3$ | 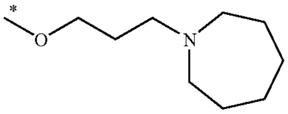 | $OCH_3$ |
| 24 | $OCH_3$ | 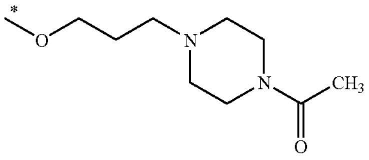 | $OCH_3$ |
| 25 | $OCH_3$ | 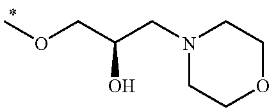 | $OCH_3$ |
| 26 | $OCH_3$ | 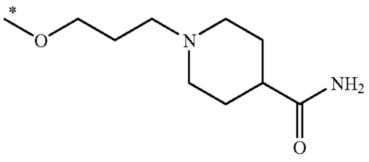 | $OCH_3$ |

TABLE 2-continued
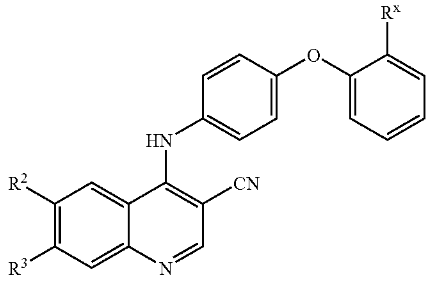
| Compd. No. | $R^2$ | $R^3$ | $R^x$ |
| --- | --- | --- | --- |
| 27 | $OCH_2C{\equiv}CH$ | $OCH_3$ | 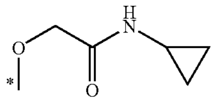 |
| 28 | $OCH_2C{\equiv}CH$ | 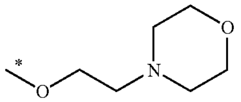 | 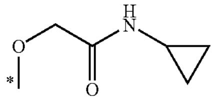 |
| 29 | $OCH_3$ | 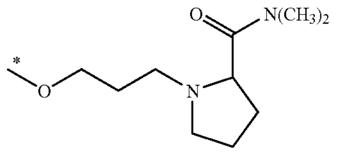 | $OCH_3$ |
| 30 | $OCH_3$ | $OCH_2CH(OH)CH_2N(CH_3)_2$ | $OCH_3$ |
| 31 | $OCH_3$ | 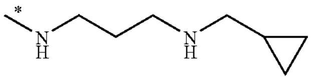 | $OCH_2C(O)NHCH_3$ |
| 32 | $OCH_3$ | 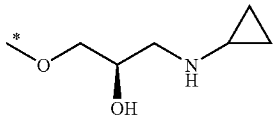 | $OCH_3$ |
| 33 | $OCH_3$ | 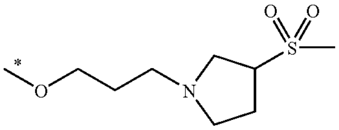 | $OCH_3$ |
| 34 | $OCH_3$ | 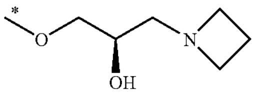 | $OCH_3$ |
| 35 | $OCH_3$ | 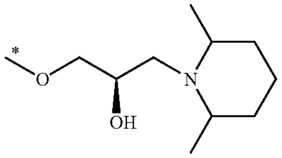 | $OCH_3$ |
| 36 | $OCH_3$ | 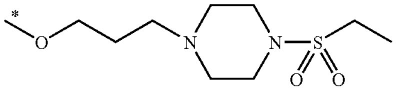 | $OCH_3$ |

TABLE 2-continued
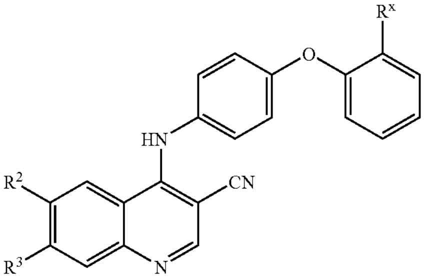
| Compd. No. | $R^2$ | $R^3$ | $R^x$ |
|---|---|---|---|
| 37 | $OCH_3$ | 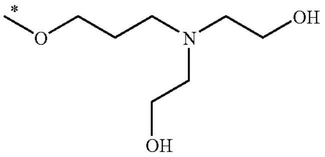 | $OCH_3$ |
| 38 | $OCH_3$ | 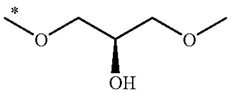 | $OCH_3$ |
| 39 | $OCH_3$ | 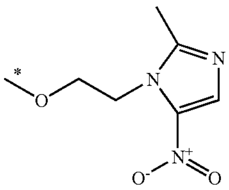 | $OCH_3$ |
TABLE 3
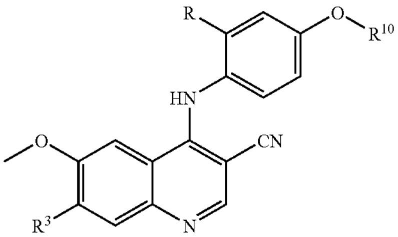
| Compd. No. | $R^3$ | R | $R^{10}$ |
|---|---|---|---|
| 40 | 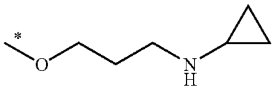 | F | 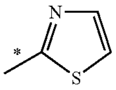 |
TABLE 3-continued
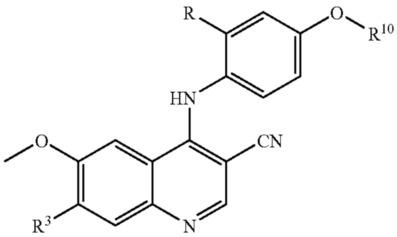
| Compd. No. | $R^3$ | R | $R^{10}$ |
|---|---|---|---|
| 41 | 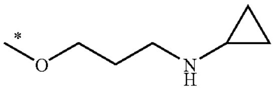 | H | 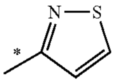 |

TABLE 4
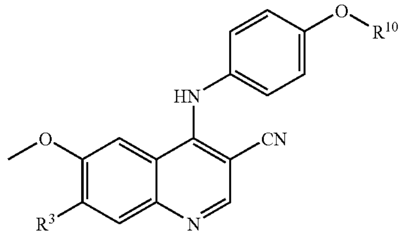
| Compd. No. | $R^3$ | $R^{10}$ |
|---|---|---|
| 42 | 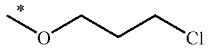 | 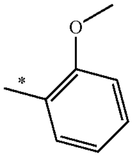 |
| 43 | 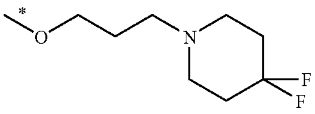 | 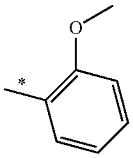 |
| 44 | 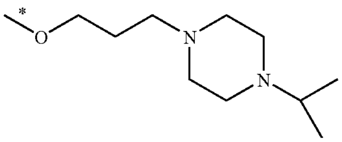 | 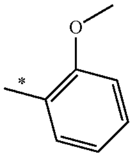 |
| 45 | 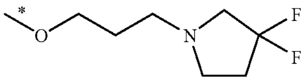 | 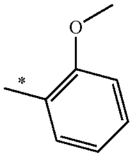 |
| 46 | 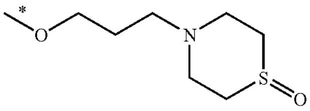 | 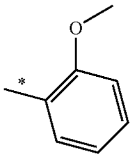 |
| 47 | 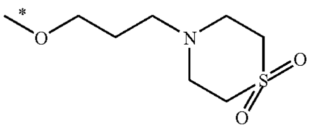 | 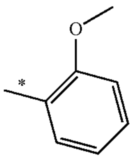 |
| 48 | 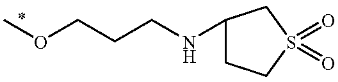 | 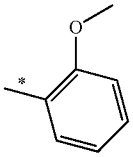 |
TABLE 4-continued
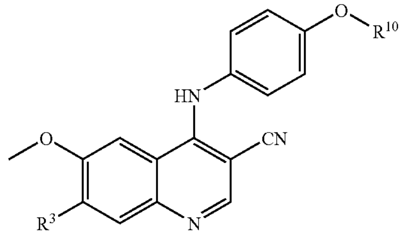
| Compd. No. | $R^3$ | $R^{10}$ |
|---|---|---|
| 49 | 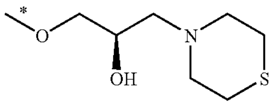 | 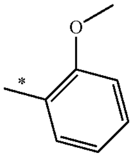 |
| 50 | 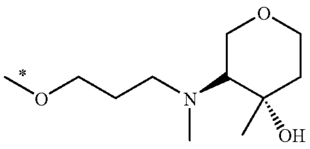 | 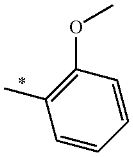 |
| 51 | 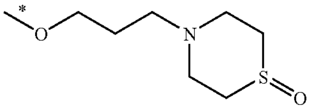 | 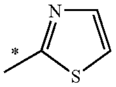 |
| 52 | 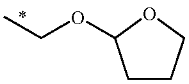 | 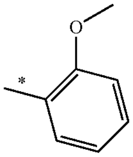 |
| 53 | 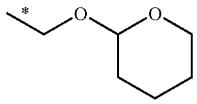 | 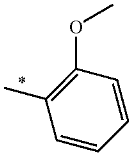 |
| 54 | 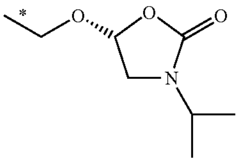 | 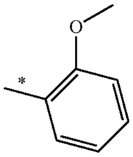 |
| 55 | 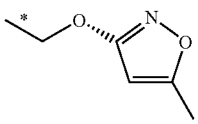 | 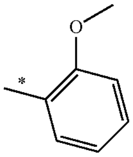 |
| 56 | 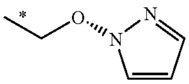 | 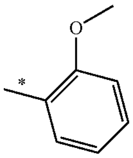 |

TABLE 4-continued

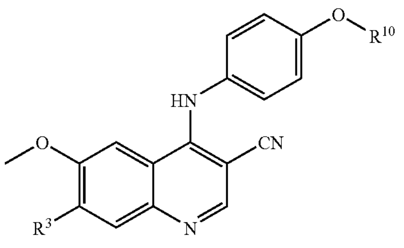

| Compd. No. | $R^3$ | $R^{10}$ |
|---|---|---|
| 57 | 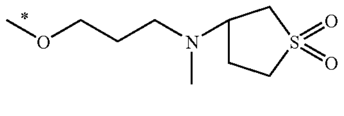 | 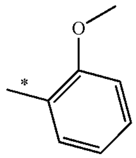 |
| 58 | 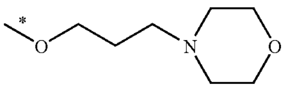 | 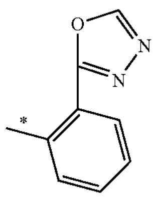 |
| 59 | 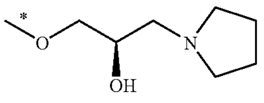 | 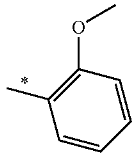 |
| 60 | $—O—CH_2—CN$ | 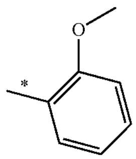 |
| 61 | 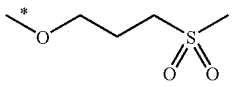 | 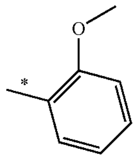 |
| 62 | 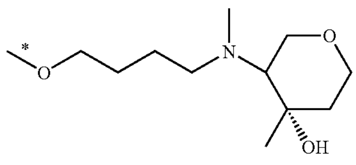 | 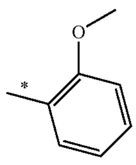 |

TABLE 5

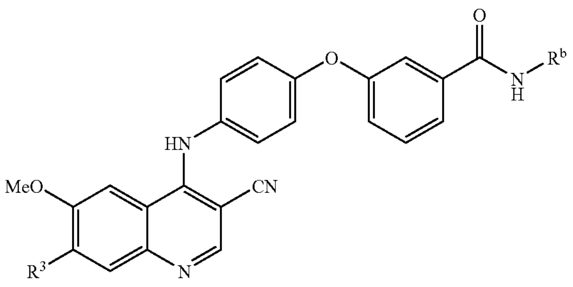

| Compd No. | $R^3$ | $R^b$ |
|---|---|---|
| 63 | 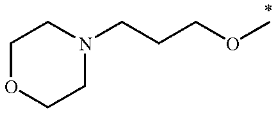 | H |

TABLE 6

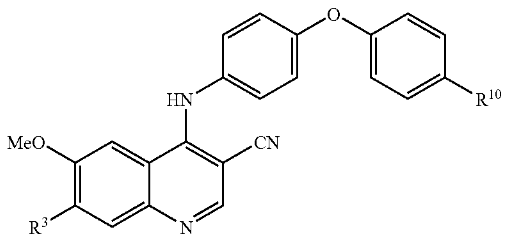

| Compd No. | $R^3$ | $R^{10}$ |
|---|---|---|
| 64 | 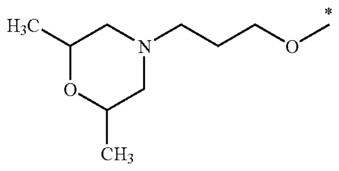 | $OCH_2C(O)NHCH_3$ |

Compounds of Formula (I) are suitably prepared by reacting a compound of formula (III)

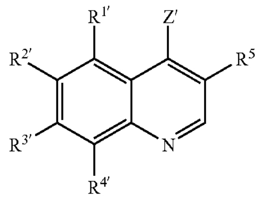

(III)

where $R^{1'}$, $R^{2'}$, $R^{3'}$, $R^{4'}$ represent $R^1$, $R^2$, $R^3$ and $R^4$ respectively as defined in relation to Formula (I) or a precursor thereof, $R^5$ is as defined in relation to Formula (I) and Z' is a leaving group, with a compound of Formula (IV)

$$H—Y(CH_2)_nR^{6'} \qquad (IV)$$

where Y, and n are as defined in relation to Formula (I), and $R^{6'}$ is a group $R^6$ as defined in relation to Formula (I) or a precursor thereof, and thereafter if necessary or desired converting precursor groups $R^{1'}$, $R^{2'}$, $R^{3'}$, $R^{4'}$ and $R^{6'}$ to groups of formula $R^1$, $R^2$, $R^3$, $R^4$ and $R^6$ respectively, or converting a group $R^1$, $R^2$, $R^3$, $R^4$ and $R^6$ to a different such group.

Suitable leaving groups for Z' include halogen such as bromo or chloro, or a mesylate or tosylate group or a substituted phenoxy group.

The reaction is suitably carried out in an organic solvent such as an alcohol for example propanol or cyclohexanol at elevated temperatures, for example of from 50 to 150° C., for example at about 105° C.

Conversion reactions in which precursor groups $R^{1'}$, $R^{2'}$, $R^{3'}$, $R^{4'}$ are converted to groups of formula $R^1$, $R^2$, $R^3$ and $R^4$ respectively, or groups $R^1$, $R^2$, $R^3$ and $R^4$ are converted to different such group can be carried out using conventional chemistry as outlined hereinafter. Particular precursor groups $R^{1'}$, $R^{2'}$, $R^{3'}$, $R^{4'}$ are groups of formula $R^{13'}—X^1—(CH_2)_x$ wherein x and $X^1$ are as defined herein, and $R^{13'}$ is $C_{1-5}$alkyl which is substituted with halo other than fluoro, and in particular chloro or bromo. The chloro or bromo group may readily be converted into many other groups $R^{13}$ as defined in relation to claim 1."

Similarly conversion reactions involving groups $R^6$ may be effected using conventional chemistry. For example substituent groups on a group $R^{10}$ within the group $R^6$ may be changed, for example by changing acids to esters or amides etc. Alternatively, compounds of Formula (I) where $R^6$ is a group $—R^8—X—R^9$ are prepared by reacting a compound of Formula (V)

(V)

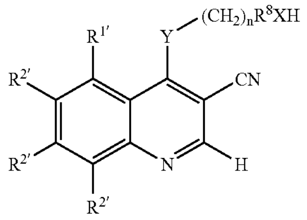

where $R^{1'}$, $R^{2'}$, $R^{3'}$, $R^{4'}$ are as defined in relation to Formula (III) $R^8$, X, Y and n are as defined in relation to Formula (I), with a compound of Formula (VI)

$$—R^{9'}\text{-}Z'' \qquad (VI)$$

where $R^{9'}$ is a group $R^9$ as defined in relation to Formula (I) or a precursor thereof and Z" is a leaving group;

and thereafter if necessary or desired converting precursor groups $R^{1'}$, $R^{2'}$, $R^{3'}$, $R^{4'}$ and $R^{9'}$ to groups of formula $R^1$, $R^2$, $R^3$, $R^4$ and $R^9$ respectively, or converting a group $R^1$, $R^2$, $R^3$, $R^4$ and $R^9$ to a different such group. Suitable leaving groups for Z" include halogen such a bromo or chloro, or a mesylate or tosylate group.

The reaction is suitably carried out in an organic solvent such as DMF at elevated temperatures, for example of from 40 to 120° C., for example at about 80° C. Conversion reactions are conventional and can be derived from literature information.

Compounds of Formula (III) and (V) are either known compounds or they can be prepared from known compounds by conventional methods, for example as described in WO 98/43960 and WO 98/13350.

Compounds of Formula (IV) are also known compounds (see for example Rev. Chim. (Bucharest) (1988), 39(6), 477-82 and DD 110651: 74.01.05) or they can be prepared from known compounds using conventional methods. For example, where Y is NH, compounds of Formula (IV) are suitably prepared by reduction of a compound of formula (VII)

$$O_2N(CH_2)_nR^8XR^{9'} \qquad (VII)$$

where X, $R^8$, $R^{9'}$ and n are as defined above. It may be convenient to convert precursor groups $R^{9'}$ to groups $R^9$ or groups $R^9$ to other such groups at the level of compound of Formula (VII) or (IV) using conventional chemistry.

Compounds of Formula (VI) are also known compounds or they can be prepared from known compounds by conventional methods.

Compounds of the invention are useful in the inhibition of MEK enzyme activity and can be used in the treatment of proliferative disease. They will suitably be in the form of a pharmaceutical composition, in combination with a pharmaceutically acceptable carrier. Such compositions form a further aspect of the invention.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above.

Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, and esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects MEK enzymes.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

In a further aspect, the invention provides a method of treating proliferative disease by administering a compound of Formula (I) as described above, or a pharmaceutical composition as described above.

Yet a further aspect of the invention provides the use of a compound of Formula (I) as defined above, in the preparation of a medicament for use in the inhibition of MEK enzyme activitiy and in particular for the treatment of proliferative disease such as cancer.

According to a further aspect of the invention there is provided a compound of the Formula (I), Formula (Ia), Formula (II) or Formula (III) or a pharmaceutically-acceptable salt or prodrug or solvate thereof, as defined hereinbefore, for use in a method of treatment of the human or animal body by therapy.

We have found that the compounds of the present invention possess potent anti-tumour activity which it is believed is obtained by way of inhibition the MAPK pathway and, in particular, inhibition of MEK enzyme Accordingly the compounds of the present invention are of value as anti-proliferative agents.

Thus according to this aspect of the invention there is provided the use of a compound of Formula (I), Formula (Ia), Formula (II) or Formula (III) or a pharmaceutically-acceptable salt, prodrug or solvate thereof, as defined hereinbefore in the manufacture of a medicament for use as an anti-proliferative agent in the containment and/or treatment of solid tumour disease.

According to a further feature of this aspect of the invention there is provided a method for producing an anti-proliferative effect by the containment and/or treatment of solid tumour disease in a warm-blooded animal, such as man, in need of such treatment which comprises administering to said animal an effective amount of a compound of Formula (I), Formula (Ia), Formula (II) or Formula (III) or a pharmaceutically-acceptable salt thereof, prodrug or solvate thereof as defined hereinbefore.

According to a further aspect of the invention there is provided the use of a compound of Formula (I), Formula (Ia), Formula (II) or Formula (III) or a pharmaceutically-acceptable salt thereof, prodrug or solvate thereof as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a compound of Formula (I), Formula (Ia), Formula (II) or Formula (III) or a pharmaceutically-acceptable salt thereof, prodrug or solvate thereof as defined hereinbefore.

According to a further aspect of the invention there is provided the use of a compound of Formula (I), Formula (Ia), Formula (II) or Formula (III) or a pharmaceutically-acceptable salt thereof, prodrug or solvate thereof as defined hereinbefore in the manufacture of a medicament for use in the prevention or treatment of those tumours which are sensitive to inhibition of MEK enzymes.

According to a further feature of this aspect of the invention there is provided a method for the prevention or treatment of those tumours which are sensitive to inhibition of MEK enzymes which comprises administering to said animal an effective amount of a compound of Formula (I), Formula (Ia) Formula (II) or Formula (III) or a pharmaceutically-acceptable salt thereof, prodrug or solvate thereof as defined hereinbefore.

The anti-proliferative treatment defined hereinbefore may be applied as a sole therapy or may involve, in addition to the compounds of the invention, conventional surgery or radiotherapy or chemotherapy. Such chemotherapy may include one or more of the following categories of anti-tumour agents:—

(i) anti-invasion agents (for example metalloproteinase inhibitors like marimastat and inhibitors of urokinase plasminogen activator receptor function);

(ii) other antiproliferative or antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl)amino]benzamido}-4-(tetrazol-5-yl) butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD 1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family; and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a compound of Formula (I) or Formula (Ia) or a pharmaceutically-acceptable salt thereof, prodrug or solvate thereof as defined hereinbefore and an additional anti-tumour agent as defined hereinbefore for the conjoint treatment of cancer.

Although the compounds of the present invention are primarily of value as therapeutic agents for use in warm-blooded animals (including man), they are also useful whenever it is required to inhibit the effects of MEK enzyme. Thus, they are useful as pharmacological standards for use in the development of new biological tests and in the search for new pharmacological agents.

The invention will now be particularly described by way of example.

EXAMPLES

In the examples the following abbreviations have been used.

DMF N,N-dimethylformamide
THF tetrahydrofuran
DMSO dimethyl acetamide
DEAD diethyl azodicarboxylate
Ph3 P triphenylphosphine
EDC ethylene dichloride (1,2-dichloroethane)
DCM dichloromethane (methylenechloride)
DMAP dimethylaminepyridine
HOBT N-hydroxybenzotriazole
EDAC 1-(3-dimethylaminopropyl)-3-ethyl-carbodiimide
KHMDS potassium hexamethyldisilazane (potassium bis(trimethylsilyl)amide)

Preparation of Key Intermediates

Preparation A

Chloroquinoline Intermediates

These can be prepared for example using the following scheme where "Bz" represents benzyl.

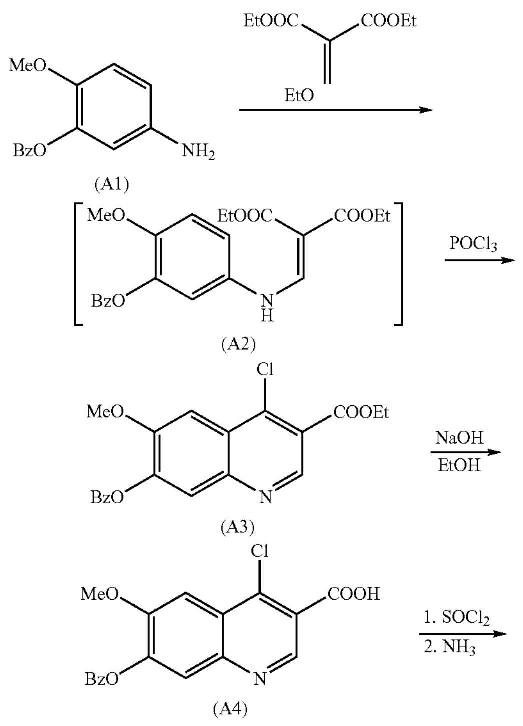

(A1) (A2) (A3) (A4)

-continued

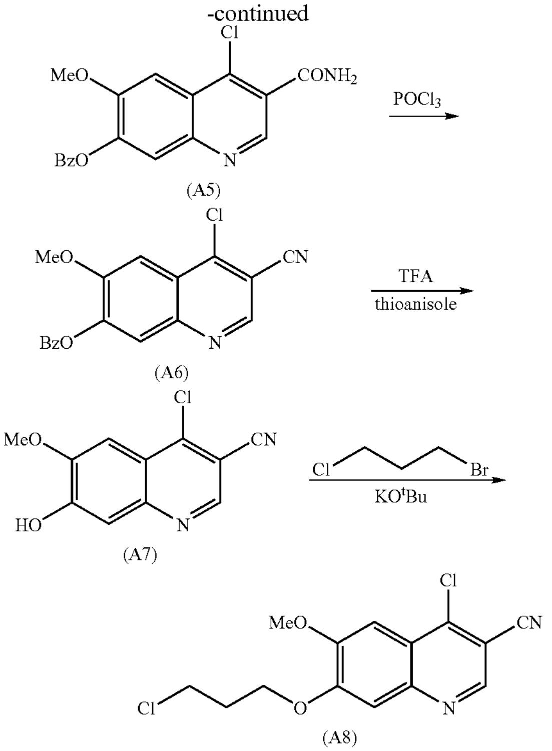

(A5) (A6) (A7) (A8)

A mixture of (A1) (10.36 g., 45.3 mmole) and diethylethoxymethylene malonate (9 mL, 45.3 mmole) was heated at 110° C. for 1 hour and then allowed to cool overnight. The mixture was evaporated and the product (A2) used in the next step without further purification.

Mass Spectrum m/e 400 ($M^+$+H).

Preparation of (A3)

A mixture of (A2) (assumed 45.3 mmole) and phosphoryl chloride (83.3 mL, 906 mmole) was heated at 115° C. for 18 hours. After cooling, the solution was evaporated to remove excess phosphoryl chloride. The residue was treated with ice and aqueous ammonia to hydrolyse the remaining phosphoryl chloride. The solid product was filtered off and dried in a vacuum oven to give a cream coloured solid, 9.0 g (53% yield).

Mass Spectrum m/e 372 ($M^+$+H).

Preparation of (A4)

A mixture of (A3) (9.0 g, 24.2 mmole) was stirred in ethanol (48.3 mL) for 15 minutes at ambient temperature to give a smooth suspension. Aqueous sodium hydroxide solution (2.0M, 48.3 mL, 96.7 mmole) was added and the mixture stirred for 18 hours at ambient temperature. The ethanol was removed by rotary evaporation and the resulting solution was acidified to pH 2 with hydrochloric acid while stirring. The precipitate was filtered off and dried in a vacuum oven to give an orange solid, 7.19 g (86% yield).

Mass Spectrum m/e 344 ($M^+$+H).

Preparation of (A5)

A mixture of (A4) (7.18 g, 20.9 mmole) and thionyl chloride (90 mL) was refluxed for 2 hours. After cooling the excess thionyl chloride was removed by rotary evaporation and the residue was suspended in acetone (175 mL) and the resulting suspension cooled in an ice-bath. Aqueous ammonia (S.G. 0.880, 20 mL) was added gradually, keeping the temperature below 10° C. The resulting suspension was filtered off, washed with water and air-dried to give a solid, 5.15 g (75% yield).

Mass Spectrum m/e 343 ($M^+$+H).

Preparation of (A6)

A mixture of (A5) (20.55 g, 60 mmole) and phosphoryl chloride (250 mL) was heated and stirred at 120° C. for 4 hours when the starting material had dissolved. Heating and stirring was continued at 110° C. for 18 hours. After cooling, the solution was evaporated to remove excess phosphoryl chloride. Last traces of phosphoryl chloride were removed by azeotroping with toluene. The residue was treated with ice and aqueous ammonia to remove acidity. The solid product was filtered off and dried in a vacuum oven to give a grey solid, 19.23 g (99% yield).

(This may also be prepared as described in WO 9843960)

Mass Spectrum m/e 325 ($M^+$+H).

Preparation of (A7)

A mixture of (A6) (19.23 g, 60.0 mmole) and trifluoroacetic acid (300 ml) and thioanisole (35 ml) was refluxed in a nitrogen atmosphere for 3 hours. After cooling the trifluoroacetic acid was removed by rotary evaporation and the oily residue was stirred with ice and water and basified with aqueous ammonia (S.G. 0.880). The resulting suspension was filtered and the solid was washed successively with water, ethyl acetate and diethyl ether and then dried to give a khaki solid, 13.74 g (97% yield).

Mass Spectrum m/e 235 ($M^+$+H).

Preparation of (A8)

Potassium tert-butoxide (5.0 g) was added portionwise to a stirred solution of (A7) (10 g) in DMA (200 ml) cooled to 5° C. under an atmosphere of nitrogen. The mixture was stirred at ambient temperature for 30 min. and then cooled to 5° C. 1-chloro-3-bromopropane (7.4 g) was added followed by tetrabutylammonium iodide (1.57 g) and 18-crown-6 (0.5 g) and the mixture stirred at ambient temperature for 16 hr. The DMA was removed in vacuo and the residue partitioned between ethyl acetate and water. The organic extracts were dried and evaporated to dryness. The product was purified by flash column chromatography on silica eluting with 1-2% methanol in dichloromethane to give (A8) as a white solid (6.5 g).

Mass Spectrum m/e 311 ($M^+$+H).

Preparation B

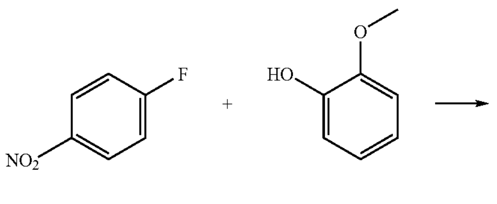

-continued

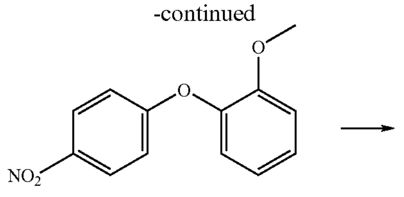

(B1)

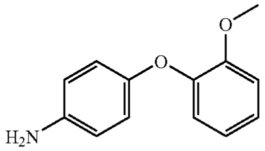

(B2)

+

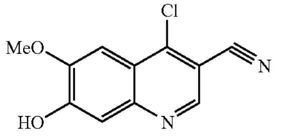

(A7)

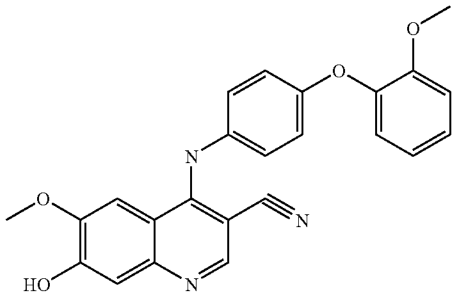

(B3)

Preparation of (B2)

Intermediate (B2) was prepared as described in Rev. Chim. (Bucharest), 1988, 39(6), 477-482.

Preparation of (B3)

A mixture of the 4-chloro-3-cyano-7-hydroxy-6-methoxyquinoline (17.6 g) and 4-(2-methoxyphenoxy)-aniline (17.2 g) in 1-propanol (600 ml) was stirred and refluxed for 4 hours. The mixture was allowed to cool to room temperature overnight and the product was filtered off and washed with 1-propanol and then dried under high vacuum. The product was obtained as a yellow hydrochloride salt, 32.2 g (96% yield).

Mass Spectrum m/e 414 ($M^+$+H)

Preparation C

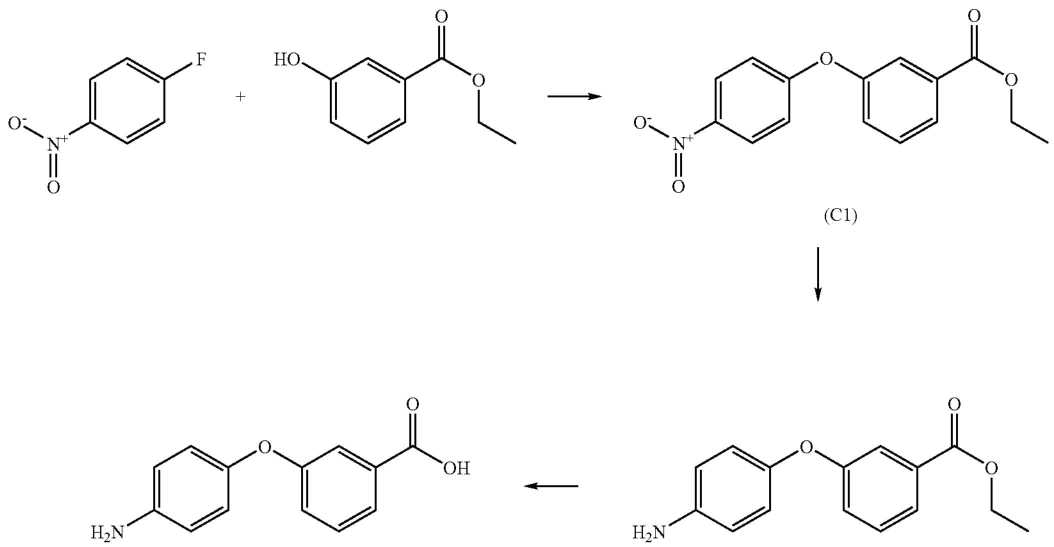

(C1)

(C3) (C2)

Preparation of (C1)

4-fluoro-nitrobenzene and ethyl 3-hydroxybenzoate were reacted together in DMA in the presence of potassium butoxide for 2 hours at 150° C. to yield Intermediate C1.

Mass Spectrum m/e 283.27 $(M-H^+)^-$

Preparation of (C2)

Intermediate (C1) was reduced to the corresponding aniline by reduction, at room temperature in ethyl acetate solution, with hydrogen and catalytic 5% Pd/C to give Intermediate (C2).

Mass Spectrum m/e 258.22 $(M+H)^+$

Preparation of (C3)

Intermediate (C2) was converted to the carboxylic acid by hydrolysis with 2M aqueous sodium hydroxide solution in ethanol for 16 hr at room temperature to give Intermediate (C3).

Mass Spectrum m/e 230.12 $(M+H)^+$

Example 1

Preparation of Compound 1 in Table 1

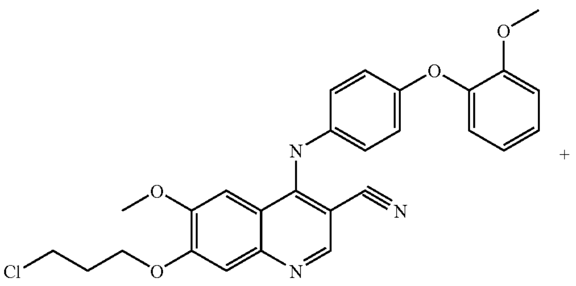

(1)

-continued

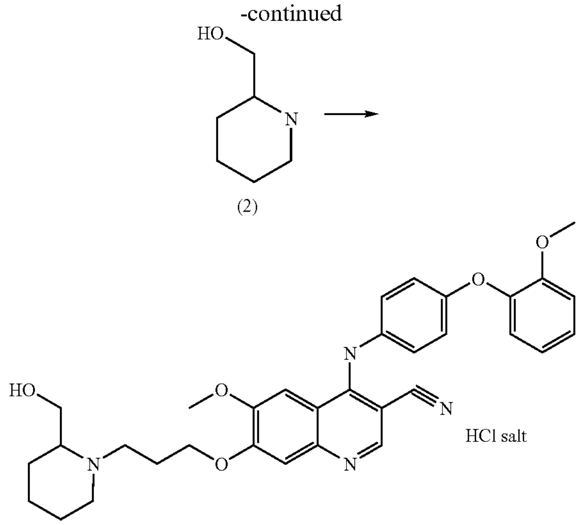

(2)

HCl salt

Step 1

Intermediate (A6) from Preparation 1 (Preparation of 6) above (10.28 g, 0.030 moles) was mixed with 4-(2-methoxyphenoxy)aniline (7.74 g, 0.036 moles), prepared as described in Rev. Chim. (Bucharest) (1988), 39(6), 477-482, in 1-propanol (170 ml) and the mixture was stirred and heated at 115° C. for 5 hours. The mixture was cooled to ambient temperature and then filtered. The crystals were washed with a small volume of 1-propanol and then dried to give 4-(4-(2-methoxyphenoxy)-anilino)-3-cyano-6-methoxy-7-(benzyloxy)quinoline, Mass Spectrum m/e 504 $(M^++H)$.

NMR Spectrum (d-6-DMSO, δ values) 3.73 (s, 3H), 3.97 (s, 3H), 5.32 (s, 2H), 6.95 (m, 3H), 7.05 (d, 1H), 7.18 (m, 2H), 7.38 (m, 5H), 7.51 (d, 2H), 7.58 (s, 1H), 8.17 (s, 1H), 8.87 (s, 1H), 11.13 (broad, 1H).

Step 2

The product from step (1) (7.2 g, 14.3 mmole) trifluoroacetic acid (40 ml) and thioanisole (8.38 ml, 71.5 mmole) was refluxed in a nitrogen atmosphere for 3 hours. After cooling the trifluoroacetic acid was removed by rotary evaporation and the oily residue was stirred with ice and water and basified with aqueous ammonia (S.G. 0.880). The resulting suspension was filtered and the solid was washed successively with water, ethyl acetate and diethyl ether and then dried to give 4-(4-(2-methoxyphenoxy)-anilino)-3-cyano-6-methoxy-7-hydroxyquinoline.

Mass Spectrum m/e 414 ($M^+$+H).

NMR Spectrum (d-6-DMSO, δ values) 3.75 (s, 3H), 3.91 (s, 3H), 6.89 (d, 2H), 6.94 (m, 1H), 7.02 (d, 1H), 7.16 (m, 3H), 7.23 (m, 1H), 7.73 (s, 1H), 8.31 (s, 1H), 9.33 (s, 1H), 10.31 (broad, 1H).

Step 3

The product of step 2 (206.5 mg, 0.5 mmole) and 1-chloro-3-bromopropane (95 mg, 0.6 mmole) was dissolved in dimethylsulphoxide (5 ml) in the presence of potassium butoxide (0.55 ml, 11.0M in THF, 0.55 mmole) in and the mixture held at room temperature for 18 hours. Water was added and the mixture extracted with ethyl acetate. The combined extracts were washed with water and brine then dried ($MgSO_4$) and evaporated to give 4-(4-(2-methoxyphenoxy)-anilino)-3-cyano-6-methoxy-7-(3-chloropropoxy)quinoline, intermediate 1, (189 mg, 77%) as a yellow gum.

Mass Spectrum m/e 490 ($M^+$+H)

Step 4

A mixture of 4-(4-(2-methoxyphenoxy)-anilino)-3-cyano-6-methoxy-7-(3-chloropropoxy)quinoline, intermediate 1, an excess (5 molar equivalents) of 2-(hydroxymethyl)piperidine and sodium iodide (1 molar equivalent) were heated together in DMA at 60° C. for 18 hours. The reaction mixture was evaporated and the residue partitioned between water and ethyl acetate. The combined organic extracts were washed with water and brine then dried ($MgSO_4$) and evaporated. The residue was chromatographed eluting with a gradient of dichloromethane and dichloromethane containing 10% of methylamine (33% in ethanol) solution from 0% to 100%. Fractions containing product were evaporated. Compound No. 1 was obtained as the hydrochloride salt by treatment of the residue in ethanol with 1.0M hydrogen chloride (2 molar equivalents) in ether.

Mass Spectrum m/e 569 ($M^+$+H).

Example 2

Preparation of Compound 2 in Table 1

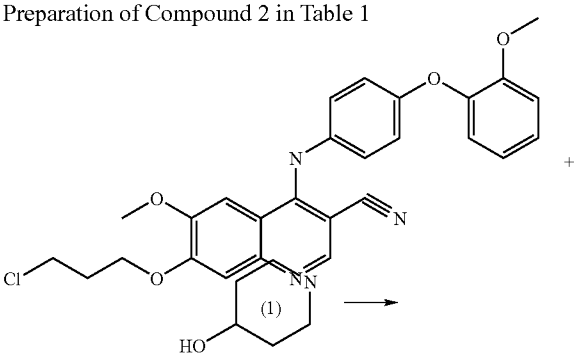

(1)

(2)

-continued

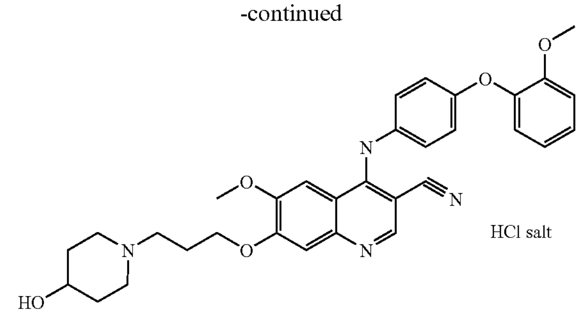

A mixture of intermediate 1, Example 1, Step 3, excess of 4-hydroxypiperidine (44 molar equivalents) and sodium iodide (1 molar equivalent in DMA) were heated, without solvent, together at 60° C. for 20 hours. The reaction mixture was evaporated and the residue partitioned between water and ethyl acetate. The combined organic extracts were washed with water and brine then dried ($MgSO_4$) and evaporated. The residue was chromatographed. Fractions containing product were evaporated. Compound No. 2 was obtained as the hydrochloride salt by treatment of the residue in ethanol with 1.0M hydrogen chloride (2 molar equivalents) in ether.

Mass Spectrum m/e 555 ($M^+$+H).

NMR Spectrum (d-6-DMSO, δ values) 1.73 (m, 2H), 1.97 (m, 2H), 2.33 (m, 2H), 2.96 (m, 1H), 3.19 (m, 2H), 3.31 (m, 2H), 3.47 (m, 2H), 3.73 (s, 3H), 3.99 (s, 3H), 4.26 (t, 2H), 6.96 (m, 3H), 7.05 (d, 1H), 7.19 (m, 2H), 7.39 (d, 2H), 7.56 (s, 1H), 8.23 (s, 1H), 8.88 (s, 1H), 11.22 (broad, 1H)

Example 3

Preparation of Compound 3 in Table 1

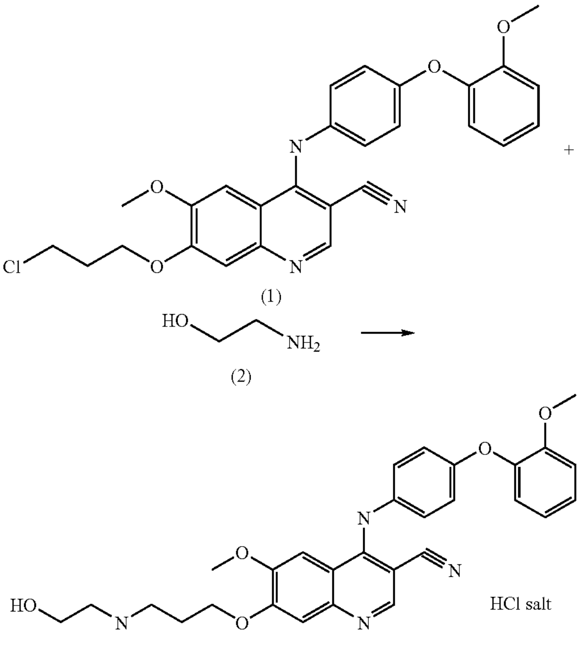

(1)

(2)

A mixture of intermediate 1, Example 1, Step 3, and excess of 4-hydroxyethanol (25 molar equivalents) were heated in n-propanol solution at 60° C. for 72 hours. The reaction mixture was worked up as described in Example 1, Step 4 and Compound No. 3 was obtained as the hydrochloride salt.

Mass Spectrum m/e 515 ($M^{+}$+H).

NMR Spectrum (d-6-DMSO, δ values) 2.25 (m, 2H), 3.03 (m, 2H), 3.12 (m, 2H), 3.68 (m, 2H), 3.73 (s, 3H), 3.97 (s, 3H), 4.28 (t, 2H), 6.96 (m, 3H), 7.05 (d, 1H), 7.18 (m, 2H), 7.39 (d, 2H), 7.55 (s, 1H), 8.22 (s, 1H), 8.88 (s, 1H), 8.96 (broad, 1H), 11.20 (broad, 1H)

Example 4

Preparation of Compound 4 in Table 1

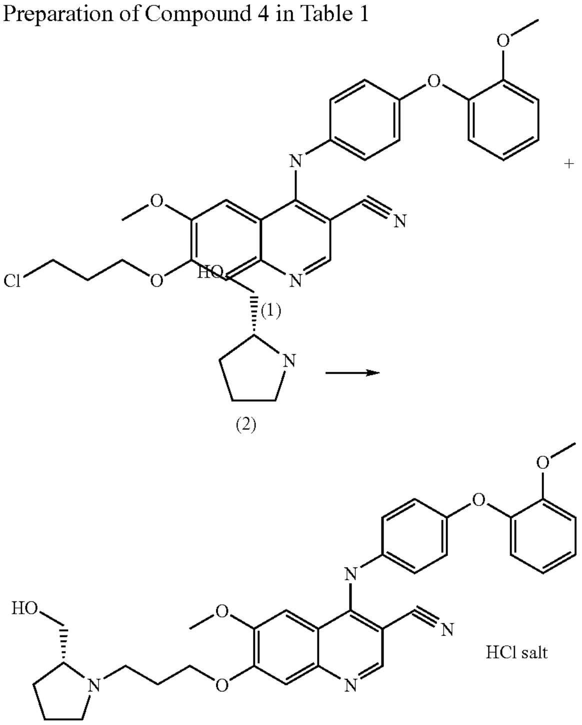

(1)
(2)

By using the procedure described in Example 1, Step 4, but using 2-hydroxymethylpyrrolidine in place of 2-hydroxymethylpiperidine, the title compound was obtained after chromatographic purification.

Mass Spectrum m/e 555 ($M^{+}$+H).

Example 5

Preparation of Compound 5 in Table 1

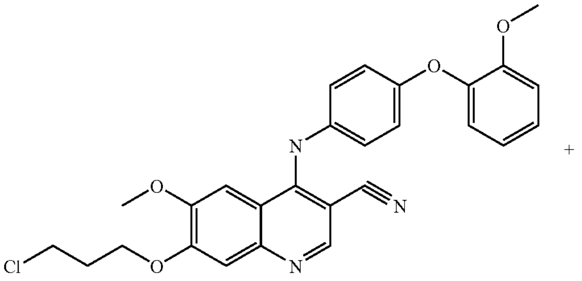
(1)

-continued

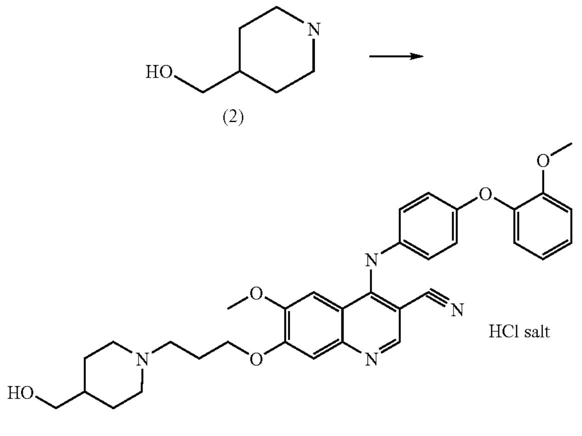

(2)

By using the procedure described in Example 1, Step 4, but using 4-hydroxymethylpiperidine in place of 2-hydroxymethylpiperidine, the title compound was obtained after chromatographic purification.

Mass Spectrum m/e 569 ($M^{+}$+H).

Example 6

Preparation of Compound 6 in Table 1

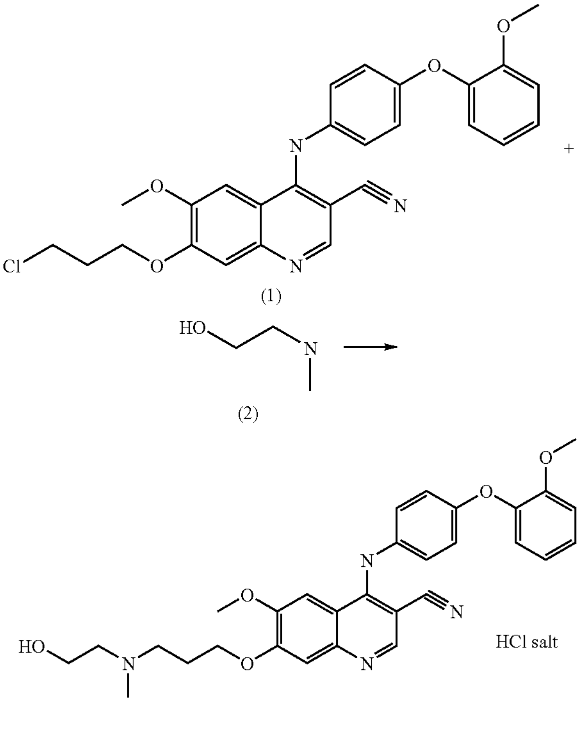

(1)
(2)

By using the procedure described in Example 1, Step 4, but using N-methyl-2-hydroxyethylamine in place of 2-hydroxymethylpiperidine, the title compound was obtained after chromatographic purification.

Mass Spectrum m/e 529 ($M^{+}$+H).

Example 7

Preparation of Compound 7 in Table 1

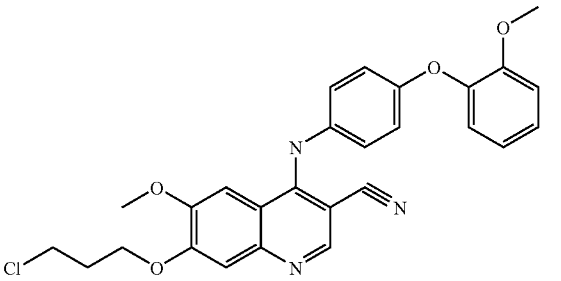

+

(1)

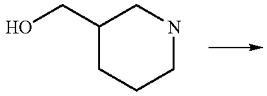

(2)

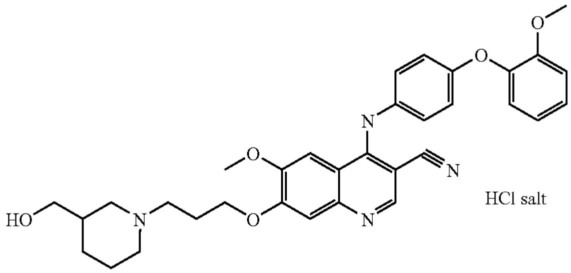

HCl salt

By using the procedure described in Example 1, Step 4, but using 3-hydroxymethylpiperidine in place of 2-hydroxymethylpiperidine, the title compound was obtained after chromatographic purification.

Mass Spectrum m/e 569 ($M^+$+H).

Example 8

Preparation of Compound 8 in Table 1

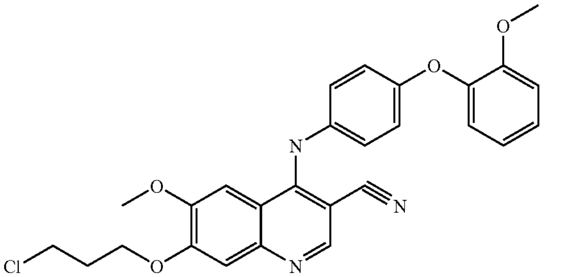

+

(1)

-continued

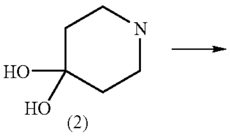

(2)

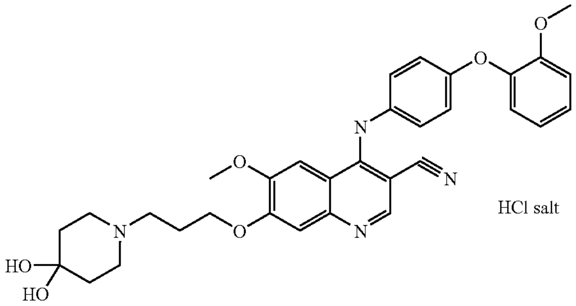

HCl salt

By using the procedure described in Example 1, Step 4, but using 4,4-dihydroxypiperidine in place of 2-hydroxymethylpiperidine, and including 5 molar equivalents of potassium carbonate in the reaction mixture, the title compound was obtained after chromatographic purification.

Mass Spectrum m/e 571 ($M^+$+H).

NMR Spectrum (d-6-DMSO, δ values) 2.39 (m, 2H), 2.98 (m, 2H), 3.39 (broad, 8H), 3.76 (s, 3H), 4.09 (s, 3H), 4.35 (t, 2H), 6.99 (m, 3H), 7.07 (m, 1H), 7.22 (m, 2H), 7.41 (d, 2H), 7.53 (s, 1H), 8.17 (s, 1H), 8.89 (s, 1H), 11.00 (broad, 1H), 11.49 (broad, 1H)

Example 9

Preparation of Compound 9 in Table 1

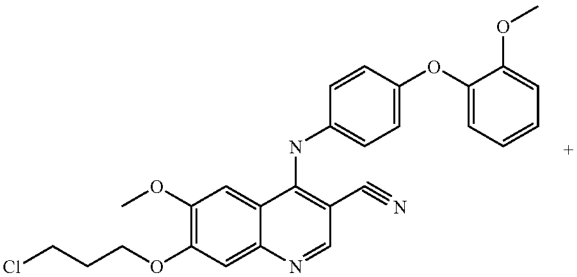

+

(1)

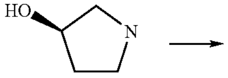

(2)

-continued
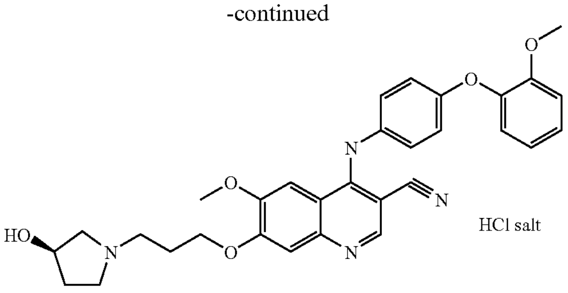
HCl salt
By using the procedure described in Example 1, Step 4, but using 3-hydroxypyrrolidine in place of 2-hydroxymethylpiperidine, the title compound was obtained after chromatographic purification.
Mass Spectrum m/e 541 ($M^+$+H).
Example 10
Preparation of Compound 10 in Table 1
This compound was prepared using the following scheme.

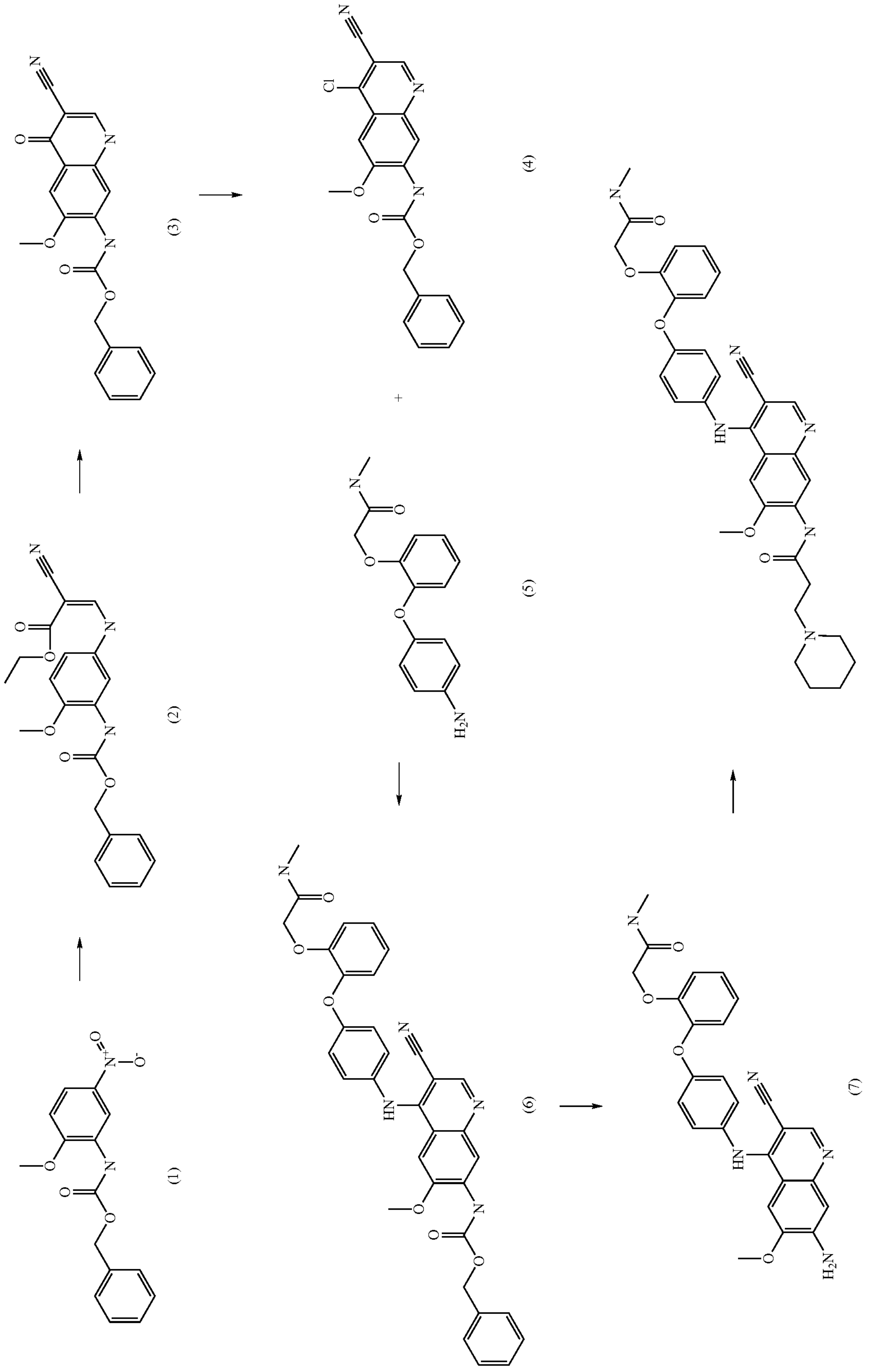
(1)
(2)
(3)
(4)
(5)
(6)
(7)

Step 1

Intermediate (1) was obtained by reaction of benzylchloroformate (25.7 ml, 0.18 mol, 1.2 equiv.) and 2-methoxy-5-nitroniline (25 g, 1.0 equiv.) in pyridine (190 ml) at room temperature for 18 hours.

NMR Spectrum (d-6-DMSO, δ values) 3.93 (s, 3H), 5.18 (s, 2H), 7.21 (d, 1H), 7.37 (m, 51), 7.98 (m, 1H), 8.69 (m, 1H), 9.10 (s, 1H).

Step 2

Intermediate (2) was prepared by treating intermediate (1) (28.7 g, 94.97 mmol, 1.0 equiv.) in ethyl acetate (550 ml) with $SnCl_2.2H_2O$ (85.7 g, 0.38 mol, 4 equiv.) at 105° C. for 5 hrs. After this, ethoxymethylenecyanoacetate (16.0 g, 95 mmol, 1.0 equiv.) in ethanol (200 ml) was added and the mixture held at 90° C. for 90 mins. The mixture was cooled, and Intermediate (2) was isolated by filtration, washed with ethanol and dried under vacuum.

NMR Spectrum (d-6-DMSO, δ values) (~3:1 mixture of isomers) 1.22 (m, 3H), 3.76 (s, 3H), 4.16 (m, 2H), 5.13 (s, 2H), 7.02 (m, 2H), 7.35 (m 5H), 7.72 (m, 0.25H), 7.80 (m, 0.75H), 8.14 (bs, 0.75H), 8.26 (d, 0.25H), 8.66 (s, 0.25H), 8.71 (s, 0.75H), 10.65 (d, 0.25H), 10.78 (bs, 0.75H).

Step 3

Intermediate (2) was converted to Intermediate (3) in the above scheme by contact with Dowtherm A for 4 hours at 250-260° C.

Mass Spectrum m/e 350 $(M+H)^+$.

Step 4

The product of Step 3 was chlorinated using $POCl_3$ in MeCN at 110° C. for 2 hrs. Intermediate (4) in the above scheme was obtained.

Mass Spectrum m/e 368, 370 $(M+H)^+$.

Step 5

4-(2-N-methylcarboxamidomethoxy-phenoxy)nitrobenzene, obtained by reacting 4-fluoronitrobenzene with (2-N-methylcarboxamidomethoxy)phenol for 2.5 hours at 150° C. in DMA in the presence of potassium butoxide, was dissolved in ethyl acetate and hydrogenated for 18 hours in the presence of a 10% palladium/carbon catalyst. The catalyst was filtered, the solution concentrated in vacuo, and upon standing 4-(2-N-methylcarboxamidomethoxy-phenoxy)aniline, intermediate 5, was obtained as crystals.

Mass Spectrum n/e 273 $(M+H)^+$

Step 6

Intermediate 5 was reacted with intermediate 4, in n-propanol solution at 100° C. for 90 mins. Intermediate 6 was obtained.

Mass Spectrum m/e 604 $(M+H)^+$.

NMR Spectrum (d-6-DMSO, δ values) 2.60 (d, 3H), 4.00 (s, 3H), 4.47 (2H, s), 5.24 (s, 2H), 7.03 (m, 5H), 7.12 (m, 2H), 7.37 (m, 5H), 7.46 (m, 2H), 7.53 (m, 1H), 8.13 (s, 1H), 8.58 (s, 1H), 8.79(s, 1H), 9.42 (s, 1H).

Step 7

Intermediate 6 was converted to intermediate 7 by treatment with 33% HBr in AcOH in the presence of thioanisole at 0° C. to RT for 3 hr. After chromatographic purification, intermediate 7 was obtained.

Mass Spectrum m/e 470 $(M+H)^+$.

Step 8

A solution of intermediate 7 in DCM was coupled with N-piperidine-3-propionic acid using 1-(3-dimethylaminopropyl)-3-ethylcarbodiimide (EDAC) and dimethylaminopyridine (DMAP) at room temperature for 6 days to yield, after chromatographic purification, the title compound.

Mass Spectrum m/e 609 $(M+H)^+$.

NMR Spectrum (d-6-DMSO, δ values) 1.74 (m, 6H), 2.62 (d, 3H), 2.89 (m, 2H), 3.14 (m, 4H), 4.08 (s, 3H), 4.53 (2H, s), 7.05 (m, 5H), 7.13 (m, 2H), 7.42 (d, 2H), 7.55 (m, 1H), 8.24 (s, 1H), 8.85 (s, 1H), 8.89 (s, 1H).

Example 11

Preparation of Compound 11 in Table 1

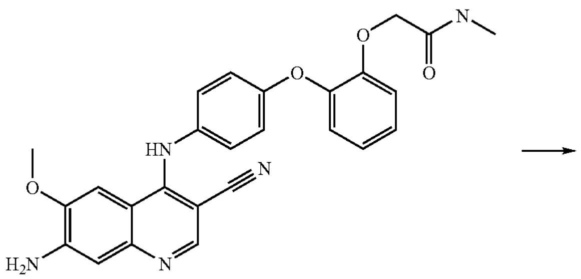

(1)

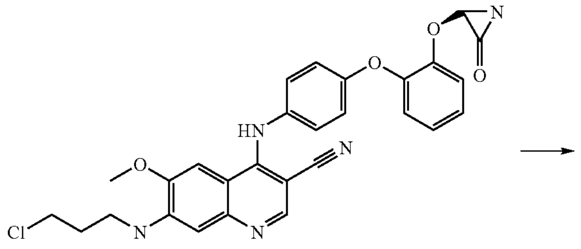

(2)

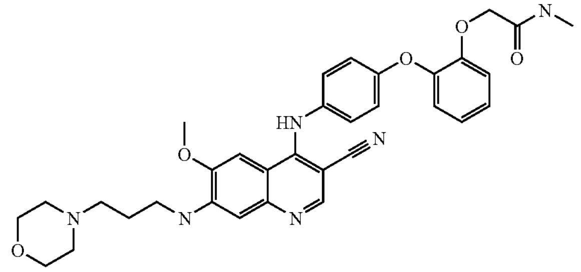

Example 11

Step 1

Intermediate 1, Example 10, Step 7, was converted to intermediate 2 by reaction with 1-bromo-3-chloropropane by a procedure analogous to that described in Preparation of Key Intermediates, Preparation of (8). Intermediate 2 was obtained.

Mass Spectrum m/e 546, 548 $(M+H)^+$.

Step 2

Intermediate 2 was reacted with morpholine in the presence of sodium iodide at room temperature for 9 days to give, after chromatographic purification, the title compound Mass Spectrum m/e 595 $(M+H)^+$.

NMR Spectrum (d-6-DMSO, δ values) 2.08 (m, 2H), 2.60 (d, 3H), 3.04(m, 2H), 3.16 (m, 2H), 3.40 (m, 2H), 3.80 (m, 2H), 3.92 (m, 2H), 4.00 (s, 3H), 4.46 (2H, s), 6.95 (1H, s), 7.04 (m, 5H), 7.16 (m, 2H), 7.39 (d, 2H), 7.54 (m, 1H), 7.92 (s, 1H), 8.80 (s, 1H).

Example 12

Preparation of Compound 12 in Table 1

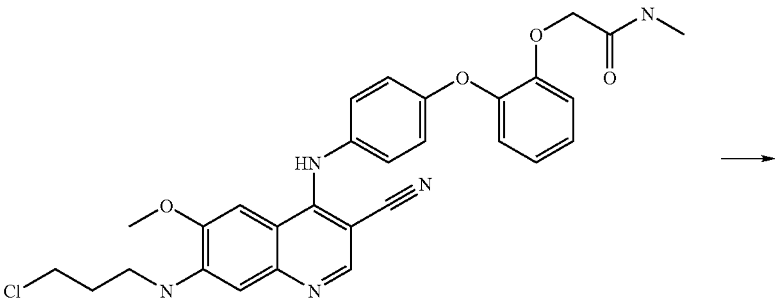

(1)

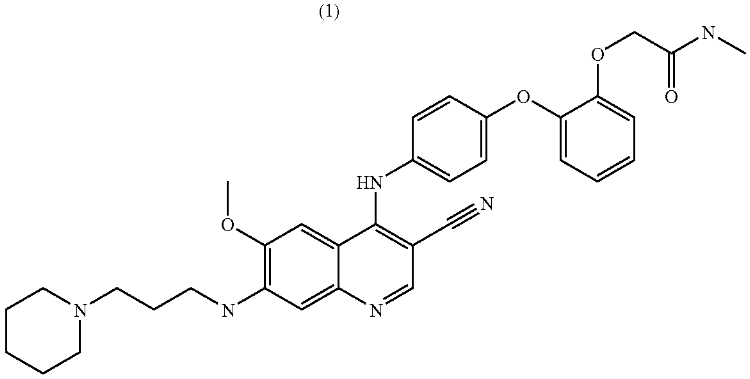

(Example 12)

Intermediate 1, Example 11, Step 1, was converted to the title compound by a process analogous to that described in Example 11, Step 2, using piperidine in place of morpholine. The title compound was obtained after chromatographic purification.

Mass Spectrum m/e 593 $(M+H)^+$.

NMR Spectrum-(d-6-DMSO, δ values) 1.37 (m, 1H), 1.76 (m, 5H), 2.06 (m, 2H), 2.62 (d, 3H), 2.84 (m, 2H), 3.07 (m, 2H), 3.39 (m, 2H), 4.01 (s, 3H), 4.33 (2H, s), 7.00 (2H, m), 7.08 (m, 4H), 7.16 (m, 2H), 7.39 (d, 2H), 7.55 (m, 1H), 7.96 (s, 1H), 8.79 (s, 1H).

Example 13

Preparation of Compound 13 in Table 1

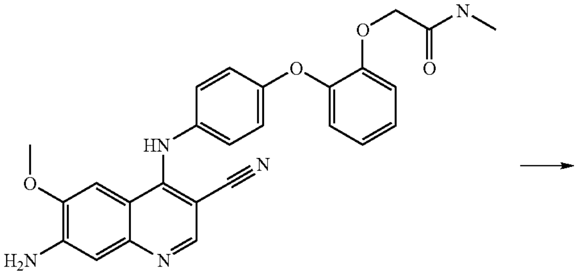

(1)

-continued

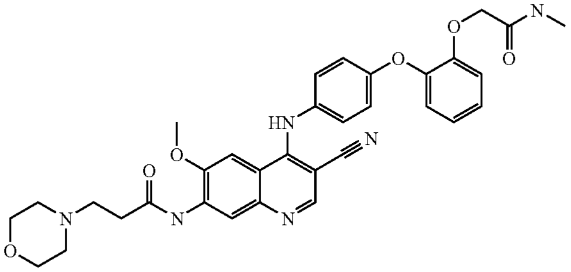

(Example 12)

Intermediate 1 (Example 10, Step 7) was converted to the title product by a process analogous to that of Example 10, Step 8, but using N-morpholine-3-propionic acid in place of N-piperidine-3-propionic acid. After chromatographic purification, the title compound was obtained.

Mass Spectrum m/e 611 $(M+H)^+$.

NMR Spectrum (d-6-DMSO+d-4-AcOH, 6 values) 2.62 (s, 3H), 3.14 (m, 4H), 3.42 (m, 4H), 4.08 (s, 3H), 4.45 (2H, s), 7.04 (m, 5H), 7.13 (m, 2H), 7.42 (d, 2H), 8.21 (m, 1H), 8.89 (s, 1H).

Example 14

Preparation of Compound 14 in Table 1

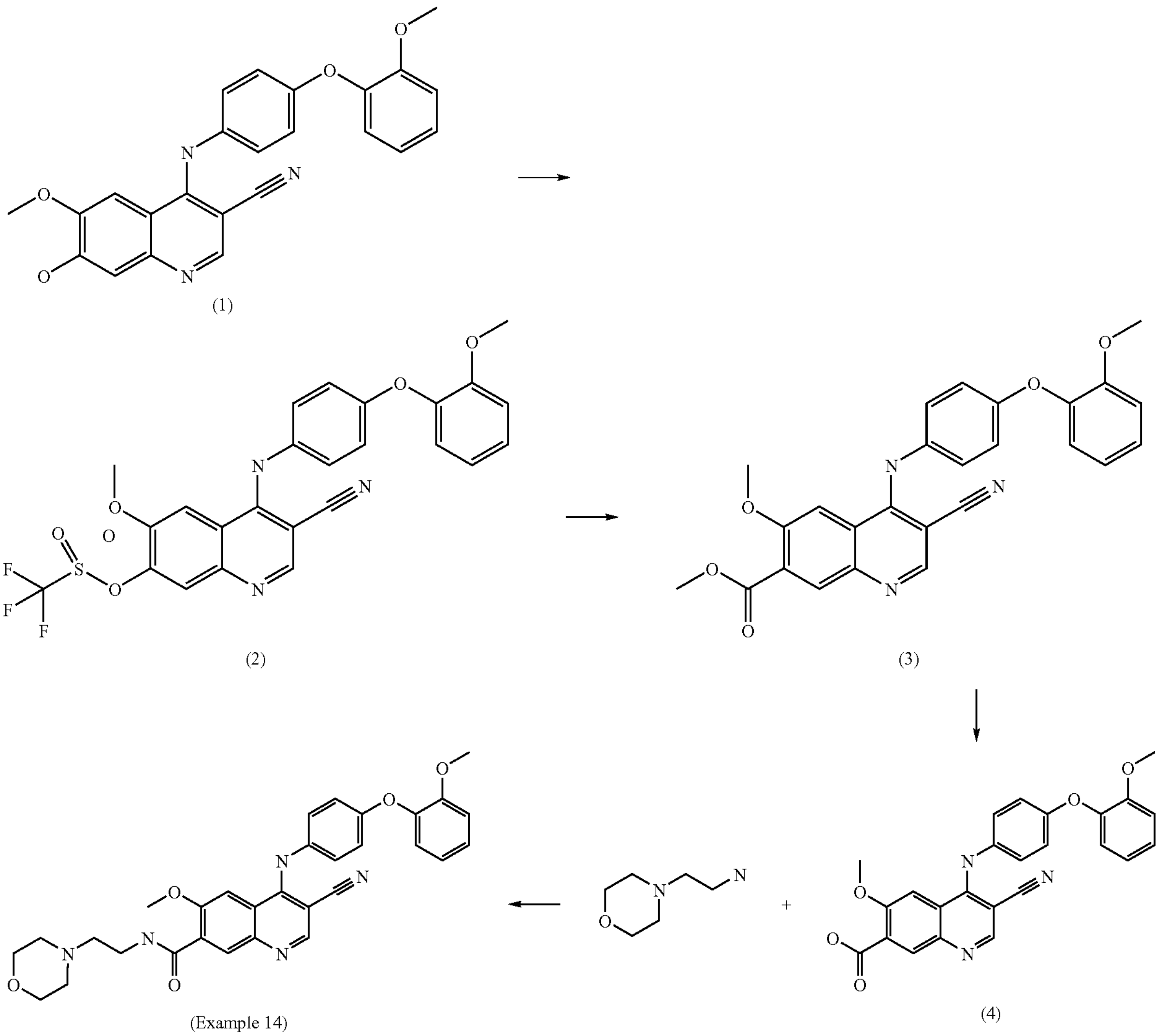

(1) (2) (3) (4) (Example 14)

Step 1

Intermediate 1 (Example 1, Step 2) was reacted in DCM solution with triflic anhydride in the presence of lutidine and DMAP to give intermediate 2.

Mass Spectrum m/e 546 ($M^+$+H).

Step 2

Intermediate 2 was reacted in DMF/methanol solution with carbon monoxide in the presence of palladium acetate, 1,3-bis(diphenylphosphino)propane and triethylamine at 70° C. to give intermediate 3.

Mass Spectrum m/e 456 ($M^+$+H).

Step 3

Intermediate 3 was hydrolysed with lithium hydroxide in a mixture of methanol, THF and water to give intermediate 4.

Mass Spectrum m/e 442 ($M^+$+H).

Step 4

Intermediate 4 was coupled with N-2-aminoethylmorpholine in DMF solution using HATU to give, after chromatographic purification on silica using as eluant 0-4% methanol in DCM, the title compound.

Mass Spectrum m/e 554 ($M^+$+H).

NMR Spectrum (d-6-DMSO, δ values) 2.30-2.60 (m, 4H), 2.87-2.95 (m, 1H), 3.15-3.30 (m, 1H), 3.37-3.70 (m, 6H), 3.73 (s, 3H), 4.00 (s, 3H), 6.94 (m, 3H), 7.02 (m, 1H), 7.17 (m, 2H), 7.29 (m, 2H), 7.91(s, 1H), 8.17 (s, 1H). 1H), 8.43 (s, 1H), 8.48 (br.s, 1H), 9.70 (s, 1H).

Example 15

Preparation of Compound 15 in Table 1

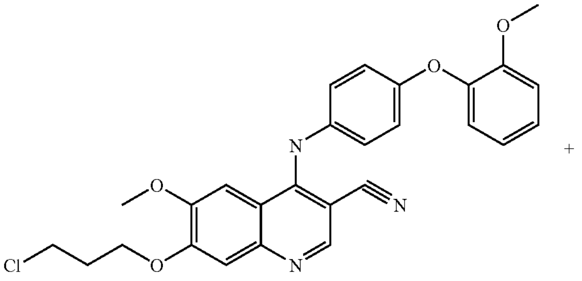

(1)

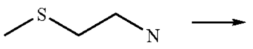

(2)

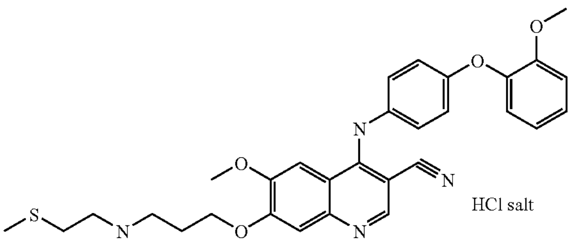

(Example 15)

By using the procedure described in Example 1, Step 4, but using 2-methylthioethylamine in place of 2-hydroxymethylpiperidine, the title compound was obtained after chromatographic purification.

Mass Spectrum m/e 545 ($M^+$+H).

Example 16

Preparation of Compound 16 in Table 1

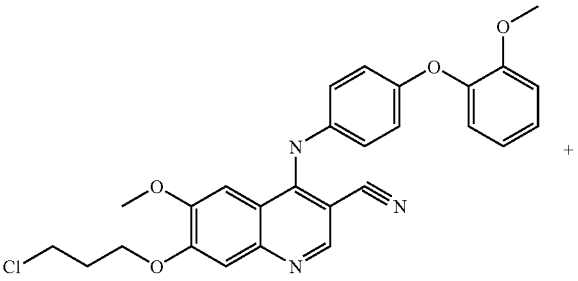

(1)

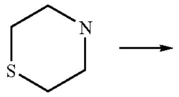

(2)

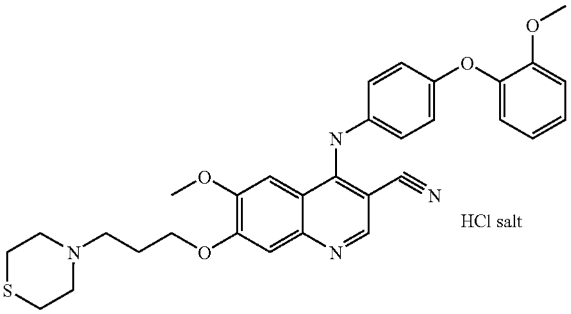

(Example 16)

By using the procedure described in Example 2, but using thiomopholine in place of 4-hydroxypiperidine, the title compound was obtained after chromatographic purification.

Mass Spectrum m/e 557 ($M^+$+H).

NMR Spectrum (d-6-DMSO, δ values) 2.32 (m, 2H), 2.83 (d, 2H), 3.21 (m, 6H), 3.74 (s, 3H), 3.78 (m, 2H), 3.99 (s, 3H), 4.29 (t, 2H), 6.97 (m, 3H), 7.05 (d, 1H), 7.19 (m, 2H), 7.39 (d, 2H), 7.51 (s, 1H), 8.16 (s, 1H), 8.88 (s, 1H), 11.00 (broad, 1H)

Example 17

Preparation of Compound 17 in Table 1

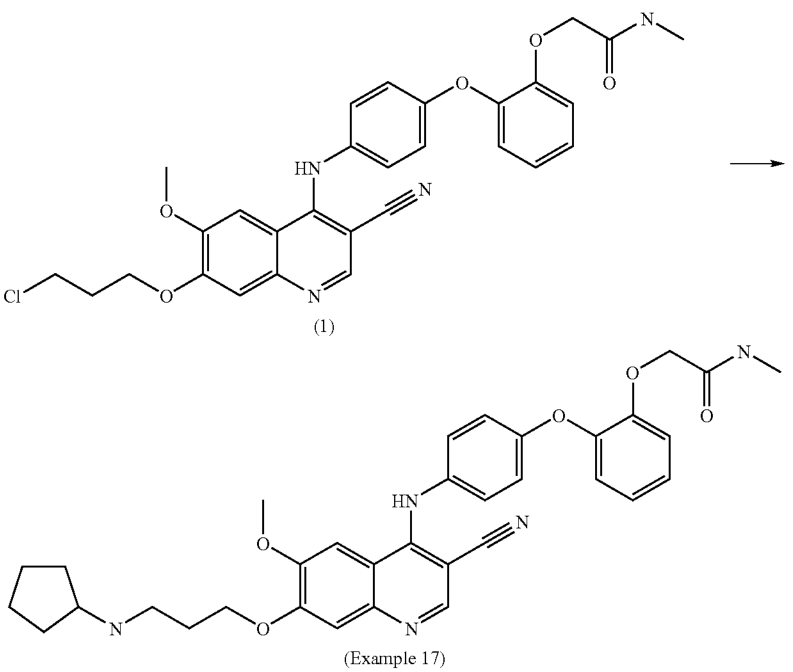

(1)

(Example 17)

Step 1

4-(2-N-methylcarboxamidomethoxy-phenoxy)aniline (Example 10, Step 5) was reacted with 4-chloro-3-cyano-6-methoxy-7-(3-chloropropoxy)quinoline (Preparation of Key Intermediates, Preparation of (8)) in 1-propanol and the mixture was stirred and heated at 100° C. for 18 hours. The mixture was cooled to ambient temperature and then filtered. The crystals were washed with a small volume of 1-propanol and then dried to give 4-(4-(2-N-methylcarboxamidomethoxy-phenoxy)-anilino)-3-cyano-6-methoxy-7-(3-chloropropoxy)quinoline, intermediate 1.

Mass Spectrum m/e 547.5 $(M+H)^+$.

Step 2

Intermediate 1 was reacted with cyclopentylamine at 100° C. for 3 hr to give, after chromatographic purification, the title compound.

Mass Spectrum m/e 596 $(M+H)^+$.

NMR Spectrum (d-6-DMSO+d-4-AcOH, δ values) 1.62 (m, 6H), 1.95 (m, 2H), 2.21 (m, 2H), 2.60 (s, 3H), 3.08 (m, 2H), 3.50 (m, 2H), 3.99 (s, 3H), 4.28 (m, 2H), 4.45 (s, 2H), 7.04 (d, 2H), 7.10 (m, 4H), 7.40 (d, 2H), 7.47 (s, 1H), 8.12 (s, 1H), 8.87 (s, 1H).

Example 18

Preparation of Compound No. 18 in Table 2

Step 1

Intermediate (A6) from Preparation A above (10.28 g, 0.030 moles) was mixed with 4-(2-methoxyphenoxy)aniline (7.74 g, 0.036 moles), prepared as described in Rev. Chim. (Bucharest) (1988), 39(6), 477-482, in 1-propanol (170 ml) and the mixture was stirred and heated at 115° C. for 5 hours. The mixture was cooled to ambient temperature and then filtered. The crystals were washed with a small volume of 1-propanol and then dried to give 4-(4-(2-methoxyphenoxy)-anilino)-3-cyano-6-methoxy-7-(benzyloxy)quinoline, Mass Spectrum m/e 504 $(M^+ +H)$.

NMR Spectrum (d-6-DMSO, δ values) 3.73 (s, 3H), 3.97 (s, 3H), 5.32 (s, 2H), 6.95 (m, 3H), 7.05 (d, 1H), 7.18 (m, 2H), 7.38 (m, 5H), 7.51 (d, 2H), 7.58 (s, 1H), 8.17 (s, 1H), 8.87 (s, 1H), 11.13 (broad, 1H).

Step 2

The product from step (1) (7.2 g, 14.3 mmole) trifluoroacetic acid (40 ml) and thioanisole (8.38 ml, 71.5 mmole) was refluxed in a nitrogen atmosphere for 3 hours. After cooling the trifluoroacetic acid was removed by rotary evaporation and the oily residue was stirred with ice and water and basified with aqueous ammonia (S.G. 0.880). The resulting suspension was filtered and the solid was washed successively with water, ethyl acetate and diethyl ether and then dried to give 4-(4-(2-methoxyphenoxy)-anilino)-3-cyano-6-methoxy-7-hydroxyquinoline.

Mass Spectrum m/e 414 $(M^+ +H)$.

NMR Spectrum (d-6-DMSO, δ values) 3.75 (s, 3H), 3.91 (s, 3H), 6.89 (d, 2H), 6.94 (m, 1H), 7.02 (d, 1H), 7.16 (m, 3H), 7.23 (m, 1H), 7.73 (s, 1H), 8.31 (s, 1H), 9.33 (s, 1H), 10.31 (broad, 1H).

Step 3

The product of step 2 (206.5 mg, 0.5 mmole) and 1-chloro-3-bromopropane (95 mg, 0.6 mmole) was dissolved in dimethylsulphoxide (5 ml) in the presence of potassium butoxide (0.55 ml, 11.0M in THF, 0.55 mmole) in and the mixture held at room temperature for 18 hours. Water was added and the mixture extracted with ethyl acetate. The combined extracts were washed with water and brine then dried ($MgSO_4$) and evaporated to give 4-(4-(2-methoxyphenoxy)-anilino)-3-cyano-6-methoxy-7-(3-chloropropoxy)quinoline (189 mg, 77%) as a yellow gum.

Mass Spectrum m/e 490 ($M^+$+H)

Step 4

A mixture of 4-(4-(2-methoxyphenoxy)-anilino)-3-cyano-6-methoxy-7-(3-chloropropoxy)quinoline, an excess (44 molar equivalents) of N-(2-methoxyethyl)piperidine (available commercially) and sodium iodide (1 molar equivalent) were heated together at 50° C. for 20 hours. The reaction mixture was evaporated and the residue partitioned between water and ethyl acetate. The combined organic extracts were washed with water and brine then dried ($MgSO_4$) and evaporated. The residue was chromatographed on a Bond Elut (10 g) cartridge eluting with a gradient of dichloromethane and dichloromethane containing 10% of methylamine (33% in ethanol) solution from 0% to 100%. Fractions containing product were evaporated. Compound No. 1 was obtained as the hydrochloride salt by treatment of the residue in ethanol with 1.0M hydrogen chloride (2 molar equivalents) in ether.

Mass Spectrum m/e 598 ($M^+$+H).

NMR Spectrum (d-6-DMSO, δ values) 2.33 (m, 2H), 3.28 (s, 3H), 3.36 (m, 4H), 3.51 (m, 6H), 3.71 (m, 4H), 3.73 (s, 3H), 3.99 (s, 3H), 4.31 (t, 2H), 6.96 (m, 3H), 7.04 (d, 1H), 7.18 (m, 2H), 7.39 (d, 2H), 7.56 (s, 1H), 8.26 (s, 1H), 8.89 (s, 1H), 11.28 (broad, 1H)

Example 19

Preparation of Compound No. 19 in Table 2

Step 1

4-(2-N-methylcarboxamidomethoxy-phenoxy)nitrobenzene, obtained by reacting 4-fluoronitrobenzene with (2-N-methylcarboxamidomethoxy)phenol for 2.5 hours at 150° C. in DMA in the presence of potassium butoxide, was dissolved in ethyl acetate and hydrogenated for 18 hours in the presence of a 10% palladium/carbon catalyst. The catalyst was filtered, the solution concentrated in vacuo, and upon standing 4-(2-N-methylcarboxamidomethoxy-phenoxy)aminobenzene was obtained as crystals.

Mass Spectrum m/e 273 $(M+H)^+$

Step 2

Intermediate (A8) from Preparation A above (0.60 g, 2.3 mmol) was mixed with the product of step 1 (0.68 g, 2.5 mmol) in 1-propanol and the mixture was stirred and heated at 100° C. for 18 hours. The mixture was cooled to ambient temperature and then filtered. The crystals were washed with a small volume of 1-propanol and then dried to give 4-(4-(2-N-methylcarboxamidomethoxy-phenoxy)-anilino)-3-cyano-6-methoxy-7-(3-chloropropoxy)quinoline.

Mass Spectrum m/e 547.5 $(M+H)^+$

Step 3

The product from step 2 (0.2 g, 0.37 mmol) was mixed with cyclopropylamine (5 ml) and stirred for 4 days at room temperature. The mixture was concentrated in vacuo and the residue washed with ether then extracted with DCM/water (3×). The combined DCM extracts were dried, evaporated and the residue chromatographed on silica gel using 10% methanol in DCM containing 0.5% 0.880 aqueous ammonia solution. Fractions containing the product were evaporated and the residue treated with ethereal hydrogen chloride and Compound 19 was isolated as the hydrochloride salt (0.16 g, 79%).

Mass Spectrum m/e 568 $(M+H)^+$.

NMR Spectrum (d-6-DMSO+d-4-AcOH, 5 values) 0.76 (m, 2H), 0.91 (m, 2H), 2.21 (m, 2H), 2.60 (s, 3H), 2.74 (m, 1H), 3.17 (m, 2H), 3.95 (s, 3H), 4.28 (m, 2H), 4.45 (s, 2H), 7.02 (m, 6H), 7.37 (d, 2H), 7.43 (s, 1H), 8.04 (s, 1H), 8.74 (s, 1H).

Example 20

Preparation of Compound No 20 in Table 2

Step 1

Using processes analogous to that described for the preparation of Intermediate (A7) above but using 3-methoxy-4-benzyloxy-anline instead of starting material (A1), 3-cyano-4-chloro-6-hydroxy-7-methoxyquinoline was obtained.

Mass spectrum m/e 234 ($M^+$+H).

Step 2

The product from step 1 (1 g) was reacted with propargyl bromide (0.95 g) in the presence of potassium butoxide (0.53 g), tetrabutylammonium iodide (0.16 g) and 18C-6 crown ether (0.05 g), in solution in DMA (100 ml, 10° C. to ambient temperature). 3-cyano-4-chloro-6-propargyloxy-7-methoxyquinoline (0.73 g) was obtained.

Mass Spectrum m/e 273 ($M^+$+H).

Step 3

4-nitro-fluorobenzene and 2-(carboxymethoxy)phenol were reacted together in DMA in the presence of potassium butoxide for 2 hours at 150° C. to yield 4-(2-carboxymethoxyphenoxy)nitrobenzene.

Mass Spectrum m/e 288 $(M-H^+)^-$

Step 4

A solution of the product of step 3 in DMA was then coupled with methyl glycine using 1-(3-dimethylaminopropyl)-3-ethylcarbodiimide (EDAC), dimethylaminopyridine (DMAP) and N-hydroxybenzotriazole (HOBT) to yield the intermediate of formula

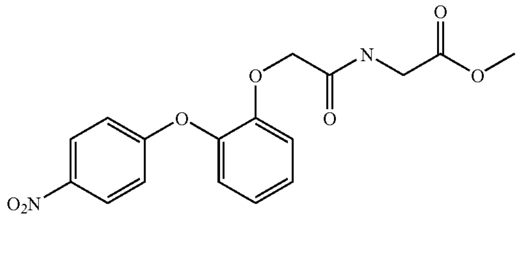

Mass Spectrum m/e 361.17 ($M^+$+H).

Step 5

Reduction of the product of step 4 to the corresponding amine, was effected by hydrogenation in the presence of a 5% Pd/C catalyst.

Mass Spectrum rule 331.14($M^+$+H).

Step 6

Reacting the product of step 5 in methanol with cyclopropylamine at room temperature for 3 hours resulted in the production of the intermediate of formula

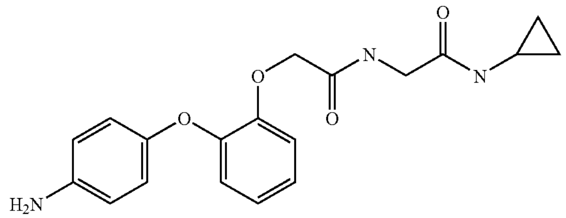

Mass Spectrum m/e 356.23 ($M^+$+H).

Step 7

The products of steps 2 and 6 were reacted together using reaction conditions analogous to those described in Example 18 step 1, but at a temperature of 100° C. for 2 hours, Compound No. 20 was obtained.

NMR Spectrum (d-6-DMSO, δ values) 0.00-0.08 (m, 2H), 0.20-0.30 (m, 2H), 2.19-2.32 (m, 1H), 3.30 (s, 2H), 3.32 (t, 1H), 3.64 (s, 3H), 4.19 (s, 2H), 4.67 (s, 2H), 6.60-6.75 (m, 4H), 6.75-6.88 (m, 2H), 7.07 (d, 2H), 7.10 (s, 1H), 7.50 (t, 1H), 7.60 (d, 1H), 7.86 (s, 1H), 8.55 (s, 1H), 10.60-10.70 (br.s, 1H).

Example 21

Preparation of Compound No. 21 in Table 2

4-(4-(2-methoxyphenoxy)-anilino)-3-cyano-6-methoxy-7-(3-chloropropoxy)quinoline (245 mg, 0.5 mmole) prepared as described in Example 18 step-3, was dissolved in 1-propanol with an excess (25 molar equivalents) of cyclopropylamine and heated at 60° C. for 72 hours. The reaction mixture was evaporated and the residue was chromatographed on a Bond Elut (10 g) cartridge eluting with a gradient of dichloromethane and dichloromethane containing 10% of methylamine (33% in ethanol) solution from 0% to 100%. Fractions containing product were evaporated and Compound No. 21 was obtained as the hydrochloride salt by treatment of the residue in ethanol with 1.0M hydrogen chloride (2 molar equivalents) in ether.

Mass Spectrum m/e 511 ($M^+$+H).

NMR Spectrum (d-6-DMSO, d values) 0.76 (m, 2H), 0.91 (m, 2H), 2.25 (m, 2H), 2.75 (m, 1H), 3.18 (m, 2H), 3.74 (s, 3H), 3.99 (s, 3H), 4.31 (t, 2H), 6.97 (m, 3H), 7.05 (m, 1H), 7.19 (m, 2H), 7.39 (d, 2H), 7.49 (s, 1H), 8.15 (s, 1H), 8.87 (s, 1H), 9.26 (broad, 2H), 11.00 (broad, 1H)

Example 22

Preparation of Compound No. 22 in Table 2

This compound was prepared using the following scheme.

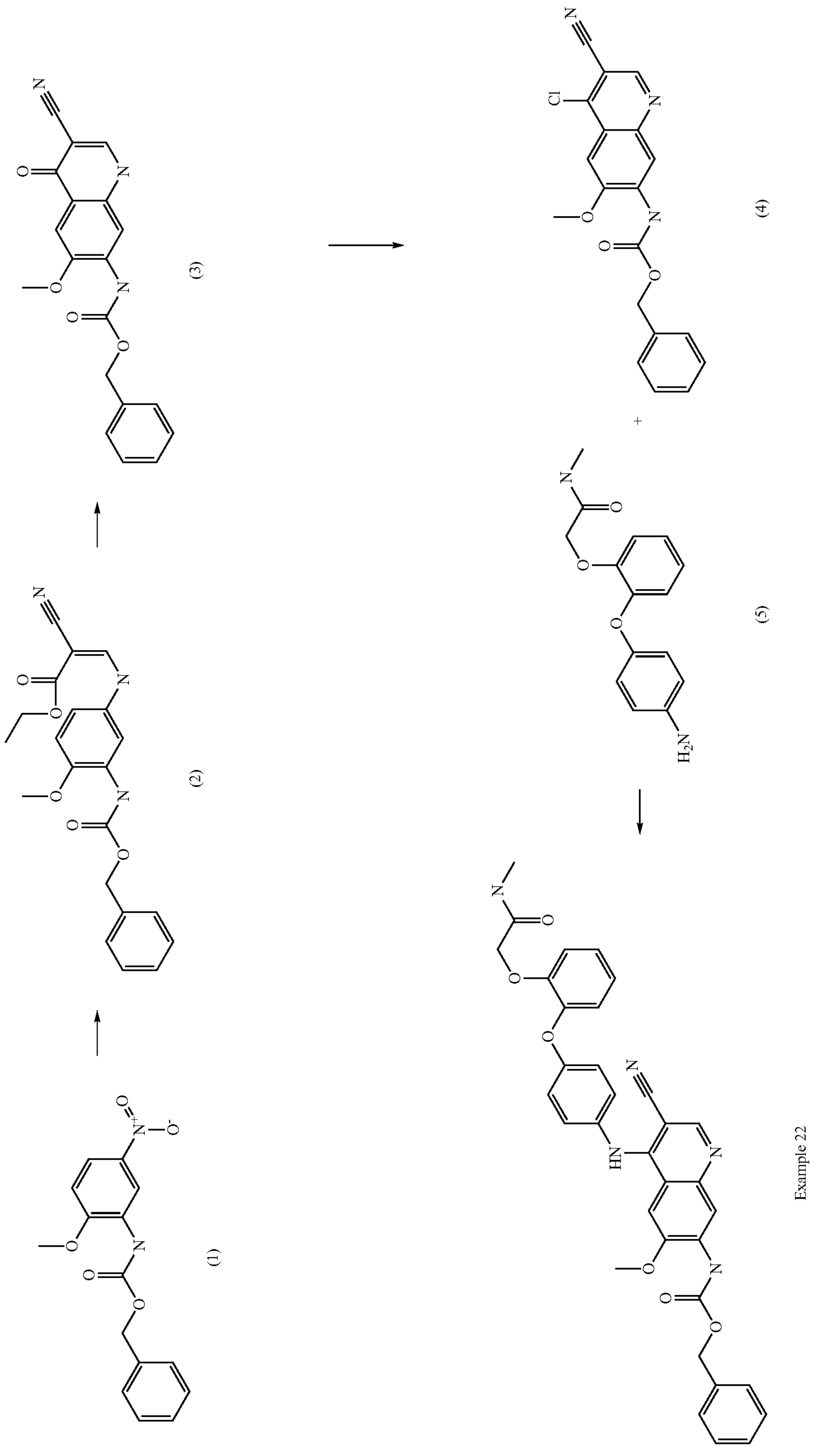
(1)
(2)
(3)
(4)
(5)
Example 22

Step 1

Intermediate (1) was obtained by reaction of benzylchloroformate (25.7 ml, 0.18 mol, 1.2 equiv.) and 2-methoxy-5-nitroaniline (25 g, 1.0 equiv.) in pyridine (190 ml) at room temperature for 18 hours.

NMR Spectrum (d-6-DMSO, δ values) 3.93 (s, 3H), 5.18 (s, 2H), 7.21 (d, 1H), 7.37 (m, 5H), 7.98 (m, 1H), 8.69 (m, 1H), 9.10 (s, 1H).

Step 2

Intermediate (2) was prepared by treating starting material (1) (28.7 g, 94.97 mmol, 1.0 equiv.) in ethyl acetate (550 ml) with $SnCl_2.2H_2O$ (85.7 g, 0.38 mol, 4 equiv.) at 105° C. for 5 hrs. After this, ethoxymethylenecyanoacetate (16.0 g, 95 mmol, 1.0 equiv.) in ethanol (200 ml) was added and the mixture held at 90° C. for 90 mins. The mixture was cooled, and Intermediate (2) was isolated by filtration, washed with ethanol and dried under vacuum.

NMR Spectrum (d-6-DMSO, δ values) (~3:1 mixture of isomers) 1.22 (m, 3H), 3.76 (s, 3H), 4.16 (m, 2H), 5.13 (s, 2H), 7.02 (m, 2H), 7.35 (m 5H), 7.72 (m, 0.25H), 7.80 (m, 0.75H), 8.14 (bs, 0.75H), 8.26 (d, 0.25H), 8.66 (s, 0.25H), 8.71 (s, 0.75H), 10.65 (d, 0.25H), 10.78 (bs, 0.75H).

Step 3

Intermediate (2) was converted to Intermediate (3) in the above scheme by contact with Dowtherm A for 4 hours at 250-260° C.

Mass Spectrum m/e 350 $(M+H)^+$.

Step 4

The product of Step 3 was halogenated using $POCl_3$ in MeCN at 110° C. for 2 hrs. Intermediate (4) in the above scheme was obtained.

Mass Spectrum m/e 368, 370 $(M+H)^+$.

Step 5

Intermediate (5) prepared as described in Example 19 step 1 was reacted with the product of step 4, using conditions analogous to those described in Example 18 step 1 but using temperatures of 100° C. for 90 mins. The title compound was obtained.

Mass Spectrum m/e 604 $(M+H)^+$.

NMR Spectrum (d-6-DMSO, δ values) 2.60 (d, 3H), 4.00 (s, 3H), 4.47 (2H, s), 5.24 (s, 2H), 7.03 (m, 5H), 7.12 (m, 2H), 7.37 (m, 5H), 7.46 (m, 2H), 7.53 (m, 1H), 8.13 (s, 1H), 8.58 (s, 1H), 8.79(s, 1H), 9.42 (s, 1H).

Example 23

Preparation of Compound No. 23 in Table 2

4-(4-(2-methoxyphenoxy)-anilino)-3-cyano-6-methoxy-7-(3-chloropropoxy)quinoline (245 mg, 0.5 mmole) prepared as described in Example 18 step 3, was dissolved in dimethylacetamide (5 ml) with an excess (5 molar equivalents) of hexamethyleneimine and sodium iodide (1 molar equivalent) and heated at 60° C. for 18 hours. At the end of this period, the reaction mixture was evaporated and the residue partitioned between water (5 ml) and ethyl acetate (10 ml). The aqueous phase was extracted with a further portion of ethyl acetate (3 ml) and the combined organic extracts were washed with water and brine then dried ($MgSO_4$) and evaporated. Compound 6 was purified by Bond Elut chromatography and converted to the hydrochloride salt by the procedure described in Example 21.

Mass Spectrum m/e 553 $(M^++H)$.

Example 24

Preparation of Compound No. 24 in Table 2

Using a method analogous to that described in Example 23 but with N-acetylpiperazine as the amine, the title compound was obtained.

Mass Spectrum m/e 583 $(M^++H)$.

Example 25

Preparation of Compound No. 25 in Table 2

Step 1

A solution of 4-(4-(2-methoxyphenoxy)-anilino)-3-cyano-6-methoxy-7-hydroxyquinoline (3.6 g, 8.0 mmole), prepared as described in Example 18 step 2, in DMSO (40 ml) was reacted with (2S)-(+)-glycidyl tosylate (2.3 g, 10 mmole) in the presence of potassium carbonate (2.8 g, 20 mmole) at room temperature for 18 hours. 4-(4-(2-methoxyphenoxy)-anilino)-3-cyano-6-methoxy-7-glycidyloxy quinoline was obtained.

Mass Spectrum m/e 470 $(M^++H)$

Step 2

The product from step 1 together with 20 molar equivalents of morpholine and 0.5 molar equivalents NaI in dimethyl acetamide were heated to 60° C. for 18 hours to yield the title compound.

Mass Spectrum m/e 557 $(M^++H)$.

NMR Spectrum (d-6-DMSO, δ values at 373K) 3.37 (m, 6H), 3.80 (s, 3H), 3.96 (m, 4H), 4.02 (s, 3H), 4.28 (m, 2H), 4.57 (m, 1H), 6.99 (m, 3H), 7.06 (d, 1H), 7.19 (m, 2H), 7.34 (d, 2H), 7.59 (s, 1H), 8.06 (s, 1H), 8.63 (s, 1H), 10.28 (broad, 1H)

Example 26

Preparation of Compound No. 26 in Table 2

4-(4-(2-methoxyphenoxy)-anilino)-3-cyano-6-methoxy-7-(3-chloropropoxy)quinoline (107.5 mg, 0.22 mmole), prepared as described in Example 18 step 3 was reacted with 4-amidopiperidine (44 molar equivalents) and 1 molar equivalent sodium iodide in N,N-dimethylacetamide (3 ml). The mixture was heated to 50° C. for 20 hours after which the title compound was isolated as the hydrochloride salt using the work up and salt formation procedure described in Example 18, step 4.

Mass Spectrum m/e 582 $(M^++H)$.

NMR Spectrum (d-6-DMSO, δ values) 2.00 (m, 4H), 2.33 (m, 2H), 3.10 (m, 2H), 3.30 (t, 2H), 3.55 (m, 2H), 3.77 (s, 3H), 3.98 (s, 3H), 4.33 (t, 2H), 6.97 (m, 3H), 7.03 (d, 1H), 7.15 (m, 2H), 7.32 (m, 2H), 7.54 (s, 1H), 8.19 (s, 1H), 8.88 (s, 1H), 10.14 (broad, 1H), 11.07 (broad, 1H)

Example 27

Preparation of Compound 27 in Table 2

Step 1

4-nitro-fluorobenzene and 2-(carboxymethoxy)phenol were reacted together in DMA in the presence of potassium butoxide for 2 hours at 150° C. to yield 4-(2-(carboxymethoxy)phenoxy)nitrobenzene.

Mass Spectrum m/e 288 $(M-H^+)^-$

Step 2

Reduction of the product of step 1 and concomitant esterification was effected by hydrogenation in EtOAc/MeOH/1M HCl at room temperature for 18 hours which gave the corresponding methyl ester, 4-(2-methoxycarbonylmethoxy)phenoxy)aniline.

Mass Spectrum m/e 274 $(M+H)^+$

Step 3

Reacting the product of step 2 in methanol with cyclopropylamine at room temperature for 3 hours resulted in the production of 4-(2-(cyclopropyl-amido-methoxy)-phenoxy) aniline of formula

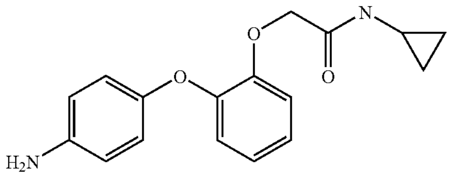

Mass Spectrum m/e 299.5 (M+H)+

Step 4

Using a method analogous to that described in Example 20 but using the product of step (3) in place of the product of Step 6 of Example 20, the title compound was obtained.

NMR Spectrum (d-6-DMSO, δ values) 0.00-0.08 (m, 2H), 0.17-0.28 (m, 2H), 2.20-2.30 (m, 1H), 3.26 (t, 1H), 3.60 (s, 3H), 4.05 (s, 2H), 4.64 (s, 2H), 6.55-6.71 (m, 5H), 6.71-6.81 (m, 1H), 7.03 (d, 2H), 7.09 (s, 1H), 7.40 (d, 1H), 7.88 (s, 1H), 8.53 (s, 1H), 10.71-10.78 (br.s, 1H).

Example 28

Preparation of Compound 28 in Table 2

The compound in this instance was prepared using the following scheme:

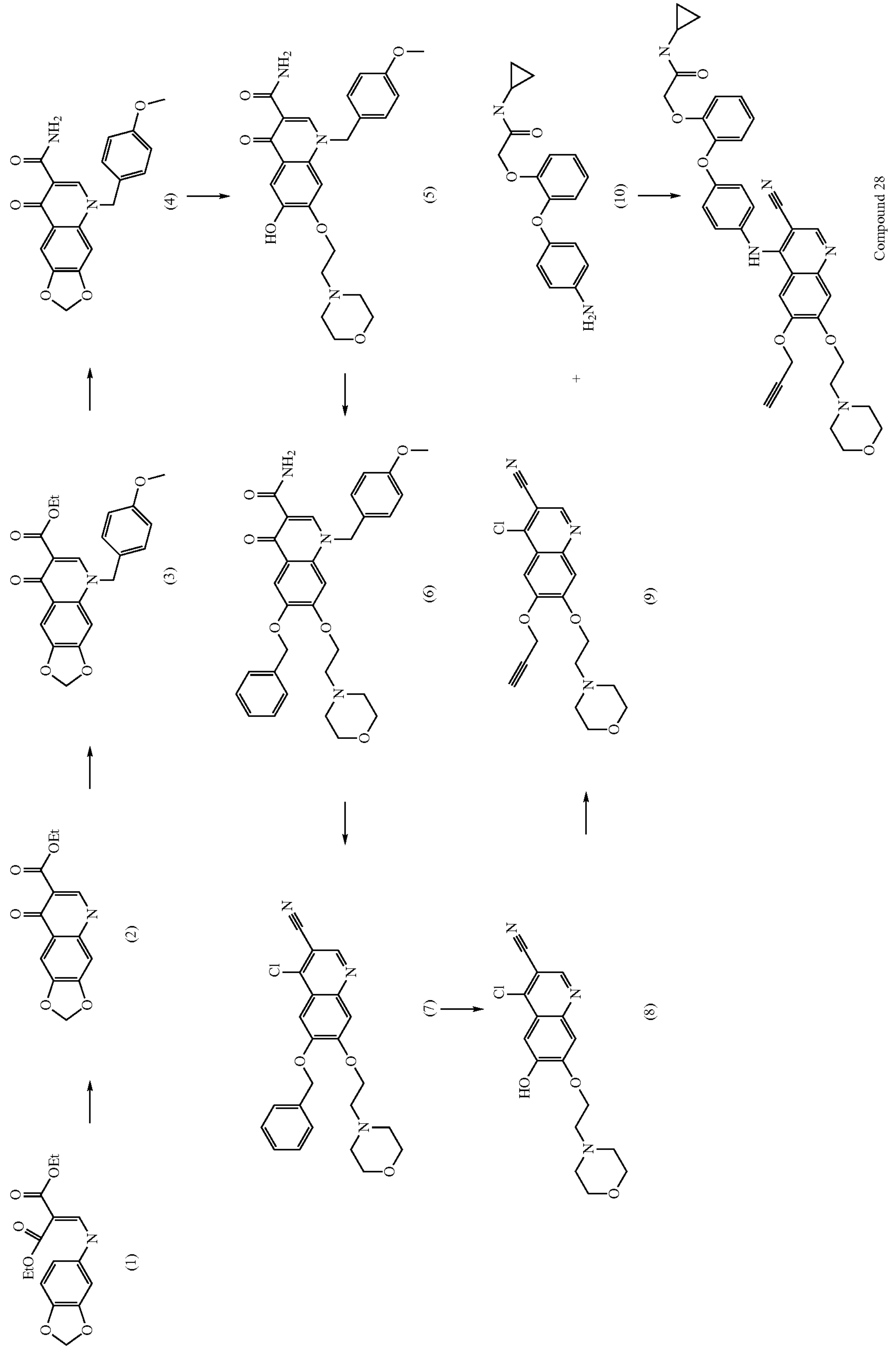
Compound 28

Step 1

Intermediate (1) was prepared by reacting together methylenedioxyaniline (51 g, 0.37 mol) and diethylethoxymethylenemalonate (75.1 ml, 0.37 mol) in ethanol at 80° C. for 1 hour.

NMR Spectrum (d-6-DMSO, δ values) 1.30(t, 3H), 1.37 (t, 3H), 4.22 (q, 2H), 4.29 (q, 2H), 6.99 (s, 2H), 6.56 (m, 1H), 6.66 (d, 1H), 6.79 (d, 1H), 8.37 (d, 1H), 10.94 (bd, 1H).

Step 2

The product of step 1 was converted to Intermediate (2) above by contact with Dowtherm A for 1 hour at 250-260° C.

NMR Spectrum (d-6-DMSO, δ values) 1.24 (t, 3H), 4.17 (q, 2H), 6.13 (s, 2H), 7.03 (s, 1H), 7.43 (s, 1H), 8.49 (s, 1H).

Step 3

Reaction of the product of step (2) (20.3 g,) with 4-methoxybenzylchloride (11.9 ml, 81.6 mmol) in DMA (200 ml) in the presence of potassium carbonate for 3 hours at 100° C. yielded Intermediate 3

Mass Spectrum m/e 382 $(M+H)^+$.

Step 4

The product of step 3 mixed with formamide (91.8 mmol, 3.5 equiv.) in DMA was heated at 60° C. Sodium methoxide (25% in methanol, 3.9 ml, 0.65 equiv.) added and heating of the mixture continued for 90 mins to yield Intermediate 4 in the above scheme.

Mass Spectrum m/e 353 $(M+H)^+$.

Step 5

The product of step 4 was mixed with 2-hydroxyethylmorpholine, potassium (tert)-butoxide and DMA and the mixture heated at 120° C. for 25 mins. Intermediate (5) was obtained.

Mass Spectrum m/e 454 $(M+H)^+$.

Step 6

Intermediate (5) was mixed with benzylalcohol, $PPh_3$ in DCM and DEAD added, and the mixture allowed to react at room temperature for 18 hrs. Intermediate 6 was isolated.

Mass Spectrum m/e 544 $(M+H)^+$.

Step 7

The product of step 6 was then reacted with $POCl_3$ in MeCN for 15 hours at 110° C. to yield Intermediate 7 in the above scheme.

Mass Spectrum m/e 424, 426 $(M+H)^+$.

Step 8

Futher processing of Intermediate (7) using reaction conditions analogous to those described in Example 18 step 2 but with a temperature of 80° C. held for 18 hrs produced Intermediate 8.

Mass Spectrum m/e 334, 336 $(M+H)^+$.

Step 9

Intermediate (9) was produced by reacting the product of step 8 with propargylbromide using conditions analogous to those described in Example 20 step 2. The reaction was carried out over 18 hours at room temperature.

Mass Spectrum m/e 372, 374 $(M+H)^+$.

Step 10

Intermediate (10) prepared as described in Example 27 step 3 was reacted with Intermediate (9) above using conditions analogous to those described in Example 18 step 1 but maintaining the reaction mixture at 100° C. for 3 hrs. The title compound was obtained.

Mass Spectrum m/e 634 $(M+H)^+$.

NMR Spectrum (d-6-DMSO+d-4-AcOH, 6 values) 0.40 (m, 2H), 0.60 (m, 2H), 1.84 (m, 1H), 2.61 (m, 2H), 3.68 (m, 3H), 3.87 (m, 2H), 4.42 (s, 2H), 4.64 (m, 2H), 4.99 (m, 2H), 7.02 (m, 5H), 7.14 (m, 1H), 7.38 (d, 2H), 7.35 (s, 1H), 8.16 (s, 1H), 8.81 (s, 1H).

Example 29

Preparation of Compound No. 29 in Table 2

Using a method analogous to that described in Example 23 but with 2-(N,N-dimethylamido)-pyrrolidine as the amine, the title compound was obtained.

Mass Spectrum m/e 596 $(M^++H)$.

Example 30

Preparation of Compound 30 in Table 2

The title compound was obtained using a method analogous to that described in Example 25 but with dimethylamine used instead of morpholine in step 2.

Mass Spectrum m/e 515 $(M^++H)$.

NMR Spectrum (d-6-DMSO, δ values) 2.87 (m, 6H), 3.32 (m, 2H), 3.76 (s, 3H), 4.01 (s, 3H), 4.21 (d, 2H), 4.45 (m, 1H), 6.17 (broad, 1H), 6.99 (m, 3H), 7.08 (m, 1H), 7.21 (m, 2H), 7.41 (m, 2H), 7.60 (s, 1H), 8.23 (s, 1H), 8.89 (s, 1H), 9.90 (broad, 1H), 11.10 (broad, 1H)

Example 31

Preparation of Compound No. 31 in Table 2

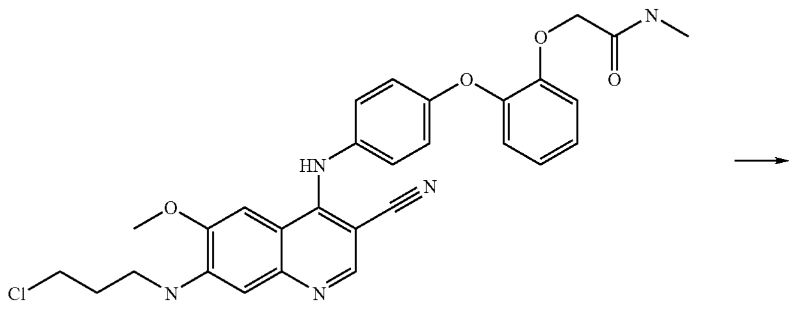

(1)

-continued

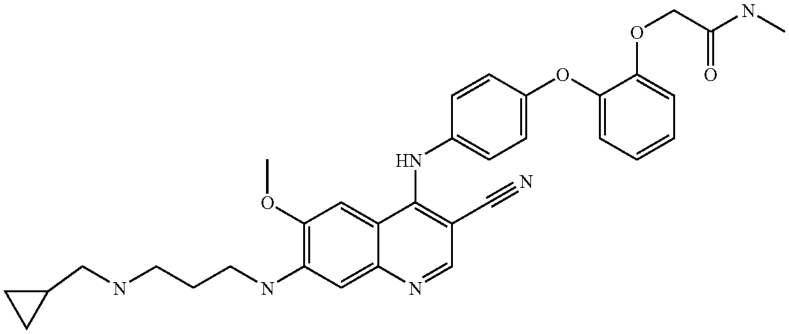

Example 31

The title compound was prepared using a method analogous to that described in Example 19 above except that cyclopropylmethylamine was used as the amine in step 3 and the reaction was allowed to proceed over 9 days.

Mass Spectrum m/e 581 $(M+H)^+$.

NMR Spectrum (d-6-DMSO, δ values) 0.37 (m, 2H), 0.58 (m, 2H), 1.07 (m, 1H), 2.04 (m, 2H), 2.65 (d, 3H), 2.82 (m, 2H), 3.00 (m, 2H), 4.03 (s, 3H), 4.47 (s, 2H), 6.95 (s, 1H), 7.05 (m, 4H), 7.17 (m, 3H), 7.41 (d, 2H), 7.58 (m, 1H), 7.95 (s, 1H), 8.82 (s, 1H), 8.91 (bs, 1H).

Example 32

Preparation of Compound No. 32 in Table 2

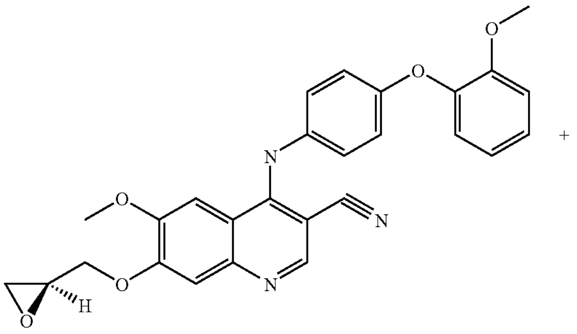

(1)

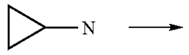

(2)

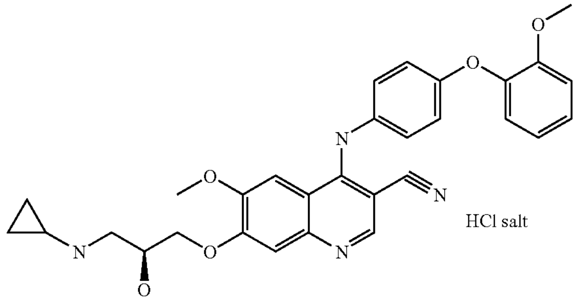

Example 32

The title compound was prepared from intermediate (1) by reacting with 20 molar equivalents of cyclopropylamine at a temperature of 60° C. for 18 hr in dimethyl acetamide.

Mass Spectrum m/e 527 $(M^+ +H)$

NMR Spectrum (d-6-DMSO, δ values) 0.83 (m, 2H), 1.01 (m, 2H), 2.84 (m, 1H), 3.22 (m, 1H), 3.82 (s, 3H), 4.06 (s, 3H), 4.29 (d, 2H), 4.44 (m, 1H), 7.04 (m, 3H), 7.13 (m, 1H), 7.27 (m, 2H), 7.46 (d, 2H), 7.60 (s, 1H), 8.24 (s, 1H), 8.94 (s, 1H), 9.16 (broad, 1H), 9.25 (broad, 1H), 11.08 (broad, 1H)

Intermediate (1)

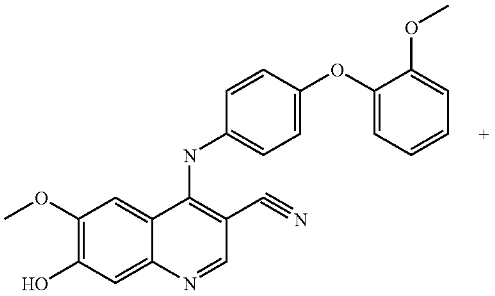

(B1)

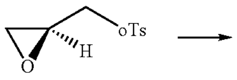

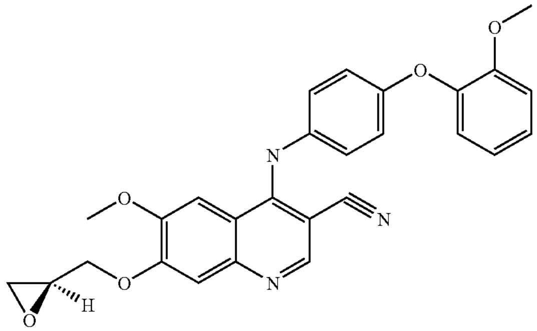

(1)

Intermediate (1) was prepared by reacting Intermediate (B3) with (2S)-(+)-Glycidyl tosylate in the presence of anhydrous potassium carbonate at room temperature for 72 hours in DMSO.

Mass Spectrum m/e 470 $(M^+ +H)$

Example 33

Preparation of Compound No. 33 in Table 2

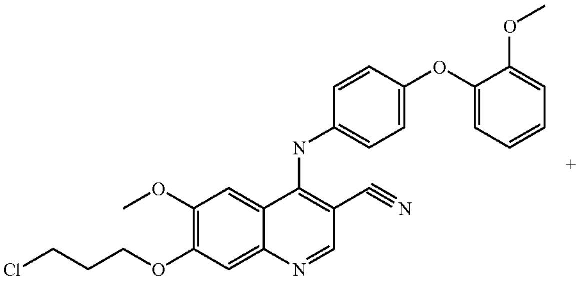

(1)

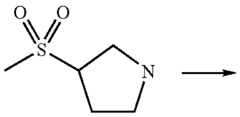

(2)

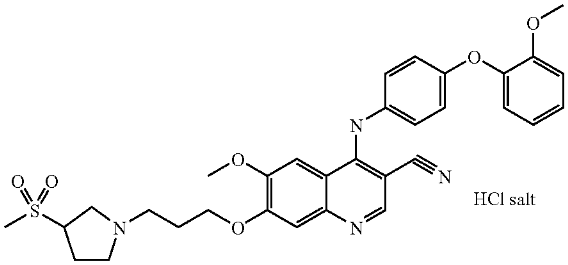

Example 33

The title compound was prepared by reacting Intermediate (1) with 1 molar equivalent NaI, 5 molar equivalents anhydrous potassium carbonate and 5 molar equivalents 3-(methylsulfonyl)pyrrolidine (2) at a temperature of 60° C. for 18 hours in dimethyl acetamide.

Mass Spectrum m/e 603 ($M^+$+H)

NMR Spectrum (d-6-DMSO, δ values, 373K) 2.32 (m, 2H), 3.10 (s, 3H), 3.34 (m, 8H), 3.77 (s, 3H), 3.98 (s, 3H), 4.18 (m, 1H), 4.34 (t, 2H), 6.97 (m, 3H), 7.05 (m, 1H), 7.17 (m, 2H), 7.31 (d, 2H), 7.51 (s, 1H), 8.01 (s, 1H), 8.61 (s, 1H), 10.17 (broad, 1H)

Intermediate (1)

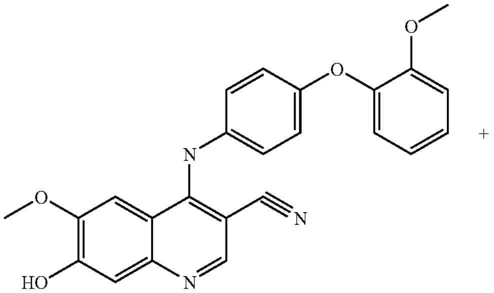

(B1)

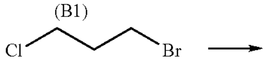

-continued

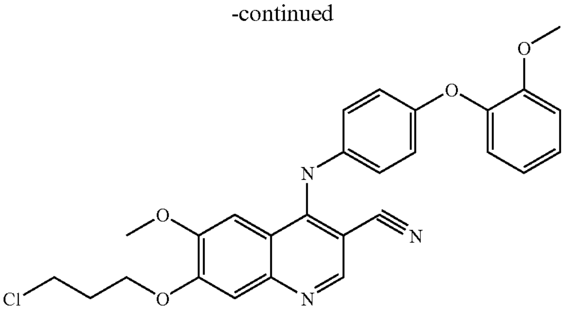

(1)

Intermediate (1) was prepared by reacting Intermediate (B3) with 1-chloro-3-bromopropane at room temperature for 18 hours in the presence of KO$^t$BU (1.0M in THF) in DMSO Mass Spectrum m/e 490 ($M^+$+H)

Example 34

Preparation of Compound No. 34 in Table 2

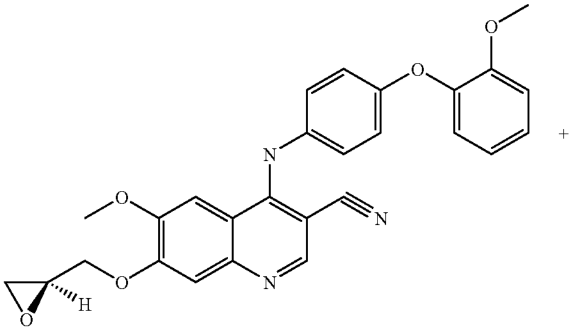

(1)

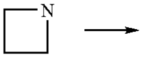

(2)

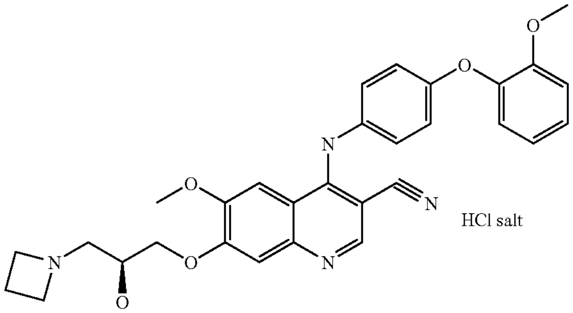

Example 34

The title compound was prepared by reacting Intermediate (1) with 5 molar equivalents of azetidine at a temperature of 60° C. or 20 hours in dimethyl acetamide.

Mass Spectrum m/e 527 ($M^+$+H)

NMR Spectrum (d-6-DMSO, δ values) 2.19 (m, 1H), 3.09 (m, 1H), 3.33 (m, 3H), 3.74 (s, 3H), 3.76 (m, 1H), 3.97 (s, 3H), 4.13 (m, 4H), 4.20 (m, 1H), 5.91 (broad, 1H), 6.97 (m, 3H), 7.05 (m, 1H), 7.19 (m, 2H), 7.34 (d, 2H), 7.47 (s, 1H), 8.05 (s, 1H), 8.73 (s, 1H), 8.88 broad doublet, 1H), 10.26 (broad, 1H), 10.57 (broad, 1H)

Intermediate (1)

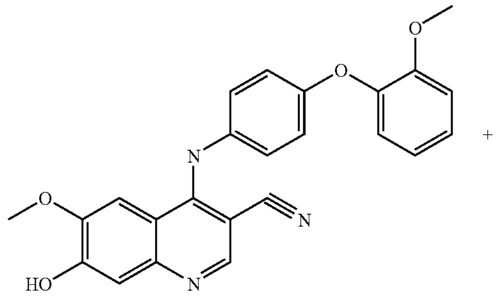

(B1)

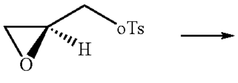

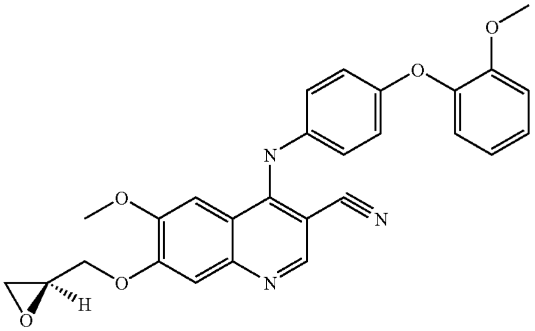

(1)

Intermediate (1) was prepared by reacting Intermediate (B3) with (2S)-(+)-Glycidyl tosylate in the presence of anhydrous potassium carbonate in DMSO at room temperature for 72 hours.

Mass Spectrum m/e 470 ($M^{+}$+H)

Example 35

Preparation of Compound No. 35 in Table 2

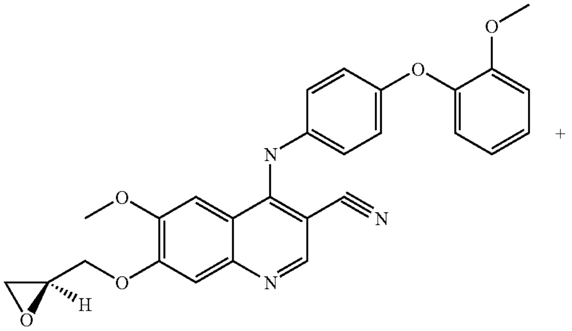

(1)

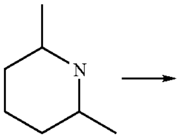

(2)

-continued

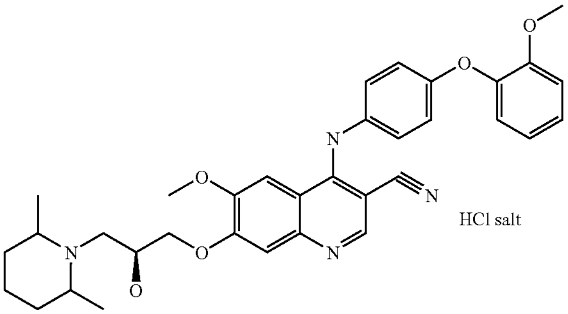

Example 35

The title compound was prepared by reacting the Intermediate (1) with 5 molar equivalent of 2,6-dimethylpiperidine at a temperature of 60° C. for 20 hours in dimethyl acetamide.

Mass Spectrum m/e 583 ($M^{+}$+H)

NMR Spectrum (d-6-DMSO, δ values, 373K) 1.35 (s, 2H), 1.50 (m, 4H), 1.71 (m, 6H), 3.45 (m, 2H), 3.77 (s, 3H), 3.98 (s, 3H), 4.27 (m, 2H), 4.47 (m, 1H), 6.96 (m, 3H), 7.03 (m, 1H), 7.17 (m, 2H), 7.29 (d, 2H), 7.48 (s, 1H), 7.96 (s, 1H), 8.57 (s, 1H), 9.78 (broad, 2H)

Intermediate (1)

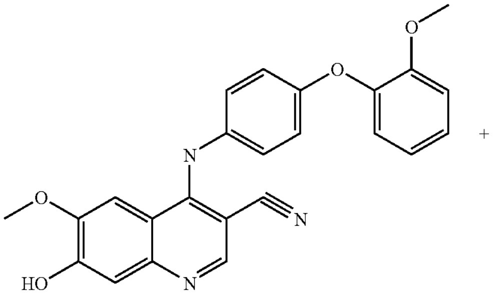

(B1)

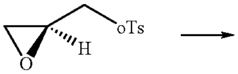

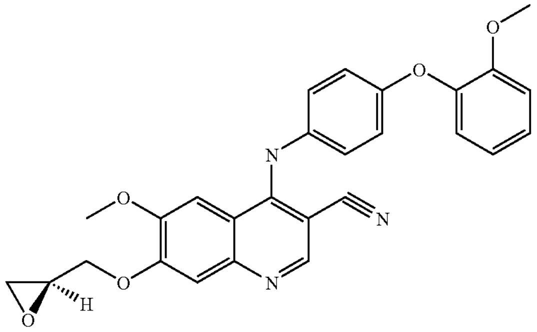

(1)

Intermediate (1) was prepared by reacting Intermediate (B3) with (2S)-(+)-Glycidyl tosylate in the presence of anhydrous potassium carbonate at room temperature for 72 hours in DMSO.

Mass Spectrum m/e 470 ($M^{+}$+H)

Example 36

Preparation of Compound No. 36 in Table 2

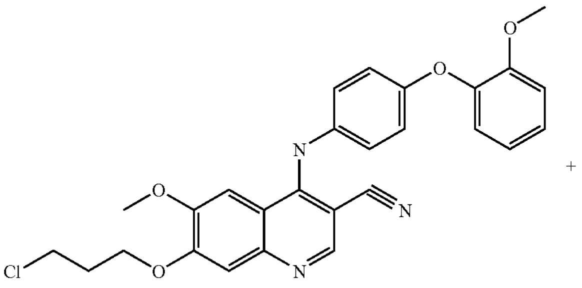

(1)

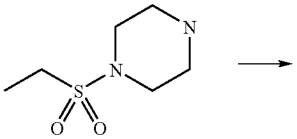

(2)

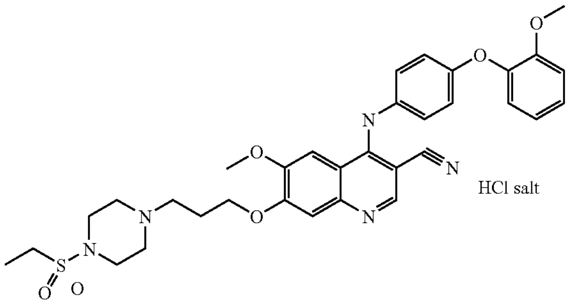

Example 36

The title compound was prepared by reacting Intermediate (1) with 6 molar equivalents 1-(ethylsulfonyl)piperazine (2) in the presence of 1 molar equivalent NaI and 5 molar equivalents anhydrous potassium carbonate at a temperature of 60° C. for 18 hours in dimethyl acetamide.

Mass Spectrum m/e 632 ($M^+$+H)

NMR Spectrum (d-6-DMSO, δ values) 1.19 (t, 3H), 1.96 (m, 2H), 2.44 (m, 6H), 3.03 (q, 2H), 3.17 (m, 4H), 3.74 (s, 3H), 3.90 (s, 3H), 4.18 (t, 2H), 6.91 (m, 3H), 7.02 (m, 1H), 7.17 (m, 2H), 7.24 (d, 2H), 7.30 (s, 1H), 7.73 (s, 1H), 8.37 (s, 1H), 9.38 (s, 1H)

Intermediate (1)

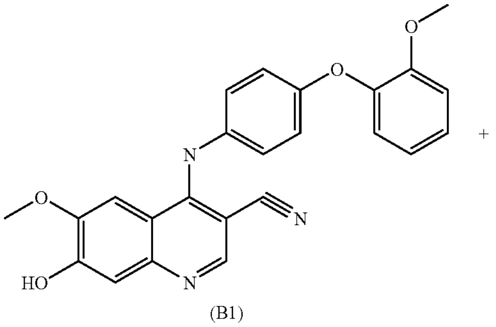

(B1)

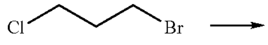

-continued

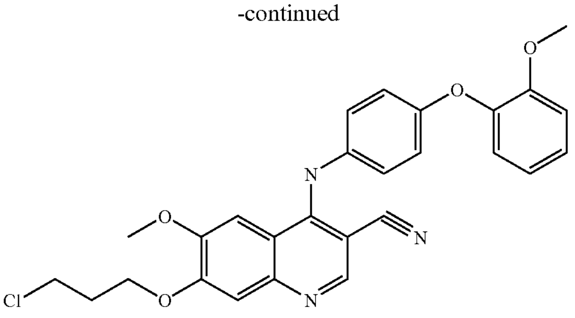

(1)

ermediate (1) was prepared by reacting Intermediate (B3) with 1-chloro-3-bromopropane in the presence of $KO^tBU$ (1.0M in THF) at room temperature for 18 hours in DMSO.

Mass Spectrum m/e 490 ($M^+$+H)

Example 37

Preparation of Compound No. 37 in Table 2

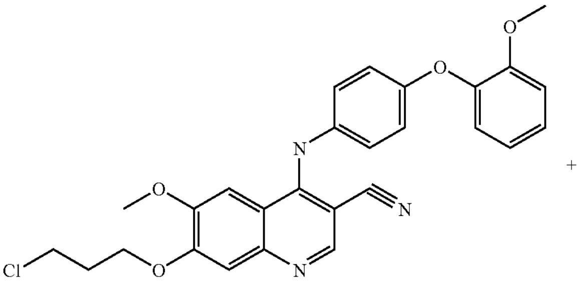

(1)

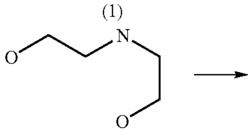

(2)

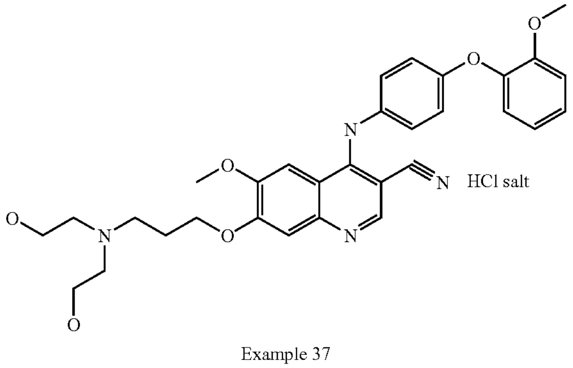

Example 37

The title compound was prepared by reacting Intermediate (1) with 6 molar equivalents N-(2-hydroxyethyl)-2-hydroxyethylamine (2) in the presence of 1 molar equivalent NaI and 5 molar equivalents anhydrous potassium carbonate at a temperature of 60° C. for 18 hours in dimethyl acetamide.

Mass Spectrum m/e 559 ($M^+$+H)

NMR Spectrum (d-6-DMSO, δ values) 2.31 (m, 2H), 3.29 (m, 4H), 3.37 (m, 2H), 3.72 (s, 3H), 3.78 (m, 4H), 3.99 (s, 3H), 4.27 (t, 2H), 6.93 (m, 3H), 7.04 (m, 1H), 7.17 (m, 2H), 7.38 (d, 2H), 7.57 (s, 1H), 8.24 (s, 1H), 8.87 (s, 1H), 9.93 (broad, 1H)

Intermediate (1)

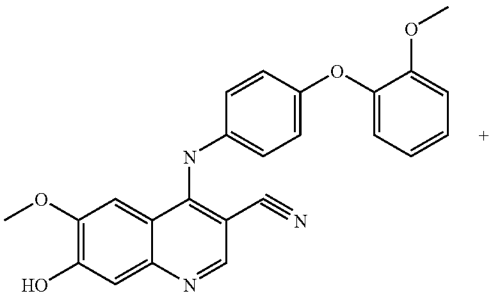

(B1)

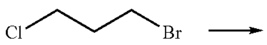

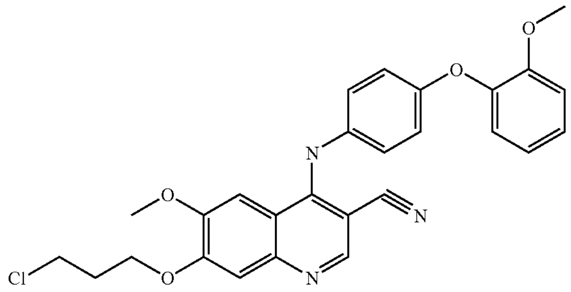

(1)

Intermediate (1) was prepared by reacting Intermediate (B3) with 1-chloro-3-bromopropane in the presence of KO$^{t}$Bu (1.0M in THF) at room temperature for 18 hours in DMSO.

Mass Spectrum m/e 490 ($M^{+}$+H)

Example 38

Preparation of Compound No. 38 in Table 2

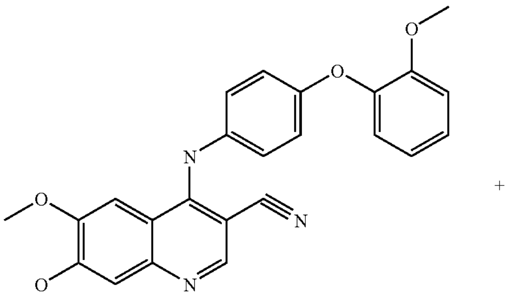

(B1)

-continued

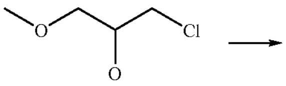

(2)

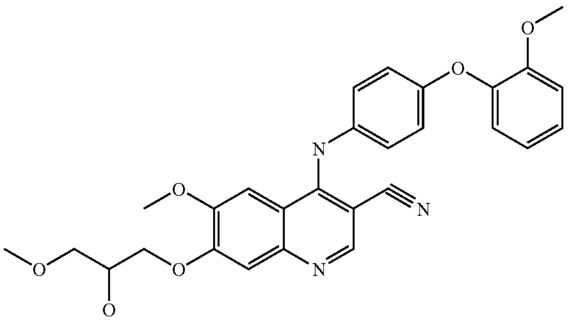

Example 38

The title compound was prepared by reacting Intermediate (B3) with 1.2 molar equivalents 1-chloro-3-methoxypropan-2-ol (2) in the presence of 2.2 molar equivalents anhydrous potassium carbonate at a temperature of 65° C. for 66 hr followed by a temperature of 85° C. for 24 hours in dimethyl formamide.

Mass Spectrum m/e 502 ($M^{+}$+H)

Example 39

Preparation of Compound No. 39 in Table 2

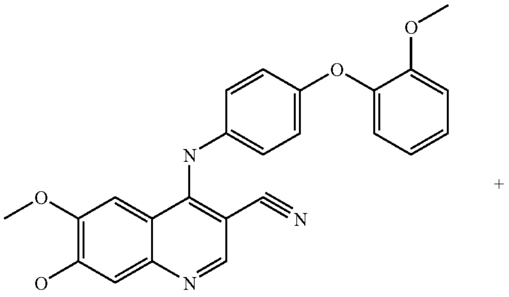

(1)

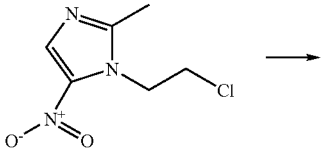

(2)

-continued

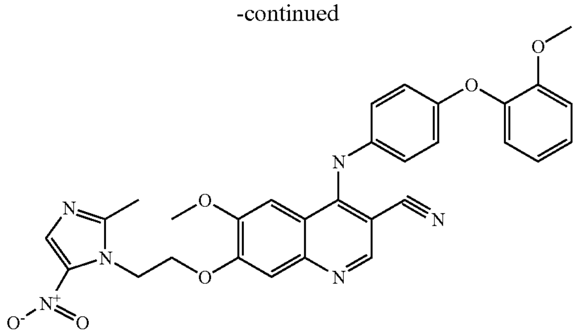

Example 39

The title compound was prepared by reacting Intermediate (B3) with 1.2 molar equivalents 1-(2-chloroethyl)-2-methyl-5-nitro-1H-imidazole (2) in the presence of 2.2 molar equivalents anhydrous potassium carbonate at a temperature of 65° C. for 66 hours followed by 85° C. for 24 hours in dimethyl formamide.

Mass Spectrum m/e 567 ($M^+$+H)

Example 40

Preparation of Compound No. 40 in Table 3

The title compound was prepared according to the following scheme:

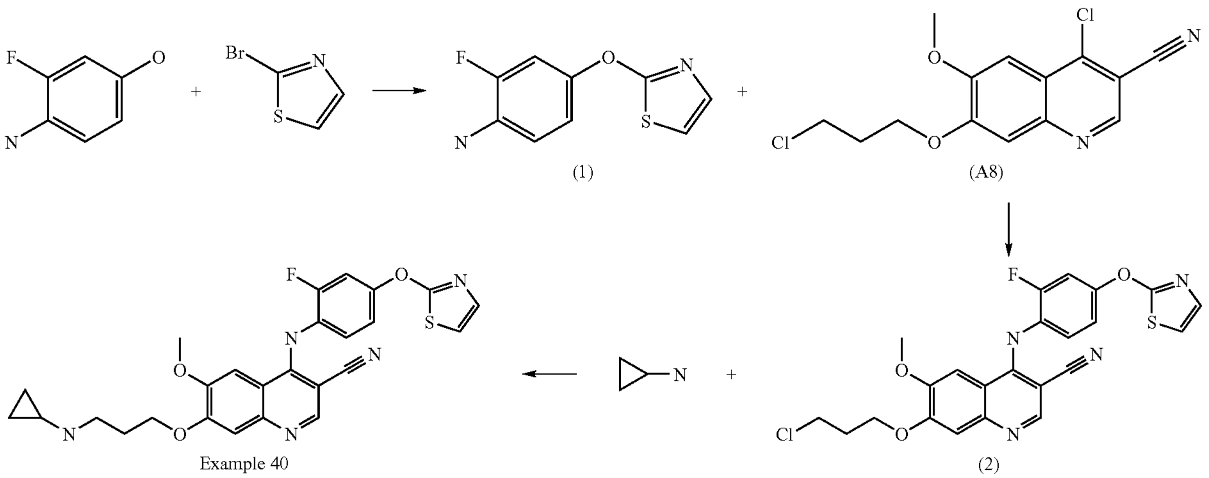

(1)

(A8)

Example 40

(2)

In the final step the title compound was prepared by reaction of Intermediate (2) with cyclopropylamine in the presence of NaI at temperature of 50° C. for 24 hr.

Mass Spectrum m/e 506 ($M^+$+H)

NMR Spectrum (d-6-DMSO, δ values) 0.75 (d, 2H), 0.9 (br s, 2H), 2.2 (m, 2H), 2.75 (br s, 1H), 3.2 (br s, 2H), 4.0 (s, 3H), 4.3 (m, 2H), 7.35 (m, 3H), 7.55 (s, 1H), 7.6 (d, 1H), 7.65 (t, 1H), 8.3 (s, 1H), 8.9 (s, 1H), 9.4 (br s, 2H)

Intermediate (1)

Intermediate (1) was prepared by reaction of 2-bromothiazole and 4-amino-3-fluorophenol in the presence of KOtBu at a temperature of 150° C. for 1 hr in dimethylacetamide.

Mass Spectrum m/e 211 ($M^+$+H)

Intermediate (2)

Intermediate (2) was prepared by reaction of Intermediate (1) with Intermediate (A8) at a temperature of 110° C. for 5 hr in n-propanol.

Mass Spectrum m/e 485 ($M^+$+H)

Example 41

Preparation of Compound No. 41 in Table 3

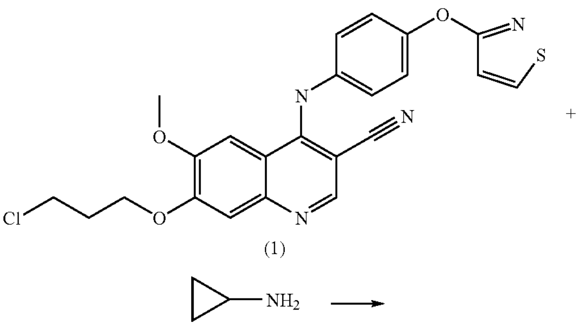

(1)

-continued

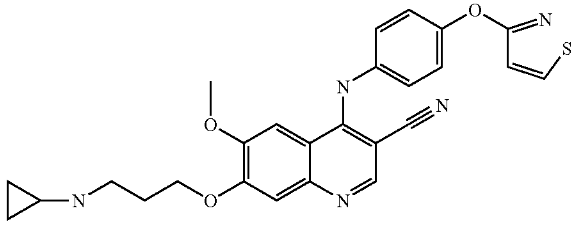

Example 41

The title compound was prepared by reaction of Intermediate (1) with cyclopropylamine in the presence of sodium iodide at 50° C. for 24 hours.

Mass Spectrum m/e 488 ($M^{+}$+H)

NMR Spectrum (d-6-DMSO, δ values) 0.7 (m, 2H), 0.9 (m, 2H), 2.25 (m, 2H), 2.7 (m, 1H), 3.15 (m, 2H), 4.0 (s, 3H), 4.3 (t, 2H), 6.9 (d, 1H), 7.35 (d, 2H), 7.5 (d, 2H), 7.6 (s, 1H), 8.3 (s, 1H), 8.9 (s, 1H), 9.05 (d, 1H), 9.4 (br s, 2H), 11.4 (br s, 1H)

Intermediate (1)

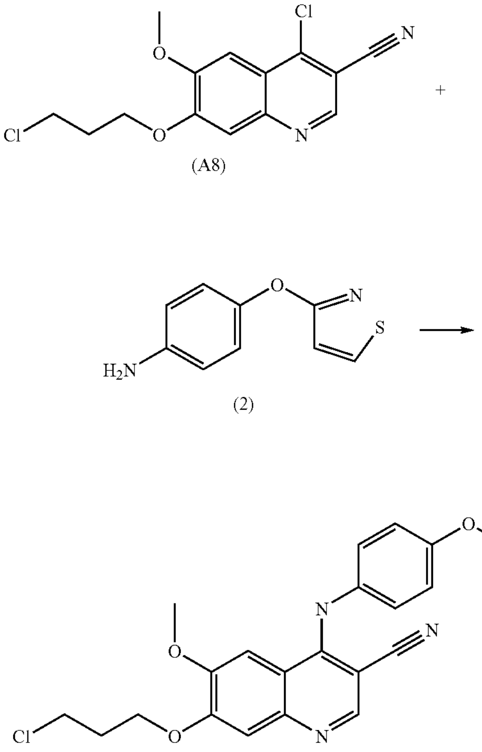

(A8) (2) (1)

Intermediate 1

Intermediate (1) was prepared by reaction of Intermediate (A8) with Intermediate (2) in n-propanol at a temperature of 110° C. for 5 hours.

Mass Spectrum m/e 467 ($M^{+}$+H)

Intermediate (2) was prepared according to the following scheme:

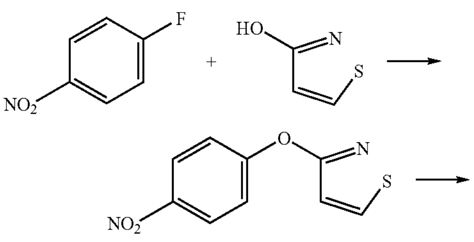

(3)

-continued

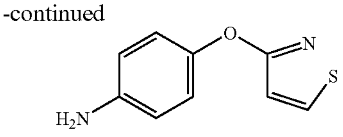

(2)

Intermediate (3)

1-Fluoro-4-nitrobenzene was reacted with 3-hydroxy-isothiazole in the presence of KOtBu in dimethylacetamide at a temperature of 150° C. for 1 hour.

Intermediate 2

Intermediate (2) was prepared by the reduction of Intermediate (3) using palladium over carbon in ethyl acetate for 36 hours Mass Spectrum m/e 193 ($M^{+}$+H)

Example 42

Preparation of Compound No. 42 in Table 4

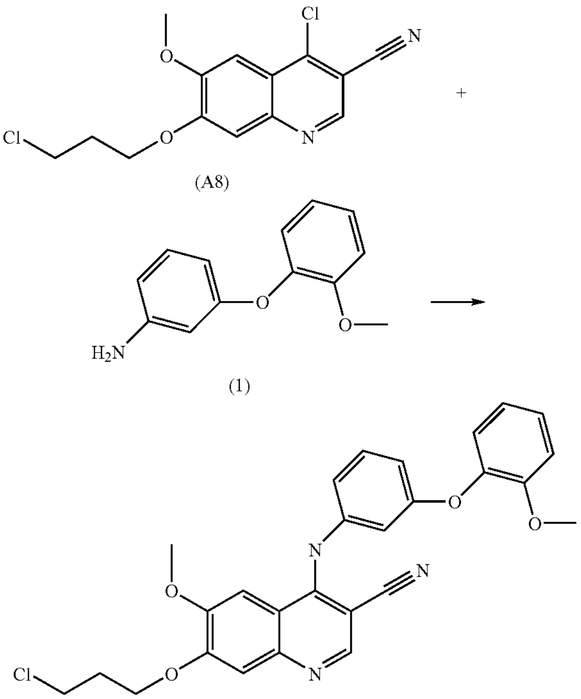

(A8) (1) Example 42

4-chloro-7-(3-chloropropoxy)-6-methoxyquinoline-3-carbonitrile (900 mg, 2.9 mmol) and 3-(2-methoxyphenoxy)aniline (Reference: WO 2001056990) were heated together in n-propanol for 4 hours. The resulting solid was filtered and washed first with cold n-propanol and then with diethyl ether and then dried in vacuo to leave a solid (1.22 g, 80%).

Mass Spectrum ES 488 (MH−) 490 (MH+)

H NMR spectrum (300 MHz, DMSO): 2.22-2.32 (m, 2H), 3.74 (s, 3H), 3.83 (t, 2H), 3.97 (s, 3H), 4.30 (t, 2H), 6.90 (m, 2H), 6.98 (dd, 1H), 7.10 (m, 2H), 7.14-7.22 (m, 2H), 7.41 (t, 1H), 7.48 (s, 1H), 8.04 (s, 1H), 8.90 (s, 1H), 10.6 (br s, 1H).

Intermediate (1)

This prepared by a method analogous in Intermediate (B2) in Preparation B above.

Example 43

Preparation of Compound No. 43 in Table 4

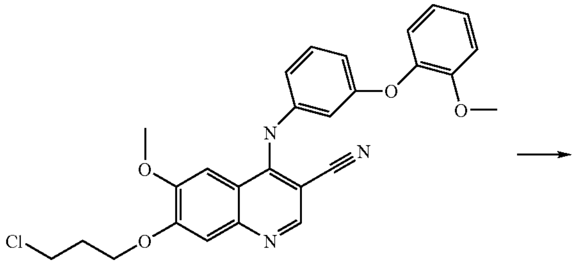

Example 42

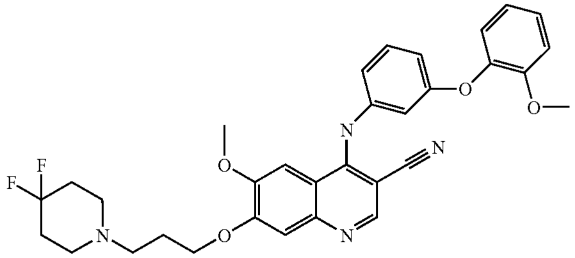

Example 43

7-(3-chloropropoxy)-6-methoxy-4-{[3-(2-methoxyphenoxy)phenyl]amino}quinoline-3-carbonitrile (200 mg, 0.41 mmol) [Example 42] and 4,4-difluoropiperidine (200 mg, 1.8 mmol) and sodium iodide (184 mg, 1.23 mmol) were heated in dimethylacetamide (10 ml) at 40 C for 12 hours. The reaction was evaporated and the residue was partitioned between dichloromethane and water. The organic layer was separated and the aqueous layer re-extracted with dichloromethane. The organics were combined, dried over magnesium sulfate, filtered and then evaporated in vacuo to leave a gum. The crude product was triturated with diethyl ether to leave the title compound as a solid (28 mg, 12%).

H NMR spectrum (400 MHz DMSO+acetic acid at 373K) 2.19 (m, 6H), 3.12 (m, 6H), 3.79 (s, 3H), 3.90 (s, 3H), 4.28 (t, 2H), 6.73 (m, 2H), 6.88 (d, 1H), 6.95 (m, 1H), 7.08 (d, 1H), 7.15 (m, 2H), 7.32 (t, 1H), 7.43 (s, 1H), 7.65 (s, 1H), 8.50 (s, 1H).

Mass Spectrum ES 575 (MH+)

Example 44

Preparation of Compound No. 44 in Table 4

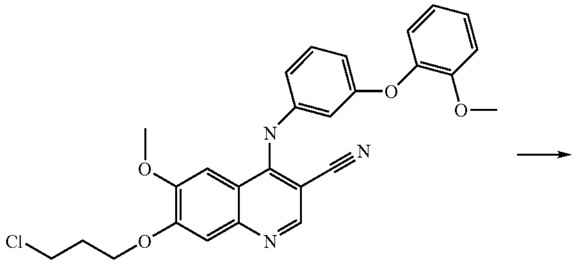

Example 42

-continued

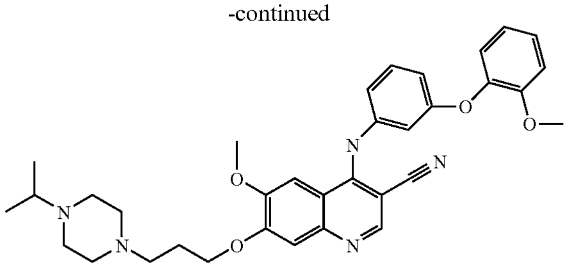

Example 44

7-(3-chloropropoxy)-6-methoxy-4-{[3-(2-methoxyphenoxy)phenyl]amino}quinoline-3-carbonitrile (200 mg, 0.41 mmol) was dissolved in 1-isopropylpiperazine (2 ml) and heated at 45 C for 12 hours. The reaction mixture was partitioned between dichloromethane and water. The organic layer was separated and the aqueous layer re-extracted with dichloromethane. The organics were combined, dried over magnesium sulfate, filtered and then evaporated in vacuo. The residue was purified by flash chromatography, eluting over a gradient from dichloromethane to 10% methanol in dichloromethane to give an orange oil. The oil was triturated in hexane leave the title compound as a solid (91 mg, 38%).

H NMR spectrum (300 MHz. $CDCl_3$) 1.08 (d, 6H), 2.14 (m, 2H), 2.55 (m, 11H), 3.66 (s, 3H), 3.82 (s, 3H), 4.24 (t, 2H), 6.62 (m, 1H), 6.78 (m, 3H), 6.89-7.04 (m, 4H), 7.15 (m, 1H), 7.34 (s, 1H), 8.62 (s, 1H).

Mass Spectrum ES 580 (MH−), 582 (MH+)

Example 45

Preparation of Compound No. 45 in Table 4

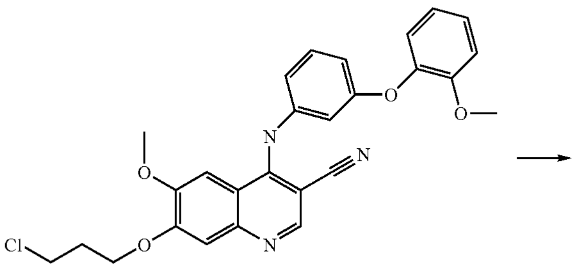

Example 42

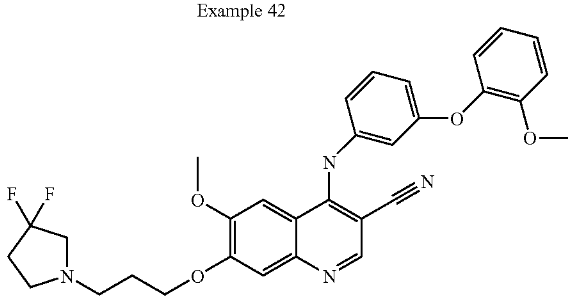

Example 45

7-(3-chloropropoxy)-6-methoxy-4-{[3-(2-methoxyphenoxy)phenyl]amino}quinoline-3-carbonitrile (300 mg, 0.6 mmol) [Example 42], 3,3-difluoropyrolidine hydrochloride (171 mg, 1.2 mmol), sodium iodide (180 mg, 1.2 mmol) and potassium carbonate (414 mg, 3.0 mmol) were heated at 85°

C. in dimethylformamide (20 ml) for 12 hours. The reaction mixture was evaporated and the residue was partitioned between dichloromethane and water. The organic layer was separated and the aqueous layer re-extracted with dichloromethane. The organics were combined, dried over magnesium sulfate, filtered and then evaporated in vacuo. The residue was purified by flash chromatography, eluting with a gradient of dichloromethane to 4% methanol in dichloromethane to give an oil. The oil was triturated with diethyl ether to leave the title compound as a solid (108 mg, 32%).

H NMR spectrum (300 MHz DMSO): 1.95 (m, 2H), 2.23 (m, 2H), 2.58 (t, 2H), 2.71 (t, 2H), 2.90 (t, 2H), 3.74 (s, 3H), 3.89 (s, 3H), 4.19 (t, 2H), 6.64 (m, 2H), 6.84 (d, 1H), 6.95 (m, 1H), 7.07 (d, 1H), 7.15 (m, 2H), 7.27 (t, 1H), 7.30 (s, 1H), 7.63 (s, 1H), 8.44 (s, 1H), 9.39(s, 1H).

Mass Spectrum ES 559 (MH−), 561 (MH+)

Example 46

Preparation of Compound No. 46 in Table 4

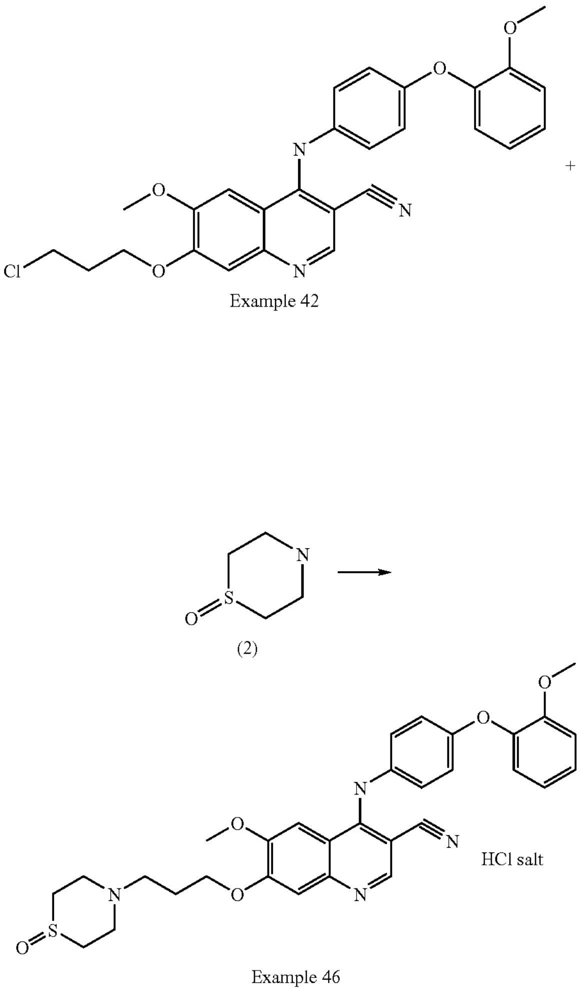

The title compound was prepared by reaction of Example 42 with 5 molar equivalents of Intermediate (2) (1-oxothiomorpholine) in the presence of 1 molar equivalent of NaI and 5 molar equivalents of anhydrous potassium carbonate at a temperature of 60° C. for 18 hours in dimethyl acetamide.

Mass Spectrum m/e 573 ($M^+$+H)

NMR Spectrum (d-6-DMSO, δ values) 2.44 (m, 2H), 3.24 (d, 2H), 3.45 (m, 6H), 3.71 (m, 2H), 3.81 (s, 3H), 4.06 (s, 3H), 4.38 (t, 2H), 7.04 (m, 3H), 7.13 (m, 1H), 7.26 (m, 2H), 7.46 (d, 2H), 7.56 (s, 1H), 8.21 (s, 1H), 8.95 (s, 1H), 11.06 (broad, 1H), 11.44 (broad, 1H)

Intermediate (2) (1-oxothiomorpholine)

Intermediate (2) was prepared as described in Chadha et al (1983) J. Med. Chem. (1983), 26(6), 916-22

Example 47

Preparation of Compound No. 47 in Table 4

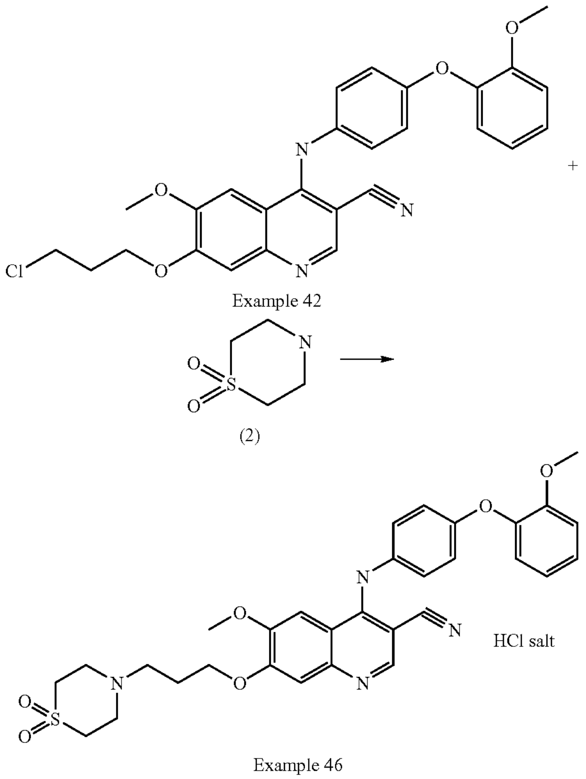

The title compound was prepared by reaction of Example 42 with 5 molar equivalents of Intermediate (2) (1,1-dioxothiomorpholine) in the presence of 1 of molar equivalent of NaI and 5 molar equivalents of anhydrous potassium carbonate at a temperature of 60° C. for 120 hours in dimethyl acetamide.

Mass Spectrum m/e 589 ($M^+$+H)

NMR Spectrum (d-6-DMSO, δ values) 2.32 (m, 2H), 3.42 (m, 8H), 3.63 (m, 2H), 3.74 (s, 3H), 3.99 (s, 3H), 4.30 (t, 2H), 6.98 (m, 3H), 7.05 (m, 1H), 7.19 (m, 2H), 7.40 (d, 2H), 7.48 (s, 1H), 8.15 (s, 1H), 8.91 (s, 1H), 11.05 (broad, 1H)

Intermediate (2) (1,1,-dioxomorpholine)

Intermediate (2) was prepared as described in Lazer et al (1994) J. Med. Chem. 37(7), 913-23.

Example 48

Preparation of Compound No. 48 in Table 4

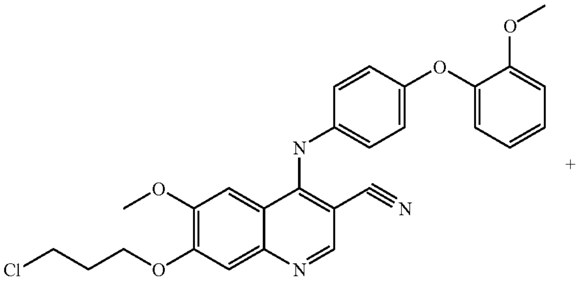

Example 42

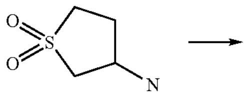

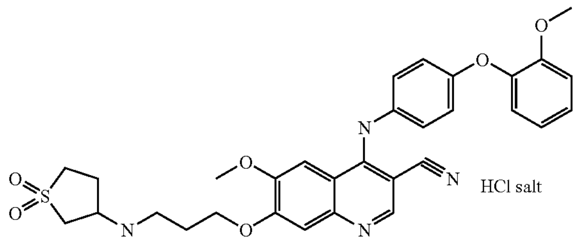

Example 47

The title compound was prepared by reactin of Example 42 with 5 molar equivalents of 1,1-dioxo-3-amino-tetrahydrothiophene in the presence of 1 molar equivalent of NaI and 5 molar equivalents of anhydrous potassium carbonate at a temperature of 60° C. for 144 hours in dimethyl acetamide.

Mass Spectrum m/e 589 ($M^{+}$+H)

NMR Spectrum (d-6-DMSO, δ values, 373K) 2.28 (m, 2H), 2.40 (m, 1H), 2.65 (m, 1H), 3.18 (m, 2H), 3.48 (m, 4H), 3.78 (s, 3H), 3.98 (s, 3H), 4.09 (m, 1H), 4.35 (t, 2H), 6.97 (m, 3H), 7.03 (m, 1H), 7.17 (m, 2H), 7.31 (d, 2H), 7.50 (s, 1H), 7.99 (s, 1H), 8.61 (s, 1H), 10.14 (broad, 1H)

Example 49

Preparation of Compound No. 49 in Table 4

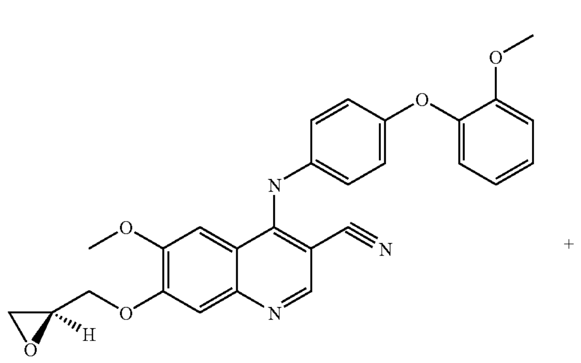

(1)

-continued

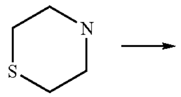

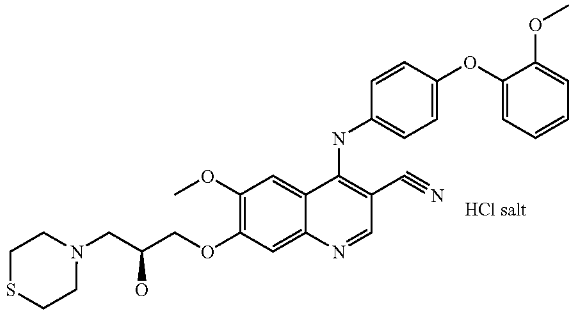

Example 49

The title compound was prepared by reaction of Intermediate (1) wih 20 molar equivalents of thiomorpholine at a temperature of 60° C. for 18 hours in dimethyl acetamide.

Mass Spectrum m/e 573 ($M^{+}$+H)

NMR Spectrum (d-6-DMSO, δ values) 2.85 (m, 2H), 3.26 (m, 6H), 3.74 (s, 3H), 3.76 (m, 2H), 3.99 (s, 3H), 4.19 (m, 2H), 4.54 (m, 1H), 6.11 (broad, 1H), 6.97 (m, 3H), 7.05 (m, 1H), 7.19 (m, 2H), 7.38 (d, 2H), 7.54 (s, 1H), 8.15 (s, 1H), 8.84 (s, 1H), 10.36 (broad, 1H), 10.91 (broad, 1H)

Intermediate (1)

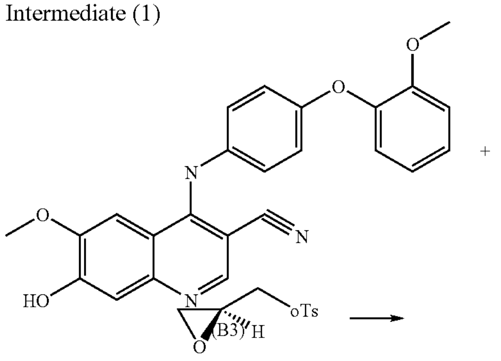

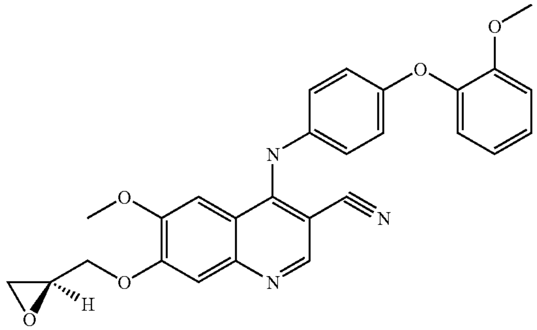

(1)

Intermediate (1) was prepared by reaction of Intermediate (B3) with (2S)-(+)-Glycidyl tosylate in the presence of anhydrous potassium carbonate at room temperature for 72 hours in DMSO.

Mass Spectrum m/e 470 ($M^{+}$+H)

Example 50

Preparation of Compound No. 50 in Table 4

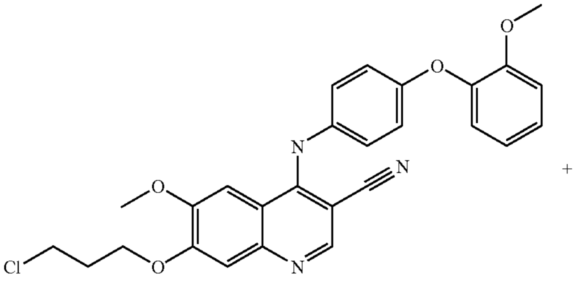

(1)

+

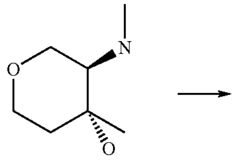

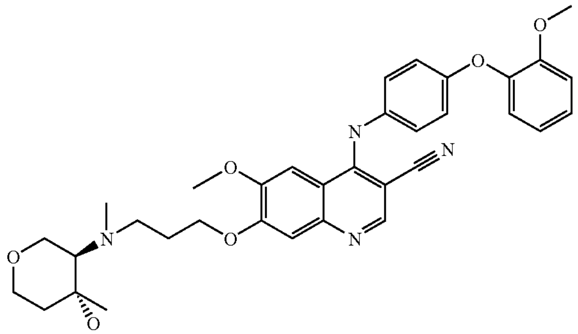

Example 50

Intermediate (1) was reacted with 1,5-anhydro-2,4-dideoxy-3-C-methyl-4-(methylamino)-D-erythro-pentitol in the presence of NaI and potassium carbonated at a temperature of 100° C. for 24 hours in DMA.

Mass Spectrum m/e 599.27 ($M^{+}$+H).

NMR Spectrum (d-6-DMSO, δ values) 1.42(s, 3H), 1.74 (m, 2H), 2.36(m, 2H), 2.74&2.97(2d, 3H), 3.2-3.8(m, 6H), 3.74(s, 3H), 3.9(s, 3H), 4.13-4.35(m, 3H), 6.95(m, 3H), 7.04 (d, 1H), 7.19(m, 2H), 7.4(d, 2H), 7.55(s, 1H), 8.22(s, 1H), 8.9(s, 1H), 9.7(br.s, 1H), 11.2(v.br.s, 1H).

Example 51

Preparation of Compound No. 51 in Table 4

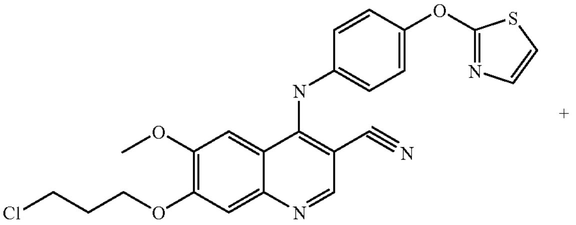

(1)

+

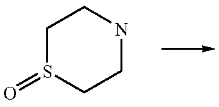

(2)

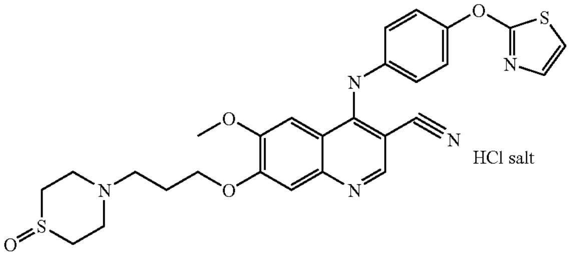

Example 51

The title compound was prepared by reaction of Intermediate (1) with 5 molar equivalents of Intermediate (2) in the presence of 1 molar equivalent of NaI and 5 molar equivalents of anhydrous potassium carbonate at a temperature of 60° C. for 44 hours in dimethyl acetamide.

Mass Spectrum m/e 550 ($M^{+}$+H)

NMR Spectrum (d-6-DMSO, δ values) 2.43 (m, 2H), 3.26 (d, 2H), 3.45 (m, 6H), 3.71 (m, 2H), 4.06 (s, 3H), 4.38 (t, 2H), 7.35 (d, 1H), 7.40 (d, 1H), 7.60 (m, 5H), 8.17 (s, 1H), 8.93 (s, 1H), 10.92 (broad, 1H), 11.29 (broad, 1H)

Intermediate (1)

Intermediate (1) was prepared as described in Example 41.

Intermediate (2)

Intermediate (2) was prepared as desribed in Chadha et al (1983) J. Med. Chem. 26(6), 916-22.

Example 52

Preparation of Compound No. 52 in Table 4

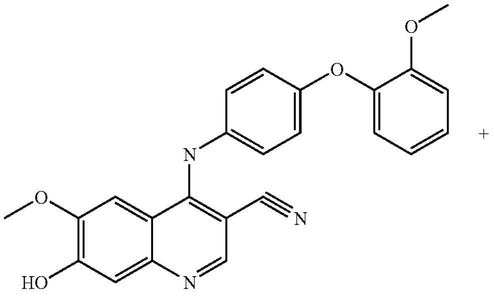

(B3)

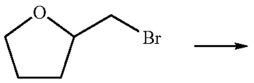

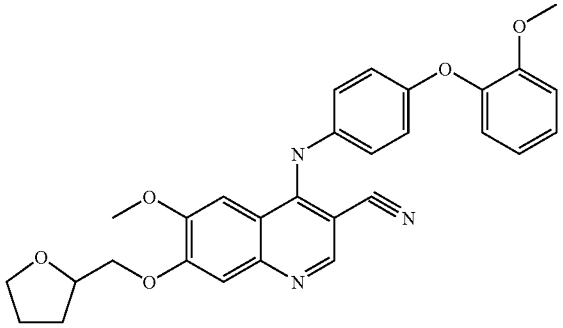

Example 52

The title compound was prepared by reacton of Intermediate (B3) with 1.2 molar equivalents of 2-bromomethytetrahydrofuran in the presence of 2.2 molar equivalents of anhydrous potassium carbonate at a temperature of 65° C. for 44 hours in dimethyl formamide.

Mass Spectrum m/e 498 ($M^{+}$+H)

Example 53

Preparation of Compound No. 53 in Table 4

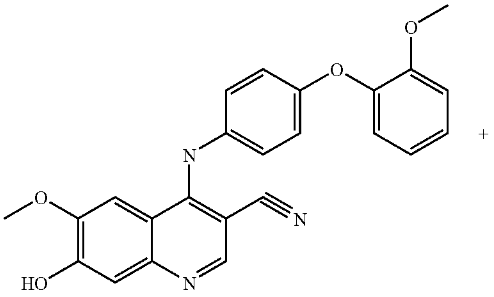

(B3)

-continued

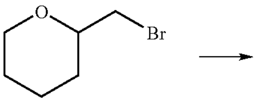

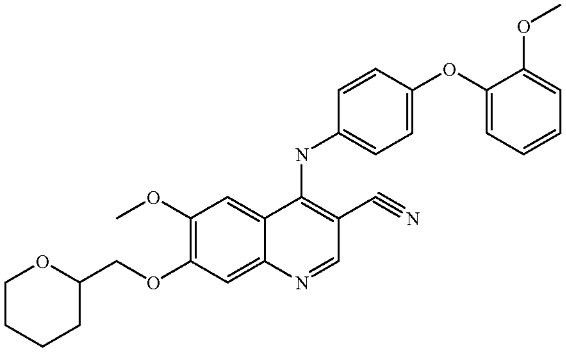

Example 53

The title compound was prepared by reaction of Intermediate (B3) with 1.2 molar equivalents of 2-bromomethyltetrahydropyran in the presence of 2.2 molar equivalents anhydrous potassium carbonate at a temperature of 65° C. for 44 hours in dimethyl formamide.

Mass Spectrum m/e 512 ($M^{+}$+H)

Example 54

Preparation of Compound No. 54 in Table 4

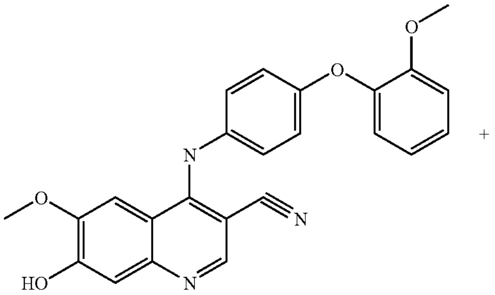

(B3)

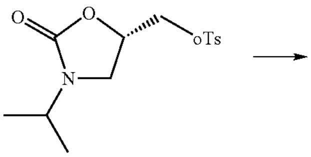

(2)

-continued

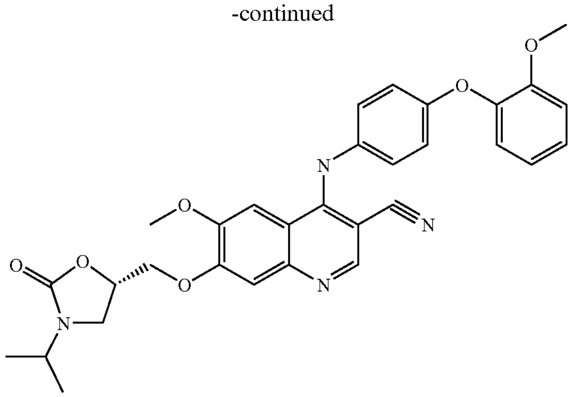

Example 53

The title compound was prepared by reaction of Intermediate (B3) with 1.2 molar equivalents of 5-(S)-para-toluenesulphonyloxymethyl-3-isopropyl-1,3-oxazolan-2-one in the presence of 2.2 molar equivalents of anhydrous potassium carbonate at a temperatue of 65° C. for 44 hours in dimethyl formamide.

Mass Spectrum m/e 555 ($M^+$+H)

Example 55

Preparation of Compound No. 55 in Table 4

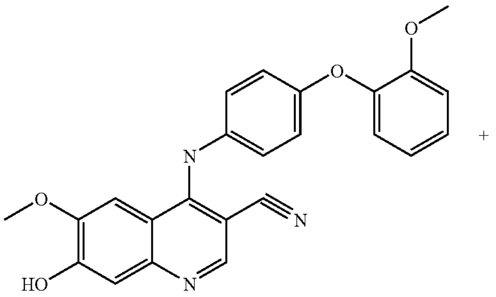

(B3)

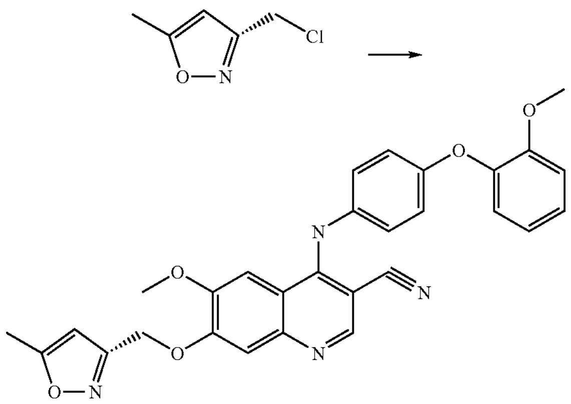

Example 55

The title compound ws prepared by reaction of Intermediate (B3) with 1.2 molar equivalents of 3-(chloromethyl)-5-methylisoxazole in the presence of 2.2 molar equivalents anhydrous potassium carbonate at a temperature of 65° C. for 44 hours in dimethyl formamide.

Mass Spectrum m/e 509 ($M^+$+H)

Example 56

Preparation of Compound No. 56 in Table 4

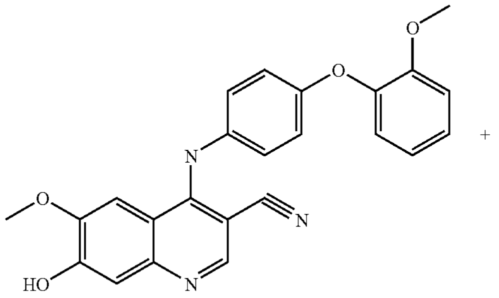

(B3)

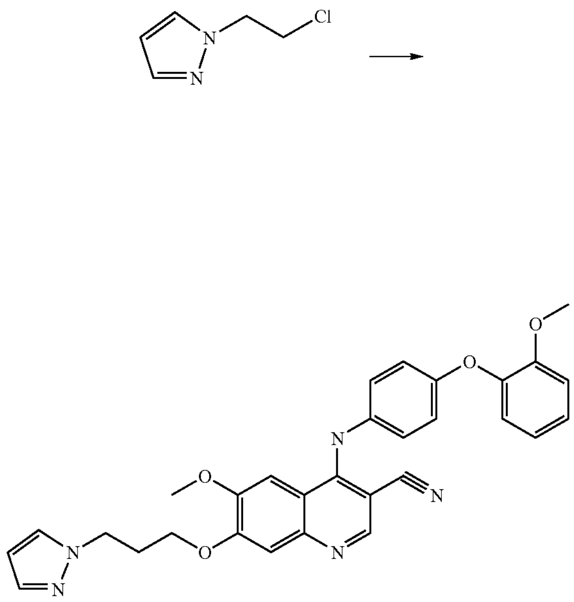

Example 56

The title compound was prepared by reaction of Intermediate (B3) with 1.2 molar equivalents of 1-(2-chloroethyl)-pyrazole in the presence of 2.2 molar equivalents of anhydrous potassium carbonate at a temperature of 100° C. for 42 hours in dimethyl formamide.

Mass Spectrum m/e 508 ($M^+$+H)

Example 57

Preparation of Compound No. 57 in Table 4

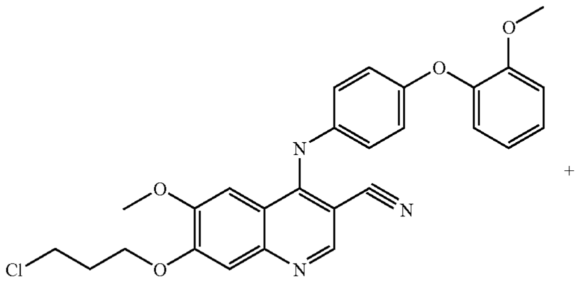

(1)

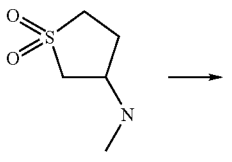

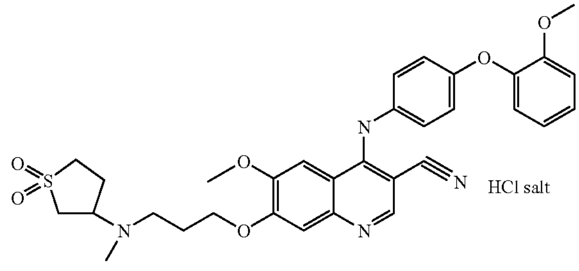

Example 57

The title compound was prepared by reaction of Intermediate (1) with 6 molar equivalents of 1,1-dioxo-3-N-methylamino-tetrahydrothiophene in the presence of 1 molar equivalent of NaI and 5 molar equivalents of anhydrous potassium carbonate at a temperature of 60° C. for 18 hours in dimethyl acetamide.

Mass Spectrum m/e 603 ($M^+$+H)

NMR Spectrum (d-6-DMSO, δ values) 2.34 (m, 4H), 2.68 (m, 1H), 3.23 (m, 2H), 3.46 (m, 4H), 3.72 (s, 3H), 3.98 (s, 3H), 4.26 (m, 3H), 6.96 (m, 3H), 7.05 (m, 1H), 7.18 (m, 2H), 7.40 (d, 2H), 7.56 (s, 1H), 8.22 (s, 1H), 8.90 (s, 1H)

Intermediate (1)

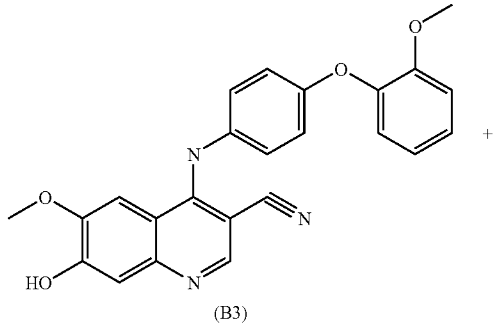

(B3)

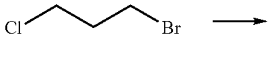

-continued

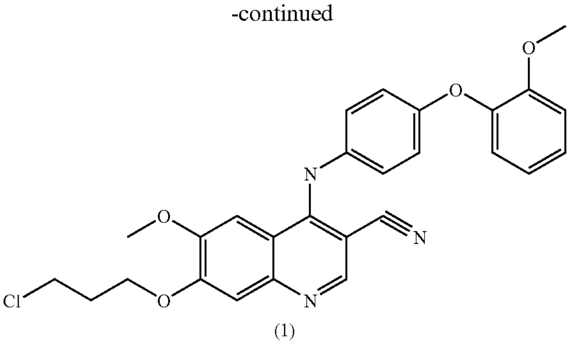

(1)

Intermediate (1) was prepared by reaction of Intermediate (B3) with 1-chloro-3-bromopropane in the presence of $KO^tBu$ (1.0M in THF) at room temperature for 18 hours in DMSO.

Mass Spectrum m/e 490 ($M^+$+H)

Example 58

Preparation of Compound No. 58 in Table 4

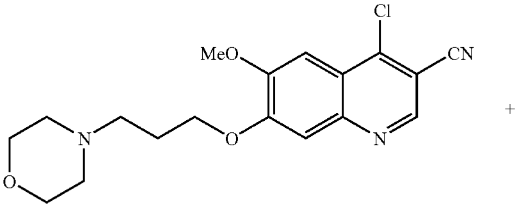

(1)

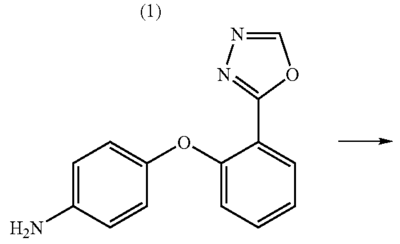

(2)

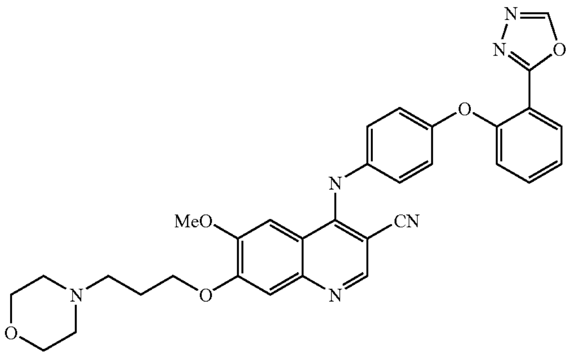

Step 1

Intermediate (1) was prepared by alkylation of Intermediate (A7) with N-(3-chloropropyl)-morpholine in toluene solution at 110° C. for 18 hours in the presence of cesium carbonate, tetra-n-butyl ammonium iodide and 4A sieves Mass Spectrum m/e 511 $(M+H)^+$.

Step 2

Intermediate (2) was prepared from salicyl hydrazide by reaction of the hydrazide with triethylorthoformate to give, after chromatographic purification, the 2-hydroxyphenyloxadiazole, Mass Spectrum m/e 163 ($M^{+}$+H), then the 2-hydroxyphenyloxadiazole was reacted with 4-fluoronitrobenzene, in a procedure analogous to that in Preparation B to give, after chromatographic purification, 2-(4-nitrophenoxy)phenyloxadiazole.

Mass Spectrum m/e 284 (M++H), 2-(4-Nitrophenoxy)phenyloxadiazole was reduced in ethyl acetate solution with hydrogen and 5% Pd/C to produce Intermediate (2).

Mass Spectrum m/e 254 (M++H)

Step 3

Intermediate (1) was reacted with Intermediate (2) in n-propanol solution at 110° C. for 16 hours in the presence of 1 molar equivalent of 1.0M ethereal HCl to give, after chromatographic purification, the title compound Mass Spectrum m/e 579 ($M^{+}$+H).

Example 59

Preparation of Compound No. 59 in Table 4

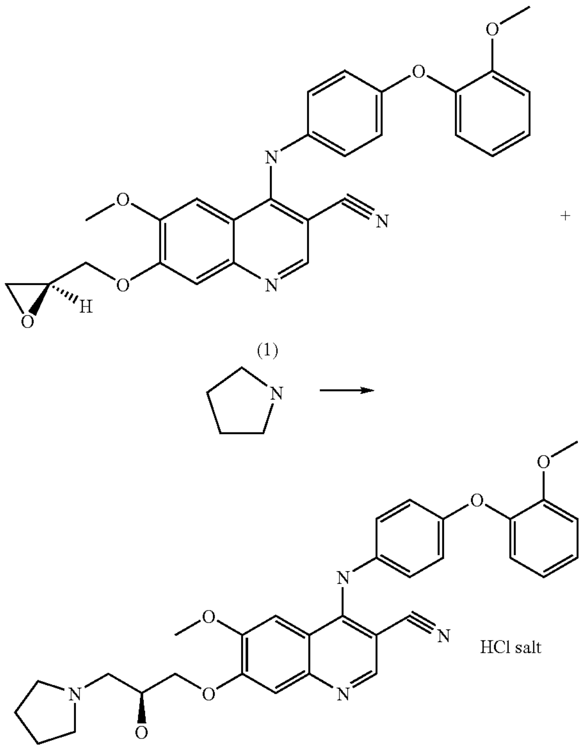

(1)

Example 59

The title compound was prepared by reaction of Intermediate (1) with 20 molar equivalents of pyrrolidine at a temperature of 60° C. for 18 hours in dimethyl acetamide.

Mass Spectrum m/e 541 ($M^{+}$+H)

NMR Spectrum (d-6-DMSO, δ values) 1.95 (m, 4H), 3.11 (m, 2H), 3.35 (m, 2H), 3.61 (m, 2H), 3.74 (s, 3H), 3.99 (s, 3H), 4.19 (m, 2H), 4.38 (m, 1H), 6.09 (broad, 1H), 6.97 (m, 3H), 7.05 (m, 1H), 7.19 (m, 2H), 7.38 (d, 2H), 7.55 (s, 1H), 8.17 (s, 1H), 8.85 (s, 1H), 10.10 (broad, 1H), 10.98 (broad, 1H)

Intermediate (1)

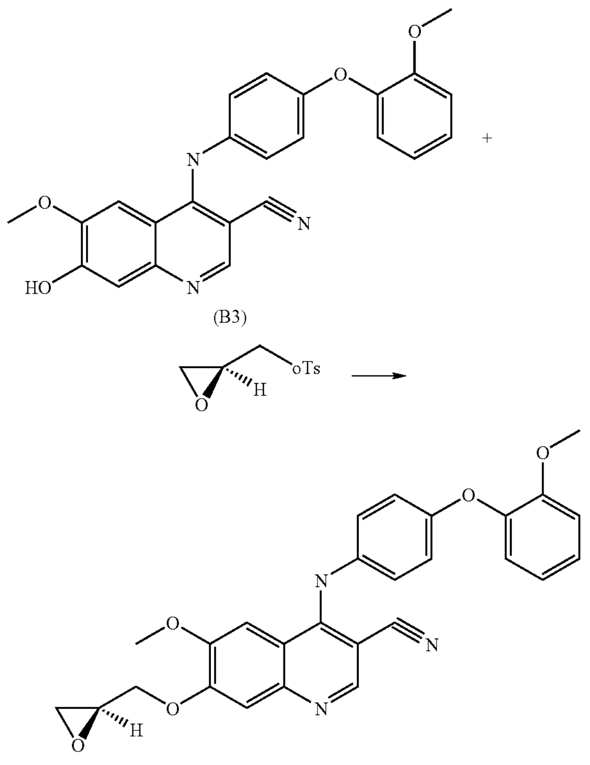

(B3)

(1)

Intermediate (1) was prepared by reaction of Intermediate (B3) with (2S)-(+)-Glycidyl tosylate in the presence of anhydrous potassium carbonate at room temperature for 72 hours in DMSO.

Mass Spectrum m/e 470 ($M^{+}$+H)

Example 60

Preparation of Compound No. 60 in Table 4

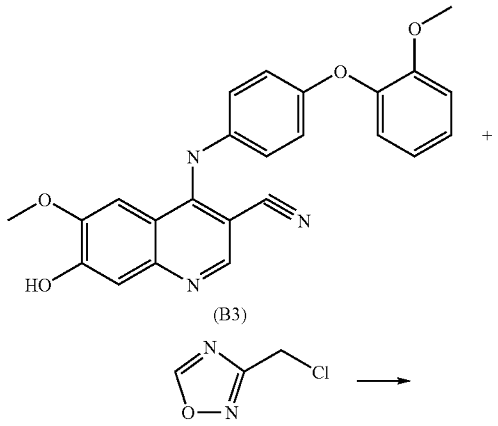

(B3)

-continued

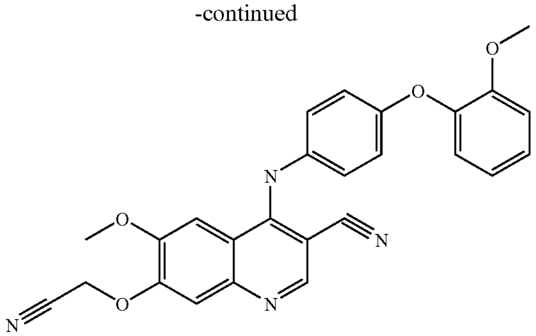

Example 60

The title compound was prepared by reaction of Intermediate (B3) with 1.2 molar equivalents 3-(chloromethyl)-1,2,4-oxadiazole in the presence of 2.2 molar equivalents anhydrous potassium carbonate at a temperature of 100° C. for 72 hours in dimethyl formamide.

Mass Spectrum m/e 453 ($M^+$+H)

NMR Spectrum (d-6-DMSO, δ values) 3.74 (s, 3H), 3.94 (s, 3H), 5.38 (s, 2H), 6.91 (m, 3H), 7.02 (m, 1H), 7.17 (m, 2H), 7.28 (d, 2H), 7.50 (s, 1H), 7.86 (s, 1H), 8.42 (s, 1H), 9.50 (s, 1H)

Example 61

Preparation of Compound No. 61 in Table 4

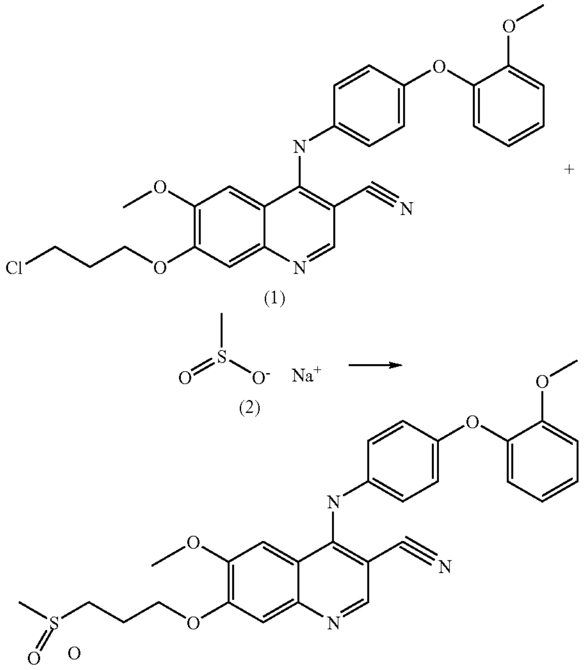

(1) (2)

Example 61

The title compound was prepared by reaction of Intermediate (1) with 1.2 molar equivalents sodium methanesulfinate at a temperature of 100° C. for 18 hours in dimethyl acetamide.

Mass Spectrum m/e 534 ($M^+$+H)

NMR Spectrum (d-6-DMSO, δ values) 2.23 (m, 2H), 3.03 (s, 3H), 3.28 (t, 2H), 3.73 (s, 3H), 3.91 (s, 3H), 4.25 (t, 2H), 6.91 (m, 3H), 7.02 (m, 1H), 7.15 (m, 2H), 7.23 (d, 2H), 7.31 (s, 1H), 7.75 (s, 1H), 8.37 (s, 1H), 9.40 (s, 1H)

Intermediate (1)

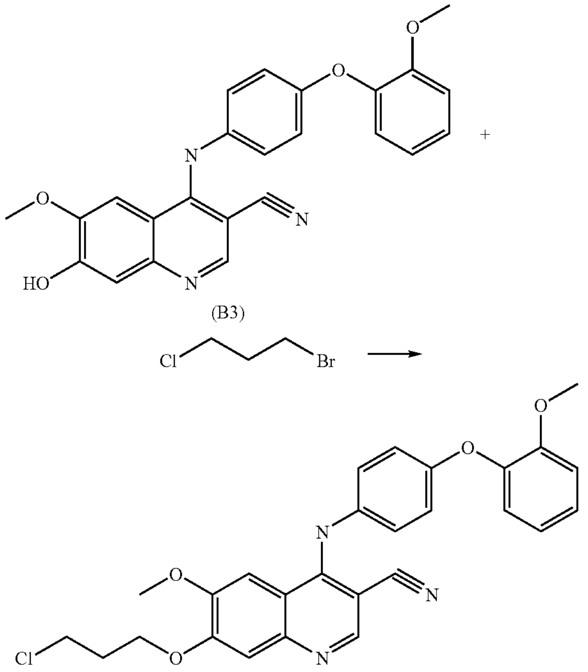

(B3) (1)

Intermediate (1) was prepared by reaction of Intermediate (B3) with 1-chloro-3-bromopropane in the presence of KO$^t$BU (111.0M in THF) at room temperature for 18 hours in DMSO.

Mass Spectrum m/e 490 ($M^+$+H)

Example 62

Preparation of Compound No. 62 in Table 4

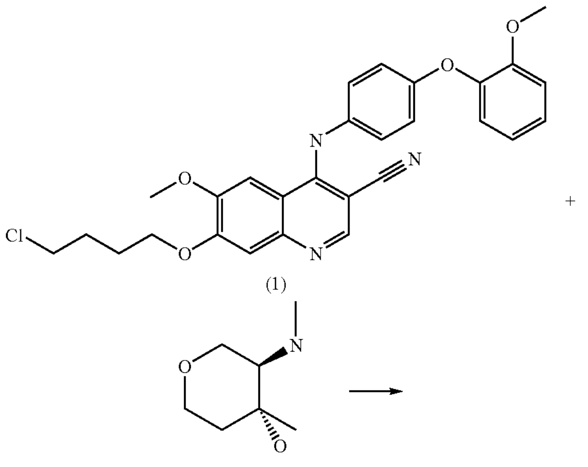

(1)

-continued

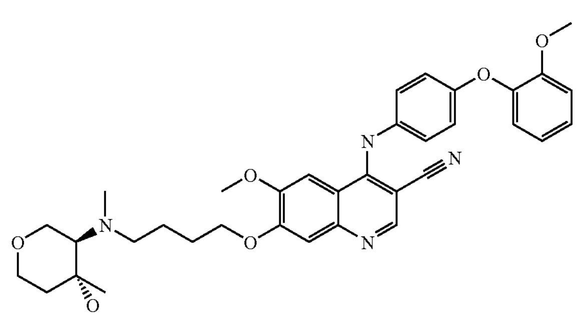

Example 62

The title compound was prepared by reaction of Intermediate (1) with 1,5-anhydro-2,4-dideoxy-3-C-methyl-4-(methylamino)-D-erythro-pentitol in the presence of NaI and potassium carbonate at a temperature of 100OC for 24 hours.

Mass Spectrum m/e 613 ($M^{+}$+H).

NMR Spectrum (d-6-DMSO, δ values) 1.40(s, 3H), 1.64-1.78 (m, 2H), 1.78-2.09(m, 4H), 2.69(d, 3H), 3.14-3.52(m, 3H), 3.6(t, 2H), 3.71(s, 3H), 3.65-3.8(m, 1H), 3.98(s, 3H), 4.1-4.29(m, 3H), 6.9-7.0(m, 3H), 7.03(d, 1H), 7.2(m, 2H), 7.38(d, 2H), 7.94(s, 1H), 8.13(s, 1H), 8.85(s, 1H), 9.43(br.s, 1H).

Intermediate (1)

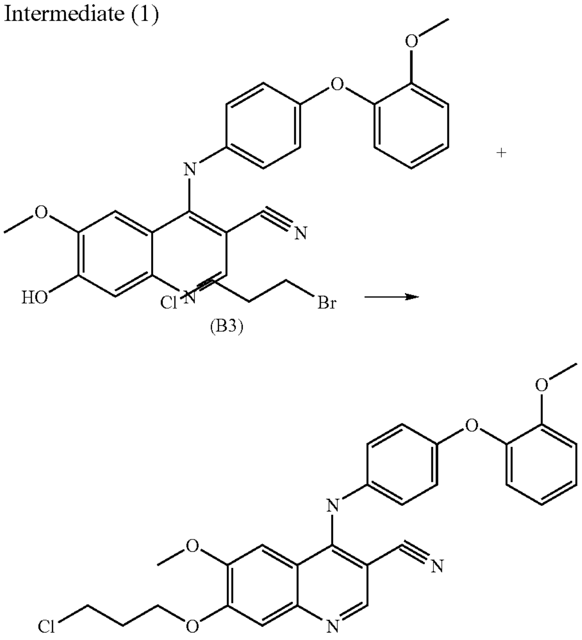

(B3)

(1)

Intermediate (1) was prepared by reaction of Intermediate (B3) with 1-chloro-3-bromopropane in the presence of KO$^{t}$Bu (1.0M in THF) at room temperature for 18 hours in DMSO.

Mass Spectrum m/e 490 ($M^{+}$+H)

Example 63

Preparation of Compound 63 in Table 5

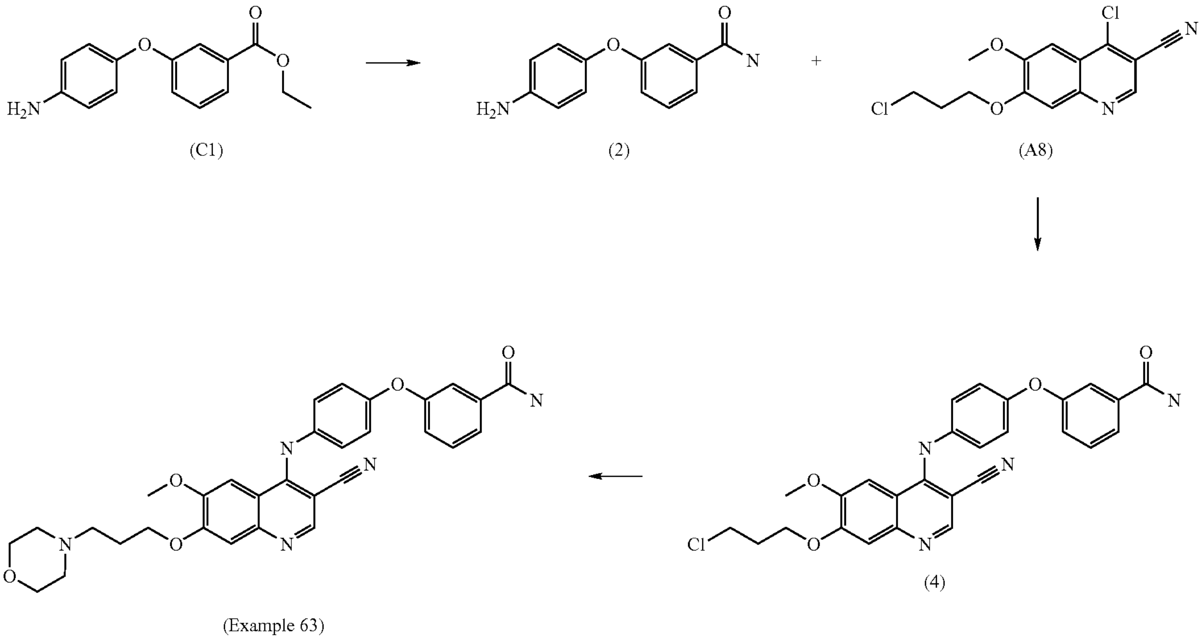

(C1)

(2)

(A8)

(4)

(Example 63)

Step 1

Intermediate (C1) was converted to the primary amide by treatment with formamide in DMA at room temperature for 5 minutes followed by treatment with sodium methoxide (25% in methanol) for 1 hr at 100° C. to yield, after chromatographic purification, Intermediate (2).

Mass Spectrum m/e 229.35 (M+H)+

Step 2

Intermediate (2) was reacted with Intermediate (A8) in n-propanol solution at 105° C. for 3 hours to give Intermediate (4).

Mass Spectrum m/e 503.27 (M+H)+

Step 3

Intermediate (4) was reacted with morpholine in the manner described for Example 11, Step 2 to yield, after chromatographic purification, the title compound.

Mass Spectrum m/e 554.3 $(M+H)^-$

NMR Spectrum (d-6-DMSO, δ values) 1.96 (m, 2H), 2.32-2.52 (m, 6H), 3.52-3.60 (m, 4H), 3.92 (s, 3H), 4.19 (t, 2H), 7.07-7.16 (m, 3H), 7.29-7.50 (m, 6H), 7.60 (d, 1H), 7.74 (s, 1H), 7.89 (s, 1H), 8.39 (s, 1H), 9.47 (s, 1H).

Example 64

Preparation of Compound 64 in Table 6

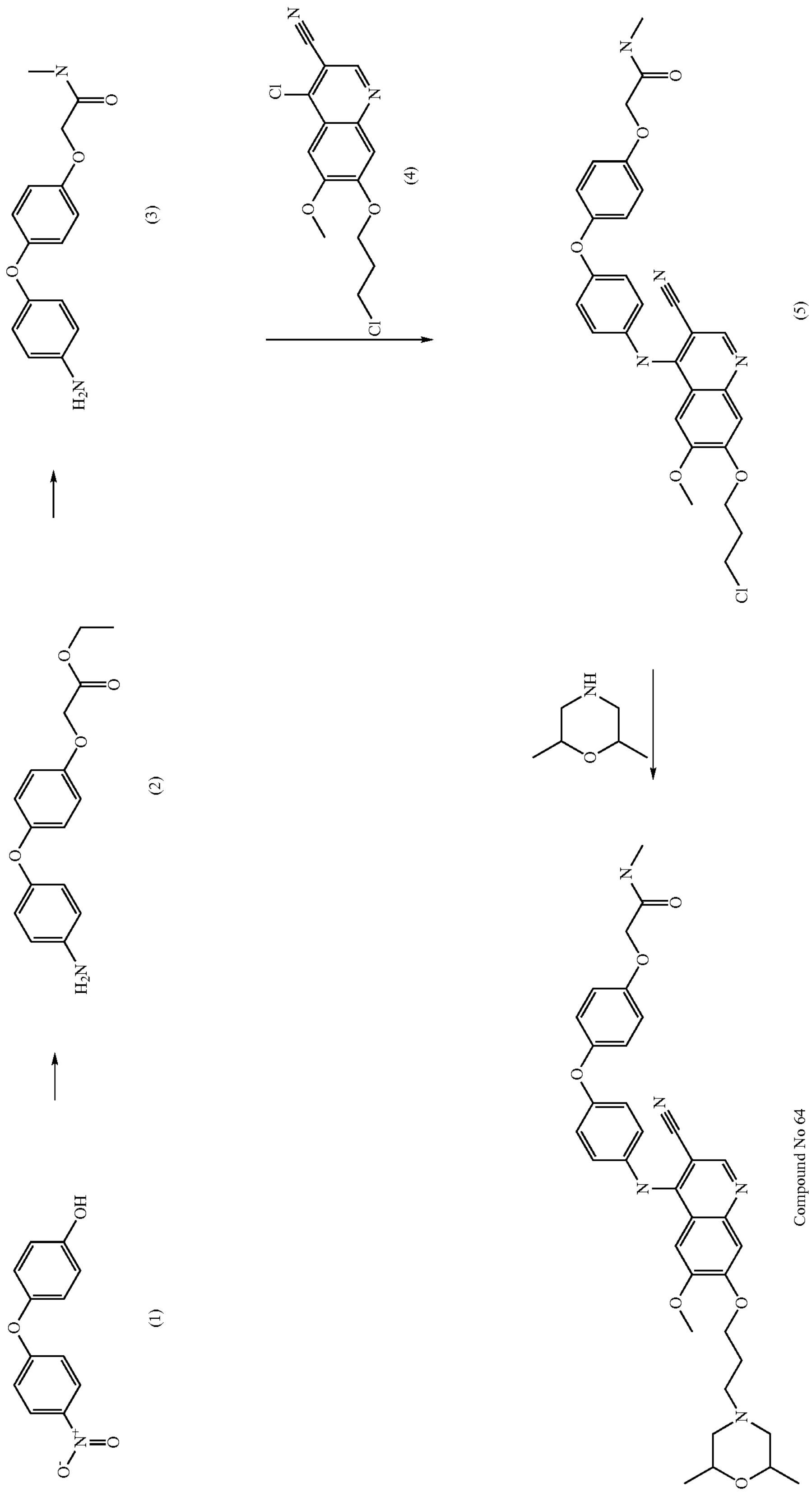
(1)
(2)
(3)
(4)
(5)
Compound No 64

Step 1

4-Fluoro-nitrobenzene and 4-hydroxyphenol were reacted together in DMA in the presence of potassium butoxide in a manner analogous to the preparation of 4-(4-nitrophenoxy)-phenol (Rev. Chim. (Bucharest), 1988, 39(6), 477-482) to give Intermediate (1).

Step 2

Intermediate (1) was reacted with ethyl bromoacetate in acetone solution for 3 hr at 65° C. in the presence of potassium carbonate and then the nitro group reduced to the corresponding aniline by reduction, at room temperature in ethyl acetate solution, with hydrogen and catalytic 5% Pd/C to give, after chromatographic purification, intermediate (2).

Mass Spectrum m/e 288.63 $(M+H)^+$

NMR Spectrum (d-6-DMSO, δ values) 1.19 (t, 3H), 4.14 (q, 2H), 4.68 (s, 2H), 4.88 (s, 2H), 6.55 (d, 2H), 6.68 (d, 2H), 6.75-6.87 (m, 4H).

Step 3

Intermediate (2) was converted to the corresponding N-methylamide by reaction with methylamine in methanol for 96 hr at 65° C. The product was purified by chromatography to give intermediate (3).

Mass Spectrum m/e 273.59 $(M+H)^+$

NMR Spectrum (d-6-DMSO, δ values) 2.63 (d, 3H), 4.37 (s, 2H), 4.88 (s, 2H), 6.54 (d, 2H), 6.68 (d, 2H), 6.80 (d, 2H), 6.89 (d, 2H), 7.86 (bs, 1H).

Step 4

Intermediate (3) was reacted with intermediate (A8) in n-propanol solution at 105° C. for 3 hr to give intermediate (5).

Mass Spectrum m/e 547.92 $(M+H)^+$

NMR Spectrum (d-6-DMSO, δ values) 2.19 (m, 2H), 2.66 (d, 3H), 3.83 (t, 2H), 3.99 (s, 3H), 4.30 (t, 2H), 4.44 (s, 2H), 7.00 (s, 4H), 7.07 (d, 2H), 7.44 (d, 2H), 7.50 (s, 1H), 8.00 (bs, 1H), 8.15 (s, 1H), 8.90 (s, 1H).

Step 5

Intermediate (5) was reacted with 2,6-dimethylmorpholine, for 96 hours at room temperature in the presence of sodium iodide to yield, after chromatographic purification, the title compound.

Mass Spectrum m/e 627.16 $(M+H)^+$

NMR Spectrum (d-6-DMSO D4 Acetic, 6 values) 1.12 (s, 3H), 1.14 (s, 3H), 2.34 (2H, m), 2.60-2.71 (m, 5H), 3.26 (m, 2H), 3.50 (d, 2H) 3.90-4.01 (m, 5H), 4.30 (t, 2H), 4.42 (s, 2H), 6.99 (s, 4H), 7.07 (d, 2H), 7.45 (d, 2H), 7.50 (s, 1H), 8.16 (s, 1H), 8.91 (s, 1H).

Assay for Inhibitors of the MAP Kinase Pathway

To evaluate inhibitors of the MAPK pathway a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60 min at room temperature in the presence or absence of potential inhibitors. The activated GST-MAPK was then incubated with myelin basic protein (MBP) as substrate for 10 min at room temperature in the presence of ATP, $Mg^{2+}$ and $^{33}P$-ATP. The reaction was stopped by addition of 20% v/v phosphoric acid. Incorporation of $^{33}P$ into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 μM [$\gamma^{33}P$]ATP, 8.33 mM $Mg(OAc)_2$, 0.5 mM sodium orthovanadate, 0.05% w/v BSA, 6.5 ng GST-MEK, 1 μg GST-MAPK and 16.5 μg MBP in a reaction volume of 60 μl.

Compounds tested of the present invention had $IC_{50}$ results typically less than 0.5 μM. For example, Compound No 11 gave an $IC_{50}$ of 0.0013 μM.

In Vitro MAP Kinase Assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate (MBP) for 60 min at room temperature in the presence of ATP, $Mg^{2+}$ and $^{33}P$-ATP. The reaction was stopped by addition of 20% v/v phosphoric acid. Incorporation of $^{33}P$ into the myelin basic protein was determined by capture of the substrate on a filter mat, washing and counting using scintillation methods.

The final assay solution contained 12 mM Tris, pH 7.5, 0.06 mM EGTA, 30 μM [$\gamma^{33}P$]ATP, 10 mM $Mg(OAc)_2$, 0.6 mM sodium orthovanadate, 0.06% w/v BSA, 28 ng GST-MAPK and 16.5 μg MBP in a reaction volume of 60 μl.

Compounds of the invention showed activity in this screen.

Cell Proliferation Assays

Cells were seeded into multi-well plates at 20 000-40 000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with XTT/PMS in PBSA and optical densities read at 450 nm. Compounds tested of the present invention had $IC_{50}$ results typically less than 30 μM. For example, Compound No 11 gave an $IC_{50}$ of 1.3 μM in HT29 human colon tumour cells.

What is claimed is:

1. A compound of Formula (Ia), (Ia)

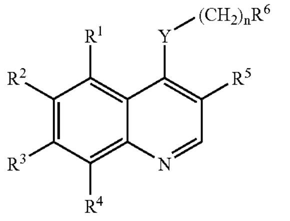

or a pharmaceutically acceptable salt thereof;

wherein:

n is 0 or 1;

Y is selected from —NH—, —O—, —S—, or $—NR^7—$ where $R^7$ is alkyl of 1-6 carbon atoms;

$R^5$ is cyano, fluoro, chloro or bromo;

$R^6$ is a group $—R^8—X—R^9$ where $R^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

where X is selected from —NH—, —O—, —S—, $CH_2$ or —$NR^{7'}$— where $R^{7'}$ is alkyl of 1-6 carbon atoms, and $R^9$ is a group $(CH_2)_mR^{10}$ where m is 0 or an integer of from 1-3 and $R^{10}$ is an optionally substituted aryl or optionally substituted cycloalkyl ring of up to 10 carbon atoms, or $R^{10}$ is a optionally substituted heterocyclic ring or an N-oxide of any nitrogen containing ring;

$R^1$, $R^2$, $R^4$ are independently selected from hydrogen, hydroxy, halogeno, cyano, nitro, trifluoromethyl, $C_{1-3}$alkyl, —$NR^{11}R^{12}$— (wherein $R^{11}$ and $R^{12}$, which may be the same or different each represents hydrogen, or $C_{1-3}$alkyl), or a group $R^{13}$—$X^1$—$(CH_2)_x$ wherein x is 0 or an integer of from 1 to 3, $X^1$ represents a direct bond, —O—, —$CH_2$—, —OC(O)—, —C(O)—, —S—, —SO—, —$SO_2$—, —$NR^{14}C(O)$—, —$NR^{14}C(O)O$—, —$C(O)NR^{15}$—, —$C(O)ONR^{15}$—, —$SO_2NR^{16}$—, —$NR^{17}SO_2$— —$NR^{18}$— or —$NR^{18}NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl)), and $R^{13}$ is hydrogen, optionally substituted hydrocarbyl, or optionally substituted heterocyclyl; and $R^3$ is a group of formula $R^{13a}$—$(CH_2)_y$—$X^1$—$(CH_2)_x$ where $R^{13\ a}$ is as defined for $R^{13}$ above, and $X^1$ and x are as defined above, y is 0 or an integer between 1 and 5, wherein $(CH_2)_y$ is optionally interposed by an $X^1$ group; provided that $R^{13a}$ is selected from phenyl or optionally substituted heterocyclyl and the optional substituents for phenyl and aromatic heterocyclyl rings are selected from: $C_{2-5}$alkenyl, $C_{2-5}$alkynyl, $C_{1-5}$alkanoyl, $C_{1-5}$alkoxycarbonyl, $C_{1-3}$alkanoyl$C_{1-3}$alkyl, $C_{1-3}$alkoxy$C_{1-3}$alkyl, $C_{1-5}$alkylthio, $C_{1-5}$alkylsulphanyl, $C_{1-5}$alkylsulphonyl, N,N-di-$C_{1-5}$alkylamino, cyano$C_{1-5}$alkyl and the optional substituents for non-aromatic heterocyclyl rings further include hydroxy$C_{1-5}$alkoxy, amino, amino$C_{1-5}$alkyl, N—$C_{1-5}$alkylamino, carboxy, cyano, —$CONR^{zz}R^{zz'}$— and —$NR^{zz''}COR^{zz'''}$ (wherein $R^{zz}$, $R^{zz'}$, $R^{zz''}$ and $R^{zz'''}$ each independently represent hydrogen, $C_{1-5}$alkyl or $C_{1-3}$alkoxy$C_{1-3}$alkyl).

2. A compound according to claim 1 wherein $R^5$ is cyano.

3. A compound according to claim 1 wherein, in the definition of $R^3$, $X^1$ is selected from —O—, —$NR^{14}C(O)$—, or —$NR^{18}$— (wherein $R^{14}$ and $R^{18}$ are as defined in claim 1), X is —O—, x is 0, y is an integer between 1 and 5, $R^5$ is cyano and $R^{13a}$ is selected from azetidinyl, pyrrolidinyl, tetrahydrofuranyl, 1,3-dioxolanyl, 1,3-oxazolidinyl, 1,2,4-oxadiazolidinyl, 1,1-dioxoctetrahydrothiophenyl, morpholinyl, piperidinyl, piperazinyl, 1,3-dioxanyl, tetrahydropyranyl, 1,1-dioxo-tetrahydrothiopyranyl, thiomorpholinyl, 1-oxothiomorpholinyl, 1,1-dioxo thiomorpholinyl, 2,3-dihydropyrrolyl, imidazolyl, pyrazolyl, 1,3-thiazolyl, 1,3,4-oxadiazolyl, isoxazolyl, 1,2,4-thiadiazolyl, furanyl, 2,5-dihydro-1,2,4-oxadiazolyl and pyrimidinyl.

4. A compound according to claim 3 wherein $X^1$ is —O— and $R^{13a}$ is selected from: 4-methoxyethylpiperazin-1-yl, 4-acetylpiperazin-1-yl, 3-methylsulphonylpyrrolidin-1-yl and 4-ethylsulphonylpiperazin-1-yl

5. A compound according to claim 1 where the substituent on $R^{10}$ is a group of the sub-formula (ii):

$$—Z—(CH_2)_pR^{100}—R^{101} \quad (ii)$$

wherein

—Z— is a direct bond or a group of sub-formula (iii)

$$—X^{121}—R^{751}—X^{131}—(R^{761}—X^{141})_s—R^{771}—X^{151})_{s''}— \quad (iii)$$

wherein $X^{121}$, $X^{131}$ each $X^{141}$ and each $X^{151}$ are independently selected from —O—, —C(O)—, —C(O)O—, —S—, —SO—, —$SO_2$—, —$NR^{781}C(O)$—, —$NR^{781}C(O)O$—, —$CONR^{791}$—, —$C(O)ONR^{791}$—, —$SO_2NR^{801}$—, —$NR^{811}SO_2$— or —$NR^{821}$— (wherein $R^{781}$, $R^{791}$, $R^{801}$, $R^{811}$ and $R^{821}$ each independently represents hydrogen, $C_{1-3}$alkyl optionally substituted by hydroxy, or $C_{1-3}$alkoxy$C_{2-3}$alkyl) and each $X^{131}$, $X^{141}$ and $X^{151}$ may additionally be a direct bond;

s and s" are independently selected from 0, 1, 2 or 3;

$R^{751}R^{761}$ and $R^{771}$ are independently selected from $C_{1-6}$alkylene, $C_{2-6}$alkenylene or $C_{2-6}$alkynylene optionally substituted by halo and hydroxy or $R^{751}$, $R^{761}$ and $R^{771}$ can each independently be direct bonds;

$R^{100}$ is an optionally substituted divalent heterocyclic group, $C_{1-5}$alkylene, or divalent $C_{3-7}$cycloalkyl, $R^{101}$ is hydrogen, amino or a group of sub-formula (iv)

$$—X^{161}R^{831}—(X^{171}R^{841})_t—X^{181}R^{851} \quad (iv)$$

wherein $X^{161}$, $X^{181}$ and each $X^{171}$ are each independently selected from a direct bond, —O—, —C(O)—, —S—, —SO—, —$SO_2$—, —$NR^{861}C(O)$—, —$NR^{861}C(O)O$—, —$CONR^{871}$—, —$C(O)ONR^{871}$—, —$SO_2NR^{881}$—, —$NR^{891}SO_2$— or —$NR^{901}$— (wherein $R^{861}$, $R^{871}$, $R^{881}$, $R^{891}$ and $R^{901}$ each independently represents hydrogen, $C_{1-3}$alkyl or $C_{1-3}$alkoxy$C_{2-3}$alkyl), $R^{831}$ and each $R^{841}$ are independently selected from $C_{1-6}$alkylene, $C_{2-6}$alkenylene or $C_{2-6}$alkynylene, $R^{851}$ is selected from hydrogen, $C_{1-6}$alkyl, $C_{2-6}$alkenyl or $C_{2-6}$alkynyl, and t is 0, 1, 2 or 3; and p is 0, 1, 2 or 3.

6. A pharmaceutical composition comprising a compound as defined in any one of claims 1, 2, 3 and 5 in combination with a pharmaceutically acceptable carrier or excipient.

7. A process for the preparation of a compound of Formula (Ia) as defined in claim 1 by reacting a compound of Formula (III)

(III)

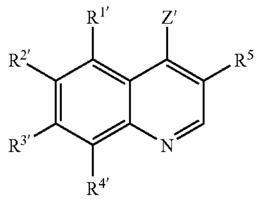

where $R^{1'}$, $R^{2'}$, $R^{3'}$, $R^{4'}$ represent $R^1$, $R^2$, $R^3$ and $R^4$ respectively as defined in claim 1 or $R^{1'}$, $R^{2'}$, $R^{3'}$, $R^{4'}$ represent a precursor thereof having the formula $R^{13'}—X^1—(CH_2)_x$ wherein x and $X^1$ are as defined in claim 1 and wherein $R^{13'}$ is a $C_{1-5}$alkyl which is substituted with halo other than fluoro, $R^5$ is as defined in claim 1 and Z' is a leaving group, with a compound of Formula (IV)

$$H—Y(CH_2)_nR^{6'} \quad (IV)$$

where Y and n are as defined in claim 1 and $R^{6'}$ is a group $R^6$ as defined in claim 1 or a precursor thereof; and optionally thereafter converting precursor groups $R^{1'}$, $R^{2'}$, $R^{4'}$ and $R^{6'}$ to groups of formula $R^1$, $R^2$, $R^3$, $R^4$ and $R^6$ respectively, or converting a group $R^1$, $R^2$, $R^3$, $R^4$ and $R^6$ to a different such group.

* * * * *